United States Patent [19]

Ono et al.

[11] Patent Number: 5,635,527

[45] Date of Patent: Jun. 3, 1997

[54] CARBOXYLIC ACID COMPOUND HAVING CONDENSED RING, SALT THEREOF AND PHARMACEUTICAL USE THEREOF

[75] Inventors: Shinichiro Ono; Tomohiro Yoshida; Atsuyuki Ashimori; Keigo Kosaka; Takehiro Okada; Kazuhiro Maeda; Masahiro Eda; Fumio Mori; Yoshihisa Inoue; Hajime Ebisu; Teruaki Imada; Ruriko Ikegawa; Feng Wang; Norifumi Nakamura, all of Hirakata, Japan

[73] Assignee: The Green Cross Corporation, Osaka, Japan

[21] Appl. No.: 591,537

[22] PCT Filed: Jun. 6, 1995

[86] PCT No.: PCT/JP95/01119

§ 371 Date: Feb. 6, 1996

§ 102(e) Date: Feb. 6, 1996

[87] PCT Pub. No.: WO95/33720

PCT Pub. Date: Dec. 14, 1995

[30] Foreign Application Priority Data

Jun. 6, 1994 [JP] Japan ................................. 6-124092
Feb. 28, 1995 [JP] Japan ................................. 7-039974

[51] Int. Cl.$^6$ ................ A61K 31/715; A61K 31/55; A61K 31/44; A61K 31/445; A61K 31/405; A61K 31/40; A61K 31/38; A61K 31/34; C08B 37/16; C07D 401/12; C07D 405/12; C07D 409/12

[52] U.S. Cl. ................ 514/414; 514/58; 514/212; 514/300; 514/301; 514/302; 514/320; 514/323; 514/324; 514/333; 514/337; 514/339; 514/415; 514/418; 514/419; 514/422; 514/443; 514/444; 514/445; 514/447; 514/448; 514/469; 514/470; 536/103; 540/602; 546/113; 546/114; 546/115; 546/116; 546/196; 546/201; 546/202; 546/256; 546/277.7; 546/278.1; 546/281.1; 546/284.1; 546/284.4; 546/284.7; 548/467; 548/483; 548/484; 548/486; 548/492; 548/525; 548/527; 549/54; 549/55; 549/56; 549/57; 549/466; 549/467; 549/468; 549/471

[58] Field of Search ............................. 549/466, 467, 549/468, 471, 54–57; 514/470, 422, 333, 469, 320, 337, 212, 443–445, 447–448, 324, 414–415, 418–419, 339, 323, 58; 546/284.1, 196, 284.4, 256, 284.7, 281.1, 202, 277.7, 278.1, 201; 548/525, 527, 467, 486, 483–484, 492; 540/602; 536/103

[56] References Cited

U.S. PATENT DOCUMENTS

| | | | |
|---|---|---|---|
| 4,800,211 | 1/1989 | Tischler et al. | 514/443 |
| 5,068,226 | 11/1991 | Weinshenker et al. | 514/58 |
| 5,118,680 | 6/1992 | Muller et al. | 514/233.5 |
| 5,576,343 | 11/1996 | Nagahara et al. | 514/422 |

FOREIGN PATENT DOCUMENTS

| | | |
|---|---|---|
| 0 655 439 A2 | 5/1995 | European Pat. Off. . |
| 94/08962 | 4/1994 | WIPO . |

OTHER PUBLICATIONS

*Journal of Medicinal Chemistry*, vol. 35, No. 23, Nov. 13, 1992.

*Primary Examiner*—Matthew V. Grumbling
*Assistant Examiner*—Brenda Coleman
*Attorney, Agent, or Firm*—Sughrue, Mion, Zinn, Macpeak & Seas

[57] ABSTRACT

A novel carboxylic acid compound having a condensed ring, which is represented by the formula (I)

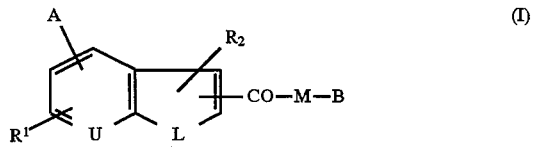

(I)

wherein each symbol is as defined in the specification, a pharmacologically acceptable salt thereof, a pharmaceutical composition thereof and pharmaceutical use thereof. The novel carboxylic acid compound having a condensed ring and pharmacologically acceptable salt thereof of the present invention have superior GPIIb/IIIa antagonism in mammals inclusive of human; can be administered orally; have long life in blood and low toxicity; and show less side-effects. Accordingly, they are extremely useful for the prophylaxis and treatment of thrombotic diseases and other diseases.

13 Claims, No Drawings

CARBOXYLIC ACID COMPOUND HAVING CONDENSED RING, SALT THEREOF AND PHARMACEUTICAL USE THEREOF

This application is a 371 PCT/JP95/01119 filed Jun. 6, 1995.

TECHNICAL FIELD

The present invention relates to novel carboxylic acid compounds having a condensed ring, pharmacologically acceptable salts thereof, pharmaceutical compositions thereof and pharmaceutical use thereof. More particularly, the present invention relates to novel carboxylic acid compounds having a condensed ring, which are useful for the prophylaxis and treatment of thrombotic diseases and the prophylaxis and treatment of the formation of thrombus during operation and extracorporeal circulation, pharmacologically acceptable salts thereof, pharmaceutical compositions thereof and pharmaceutical use thereof.

BACKGROUND ART

A platelet membrane glycoprotein GPIIb/IIIa (hereinafter abbreviated sa GPIIb/IIIa) belongs to the integrin family which is one of the receptor groups concerned with the adhesion between cells or between cell substrates, and forms a heterodimer on the platelet surface in the presence of $Ca^{++}$. It is also called $\alpha_{IIb}\beta_3$. By the adhesion of platelets to the injured site of a blood vessel and on stimulation by adenosine 5'-diphosphate (ADP) or thrombin, GPIIb/IIIa undergoes stereostructural changes and binds to a ligand having an RGD (arginine-glycine-aspartic acid) sequence, such as fibrinogen and von Willebrand's factor (GPIIb/IIIa does not bind to these ligands when it is not stimulated), as a result of which the final stage of the transmission of stimulation, namely, platelet aggregation, is induced. Therefore, a pharmaceutical agent (GPIIb/IIIa antagonist) which inhibits the binding of GPIIb/IIIa to these ligands can be a superior antiplatelet agent.

From this viewpoint, there have been already known [[4-[(p-amidino-N-methylbenzamide)acetyl]-o-phenylene] dioxy]diacetic acid (Ro 43-8857), [[1-[N-(p-amidinobenzoyl)-L-tyrosyl]-4-piperidinyl]oxy]-acetic acid (Ro 44-9883) (see Leo Alig et al., Journal of Medicinal Chemistry 1992, Vol. 35 (No.23), 4393–4407), N-(n-butanesulfonyl)-O-(4-(4-piperidinyl)-butyl-(S)-tyrosine (L-700,462; MK-383) (see G. D. Hartmans et al., Journal of Medicinal Chemistry 1992, Vol. 35 (No.24), 4640–4642), (3S, 5S)-5-(4'-amidino-4-biphenyl) oxymethyl-3-[(methoxycarbonyl)methyl]-2-pyrrolidinone (BIBU-52) (see Japanese Patent Unexamined Publication No. 264068/1992) and 4-amidino-4'-[(4-carboxycyclohexyl) aminocarbonyl]biphenyl hydrochloride (see Japanese Patent Unexamined Publication No. 334351/1992).

Yet, none of these are necessarily satisfactory in terms of, for example, efficacy, duration of efficacy, side-effects and possibility of oral administration.

Accordingly, an object of the present invention is to provide a novel compound having more superior GPIIb/IIIa-antagonistic action, a pharmaceutical composition thereof and a GPIIb/IIIa antagonist.

DISCLOSURE OF THE INVENTION

The present inventors have conducted various studies with the aim of achieving the above-mentioned objects and found that a carboxylic acid compound having a condensed ring, which has a specific structure, has superior GPIIb/IIIa-antagonistic action and low toxicity, which resulted in the completion of the present invention.

Accordingly, the present invention relates to a carboxylic acid compound having a condensed ring, which is represented by the formula (I)

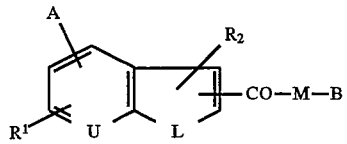

wherein

A is a group of the formula (1)

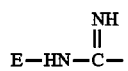

wherein E is hydrogen, alkyl or a protecting group for amidino, guanidino or amino, or a group of the formula (2)

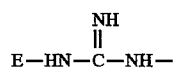

wherein E is as defined above;

B is a group of the formula (3)

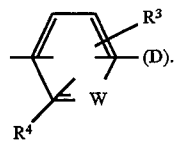

wherein D is a group of the formula (i)

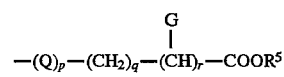

wherein $R^5$ is hydrogen, alkyl, cycloalkyl or aralkyl, Q is —O—, —S— or —$NR^6$— wherein $R^6$ is hydrogen, alkyl, cycloalkyl, aralkyl, alkylsulfonyl, aralkylsulfonyl, arylsulfonyl, acyl or —$(CH_2)_d$—$COOR^7$ wherein $R^7$ is hydrogen, alkyl, cycloalkyl or aralkyl and d is 1, 2 or 3, G is hydrogen, hydroxy, alkyl, cycloalkyl, phenyl, biphenylyl, pyridyl, aralkyl or $E^1$—$NR^8$— wherein $E^1$ is hydrogen, alkyl or a protecting group for amino and $R^8$ is hydrogen, alkyl, cycloalkyl or aralkyl, p and r are each independently 0 or 1 and q is 0, 1, 2 or 3, provided that when p≠0, at least one of q and r is not 0, W is =CH— or =N—, $R^3$ and $R^4$ may be the same or different and each is hydrogen, alkyl, halogen, acyl or alkoxy and e is 1 or 2, or a group of the formula (4)

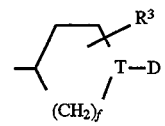

wherein T is —CH< or —N<, D is a group of the aforementioned formula (i), provided that when T is —N<, p is 0, R3 is as defined above and f is 1, 2 or 3;

L is —O—, —$NR^9$— wherein $R^9$ is hydrogen, alkyl, cycloalkyl, aralkyl or acyl, or —S—;

M is —$NR^{10}$— wherein $R^{10}$ is hydrogen, alkyl, cycloalkyl or aralkyl, —O— or —S—;

U is =CH— or =N—; and

R$^1$ and R$^2$ may be the same or different and each is a hydrogen, a hydroxy, an alkyl, a halogen, an amino, an acyl or an alkoxy, and pharmacologically acceptable salts thereof.

The present invention also relates to the above-mentioned carboxylic acid compound having a condensed ring of the formula (I) wherein B is a group of the formula (3) or (4) and, in D of the formula (i), p+q+r≦3, and pharmacologically acceptable salts thereof; the above-mentioned carboxylic acid compound having a condensed ring of the formula (I) wherein B is a group of the formula (3) and, in D of the formula (i), p+q+r=2, and pharmacologically acceptable salts thereof; the above-mentioned carboxylic acid compound having a condensed ring of the formula (I) wherein B is a group of the formula (4), f=2, and, in D of the formula (i), p+q+r=2, and pharmacologically acceptable salts thereof; and the above-mentioned carboxylic acid compound having a condensed ring of the formula (I) wherein L is —O—, and pharmacologically acceptable salts thereof.

The present invention further relates to an inclusion compound comprising a compound of the formula (I') [hereinafter also referred to as compound (I')]

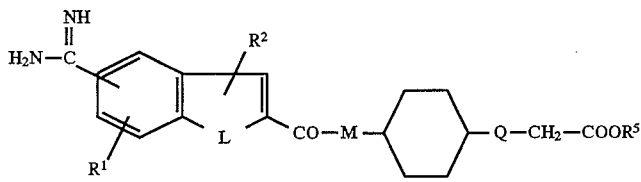

(I')

wherein

R$^5$ is a hydrogen, an alkyl, a cycloalkyl or an aralkyl;

Q is —O—, —S— or —NR$^6$— wherein R$^6$ is hydrogen, alkyl, cycloalkyl, aralkyl, alkylsulfonyl, aralkylsulfonyl, arylsulfonyl, acyl or —(CH$_2$)$_d$—COOR$^7$ wherein R$^7$ is hydrogen, alkyl, cycloalkyl or aralkyl, and d is 1, 2 or 3;

L is —O—, —NR$^9$— wherein R$^9$ is hydrogen, alkyl, cycloalkyl, aralkyl or acyl, or —S—;

M is —NR$^{10}$ wherein R$^{10}$ is hydrogen, alkyl, cycloalkyl or aralkyl, —O— or —S—; and R$^1$ and R$^2$ may be the same or different and each is a hydrogen, a hydroxy, an alkyl, a halogen, an amino, an acyl or an alkoxy, or a salt thereof, and cyclodextrin or a derivative thereof.

The present invention also relates to pharmaceutical compositions comprising s compound of the above formula (I) [hereinafter also referred to as compound (I)] or a pharmacologically acceptable salt thereof, pharmaceutical compositions comprising the above-mentioned inclusion compound, pharmaceutical use thereof, in particular, GPIIb/IIIa antagonists, and agents for the prophylaxis and treatment of the diseases caused by the formation of thrombus of platelets.

The respective symbols used in the present specification are explained in the following.

The alkyl at R$^1$–R$^{10}$, E, E$^1$ and G may be a linear or branched lower alkyl having 1 to 6 carbon atom. Examples thereof include methyl, ethyl, propyl, isopropyl, n-butyl, isobutyl, t-butyl, n-pentyl, n-hexyl, 2-methylpropyl, 1,1-dimethylpropyl and 1,2,2-trimethylpropyl, with preference given to methyl, ethyl, propyl, isopropyl and n-butyl. This alkyl may be substituted by hydroxy and the like.

The halogen at R$^1$–R$^4$ is fluorine, chlorine, bromine or iodine.

The acyl at R$^1$–R$^4$, R$^6$ and R$^9$ is exemplified by alkanoyl, aralkanoyl, aroyl and heteroarylcarbonyl. Specific examples of alkanoyl include linear or branched lower alkanoyl having 1 to 6 carbon atom, such as formyl, acetyl, propionyl, butyryl, valeryl, pivaloyl and hexanoyl. The alkanoyl moiety of the aralkanoyl is as mentioned above, and aralkanoyl is exemplified by phenylacetyl, 3-phenylpropionyl and 4-phenylbutyryl. Examples of aroyl include benzoyl, toluoyl, xyloyl, salicyloyl, cinnamoyl and naphthoyl. Examples of heteroarylcarbonyl include furoyl, nicotinoyl, isonicotinoyl and thenoyl, with preference given to acetyl, propionyl, butyryl, phenylacetyl, 3-phenylpropionyl, benzoyl and p-toluoyl.

The alkoxy at R$^1$–R$^4$ is a lower alkoxy having 1 to 6 carbon atoms, and may be linear or branched. Examples thereof are methoxy, ethoxy, propoxy, isopropoxy, n-butoxy, isobutoxy, t-butoxy, pentyloxy and hexyloxy. Of these, methoxy, ethoxy, propoxy and isopropoxy are preferable.

The cycloalkyl at R$^5$–R$^{10}$ and G is that preferably having 3 to 8 carbon atoms. Examples thereof include cyclopropyl, cyclobutyl, cyclopentyl, cyclohexyl, cycloheptyl and cyclooctyl. The cycloalkyl may be substituted by alkyl (same as the above-mentioned), hydroxyl, and the like.

The aralkyl at R$^5$–R$^{10}$ and G is an aralkyl wherein the alkyl moiety is the same as the above-mentioned. Examples of the aralkyl include benzyl, phenetyl, 3-phenylpropyl, 4-phenylbutyl, benzhydryl and trityl. The aralkyl may be substituted by, for example, alkyl (same as the above-mentioned), halogen (same as the above-mentioned), nitro, cyano and alkoxy (same as the above-mentioned).

With regard to the alkylsulfonyl at R$^6$, the alkyl moiety is the same as the above-mentioned. Examples of alkylsulfonyl are methylsulfonyl, ethylsulfonyl, propylsulfonyl, butylsulfonyl, pentylsulfonyl and hexylsulfonyl.

With regard to the aralkylsulfonyl at R$^6$, the aralkyl moiety is the same as the above-mentioned. Examples of aralkylsulfonyl are benzylsulfonyl, phenethylsulfonyl, 3-phenylpropylsulfonyl, 4-phenylbutylsulfonyl, benzhydrylsulfonyl and tritylsulfonyl.

With regard to the arylsulfonyl at R$^6$, the aryl moiety includes, for example, phenyl, tolyl, xylyl and naphthyl. Examples of arylsulfonyl are phenylsulfonyl and naphthylsulfonyl. The arylsulfonyl may be substituted by, for example, alkyl (same as the above-mentioned), halogen (same as the above-mentioned), nitro, cyano and alkoxy (same as the above-mentioned).

Phenyl, biphenylyl and pyridyl at G may be substituted by, for example, alkyl (same as the above-mentioned), halogen (same as the above-mentioned), nitro, cyano and alkoxy (same as the above-mentioned).

Examples of the protecting group for amidino, guanidino and amino at E and E$^1$ are optionally substituted aralkyl (e.g., benzyl, p-chlorobenzyl, p-fluorobenzyl, m-trifluoromethylbenzyl, phenethyl, 1-phenylethyl, benzhydryl and trityl), alkanoyl (e.g., formyl, acetyl, propionyl, butyryl, valeryl, pivaloyl and hexanoyl), haloalkanoyl (e.g., chloroacetyl and trifluoroacetyl), piperidinyloxyalkanoyl (e.g., 4-piperidinyloxyacetyl), alkenyloxycarbonyl (e.g., allyloxycarbonyl), alkoxycarbonyl (e.g., methoxycarbonyl, ethoxycarbonyl, t-butoxycarbonyl and hexyloxycarbonyl), acyloxyalkoxycarbonyl (e.g., acetoxymethyloxycarbonyl, (1-acetoxyethyl)oxycarbonyl, propionyloxymethyloxycarbonyl, pivaloyloxymethyloxycarbonyl, butyryloxymethyloxycarbonyl and isobutyryloxymethyloxycarbonyl), haloalkoxycarbonyl (e.g., chloromethoxycarbonyl and trichloroethoxycarbonyl), optionally substituted aroyl (e.g., benzoyl, toluoyl, xyloyl, naphthoyl and phthaloyl), optionally substituted phenylalkanoyl (e.g., phenylacetyl, 3-phenylpropionyl, 3-(p-methoxyphenyl) propionyl and 3-(p-chlorophenyl)propionyl), optionally substituted heteroarylcarbonyl (e.g., nicotinoyl, isonicotinoyl, 6-chloronicotinoyl, furoyl and thenoyl), heteroarylalkanoyl (e.g., thienylacetyl, imidazolylacetyl, furylacetyl, triazolylacetyl and thiadiazolylpropionyl), optionally substituted aryloxycarbonyl (e.g., phenoxycarbonyl and naphthyloxycarbonyl), optionally substituted phenoxyalkanoyl (e.g., phenoxyacetyl and phenoxypropionyl), optionally substituted arylglyoxyloyl (e.g., phenylglyoxyloyl and naphthylglyoxyloyl), optionally substituted phenylalkoxycarbonyl (e.g., benzyloxycarbonyl, phenethyloxycarbonyl, p-nitrobenzyloxycarbonyl and p-methoxybenzyloxycarbonyl), alkylsulfonyl (e.g., methylsulfonyl, ethylsulfonyl, propylsulfonyl, butylsulfonyl and penthylsulfonyl), haloalkylsulfonyl (e.g., trifluoromethylsulfonyl), optionally substituted aralkylsulfonyl (e.g., benzylsulfonyl, p-chlorobenzylsulfonyl, phenethylsulfonyl and benzhydrylsulfonyl), and optionally substituted arylsulfonyl (e.g., phenylsulfonyl, p-chlorophenylsulfonyl, tolylsulfonyl, xylylsulfonyl and naphthylsulfonyl).

The alkyl moiety, alkanoyl moiety, alkoxy moiety and acyl moiety in said respective groups are exemplified by those having 1 to 6 carbon atoms, and alkenyl moiety is exemplified by those having 2 to 6 carbon atoms.

Preferred are, for example, phenylalkoxycarbonyl, alkoxycarbonyl, acyloxyalkoxycarbonyl, alkanoyl, phenylalkanoyl, haloalkanoyl, aralkyl, alkylsulfonyl, aralkylsulfonyl and arylsulfonyl. More preferred are, for example, benzyloxycarbonyl, t-butoxycarbonyl, acetoxymethyloxycarbonyl, pivaloyloxymethyloxycarbonyl, n-valeryl, n-hexanoyl, 3-phenylpropionyl, trifluoroacetyl, benzyl, phenetyl, trityl, n-butylsulfonyl, n-hexylsulfonyl, benzylsulfonyl, phenylsulfonyl and p-tolylsulfonyl.

Examples of the substituent of the optionally substituted aralkyl, aloyl, phenylalkanoyl, heteroarylcarbonyl, aryloxycarbonyl, phenoxyalkanoyl, arylglyoxyloyl, phenylalkoxycarbonyl, aralkylsulfonyl, arylsulfonyl include nitro, trifluoromethyl, alkyl (same as the above-mentioned), phenyl, alkoxy (same as the above-mentioned), halogen (same as the above-mentioned) and alkanoyl (same as the above-mentioned).

The pharmacologically acceptable salts of compound (I) include inorganic acid addition salt (e.g., salt with hydrochloric acid, hydrobromic acid, hydroiodic acid, sulfuric acid and phosphoric acid), salt with amino acid (e.g., salt with glutamic acid and aspartic acid), and organic acid addition salt (e.g., salt with methanesulfonic acid, bonzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid and malic acid).

Examples of the pharmacologically acceptable salt when compound (I) has a free carboxylic group include alkali metal salts (e.g., salt with sodium or potassium), alkaline earth metal salts (e.g., salt with calcium or magnesium), salts with organic base (e.g., salt with methylamine, trimethylamine, ethylamine, diethylamine, triethylamine, dicyclohexylamine, pyridine, picoline or ethylenediamine) and ammonium salt.

When compound (I) or salt thereof has various isomers (e.g., cis compound, trans compound and optical isomers based on asymmetric carbon), they are all encompassed in the present invention.

Of the compounds (I) of the present invention, a compound of the formula (I) wherein B is a group of the formula (3) or (4) and, in D of the formula (i), p+q+r<3 is preferable.

Also, a compound of the formula (I) wherein B is a group of the formula (3) and, in D of the formula (i), p+q+r=2 is preferable, and a compound of the formula (I) wherein B is a group of the formula (4), f=2, and, in D of the formula (i), p+q+r=2 is more preferable.

Moreover, a compound of the formula (I) wherein L is —O— is preferable.

In addition, a compound of the formula (I) wherein M is —NR$^{10}$— is wherein R$^{10}$ is as defined above, or —O— is preferable.

While the binding site of the respective substituents in the formula (I) is not particularly limited, the group of the formula —CO—M—B preferably binds at 2-position relative to L, and the group A preferably binds at 5-position or 6-position relative to L.

Said compound (I) can be synthesized by, for example, the method shown below.

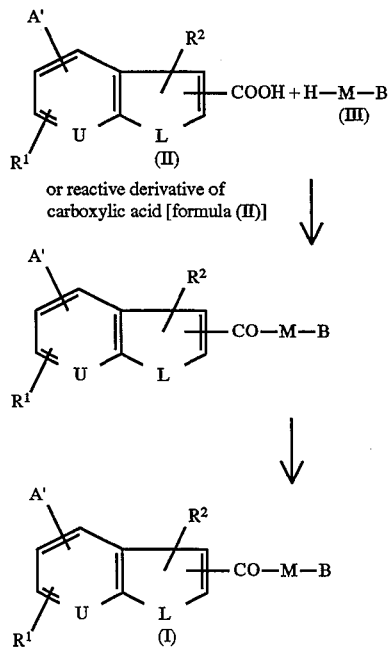

wherein A' is the same as the above-mentioned A, or halogen, cyano, or optionally protected amino, and other symbols are as defined above.

That is, compound (I) can be synthesized directly or via a precursor thereof by condensation reaction of carboxylic acid of the formula (II) [hereinafter also referred to as carboxylic acid (II)] or a reactive derivative of this carboxylic acid (II), with a compound of the formula (III) [hereinafter also referred to as compound (III)].

The amounts of carboxylic acid (II) or its reactive derivative and compound (III) to be charged may be generally equimolar amounts. Where necessary, either of them may be used in 1.1- to 3-fold amount based on the other.

When the carboxylic acid (II) is used as it is, the reaction is carried out in the presence of a condensing agent such as 2-chloro-4,6-dimethoxy-1,3,5-triazine, o-benzotriazol-1-yl-N,N,N',N'-tetramethyluronium hexafluorophosphate, PyBOP (benzotriazol-1-yl-oxy-tris (pyrrolidino) phosphonium hexafluorophosphate), BOP (benzotriazol-1-yl-oxy-tris (dimethylamino)phosphonium hexafluorophosphate), PyBroP (bromo-tris (pyrrolidino) phosphonium hexafluorophosphate), N,N-dicyclohexylcarbodiimide, N,N-diisopropylcarbodiimide, 1-(3-dimethylaminopropyl)-3-ethylcarbodiimide methiodide, 1-ethyl-3-(3-dimethylaminopropyl) carbodiimide hydrochloride and N-cyclohexyl-N'-(2-morpholinoethyl)carbodiimide metho-p-toluenesulfonate.

The carboxylic acid (II) may be converted to a reactive derivative such as acid anhydride, activated ester and acid halide by a conventional method before use.

Examples of the acid anhydride include anhydride with pivalic acid and anhydride with isobutyl carbonate. As the actived ester, usable are, for example, p-nitrophenyl ester, 2,4,5-trichlorophenyl ester, N-hydroxysuccinimide ester, N-hydroxyphthalimide ester and N-hydroxy-5-norbornene-2,3-dicarboxyimide ester. As the acid halide, for example, carboxylic acid chloride and carboxylic acid bromide are used.

In compound (III), the group B therein includes free carboxylic acid and ester thereof. When compound (III) is reacted with carboxylic acid (II) using a condensing agent, an ester is preferable.

Examples of the reaction solvent in every case include N,N-dimethylformamide, N,N-dimethylacetamide, dimethyl sulfoxide, hexamethylphosphoric triamide, pyridine, dioxane, tetrahydrofuran, acetonitrile, chloroform, methylene chloride, dimethoxyethane, benzene, ethyl acetate, sulfolane and mixed solvents thereof. Preferable solvent includes, for example, N,N-dimethylformamide, methylene chloride, tetrahydrofuran and acetonitrile.

The reaction temperature is generally about 0° C.–100° C. and the reaction time is from several hours to 3 days.

When a condensing agent or an activated ester of carboxylic acid (II) is used in the above reaction, a reaction co-agent such as N-methylmorpholine, 1-hydroxybenzotriazole and 4-dimethylaminopyridine can be used.

When an acid anhydride of carboxylic acid (II) is used, a reaction co-agent such as 4-dimethylaminopyridine and 1-hydroxybenzotriazole can be used.

When an acid halide of carboxylic acid (II) is used, the reaction is preferably carried out in the presence of a halogenated hydrogen trapping agent such as triethylamine, pyridine, picoline and sodium hydrogencarbonate.

Halogen, cyano and optionally protected amino which is represented by A' in carboxylic acid (II) or a reactive derivative thereof is converted to amidino, guanidino, protected amidino or protected guanidino which is A in the formula (I).

The protecting group for the aforesaid amidino, guanidino or amino is as mentioned above. The protecting group for amidino, guanidino or amino can be eliminated as necessary. The method for deprotection includes, for example, hydrogenation, acid decomposition, base decomposition and hydrolysis, which are carried out by a conventional method.

The method for converting the above-mentioned A' to A in the stage of a product obtained by the reaction of carboxylic acid (II) or its reactive derivative, with compound (III), or in the stage before the reaction, namely, in the stage of carboxylic acid (II) is described in the following. In the latter case, the conversion can be done with regard to carboxylic acid (II) itself or after a conversion to an alkyl ester compound thereof for protecting said carboxyl group. After the converted amidino or guanidino is protected as necessary, or, when the compound has been converted to an alkyl ester compound thereof for the protection of the carboxyl group, after a conversion to carboxylic acid (II), the compound is subjected to the reaction with compound (III). The carboxylic acid (II) may be converted to its reactive derivative thereof as necessary, and subjected to the reaction with compound (III), as mentioned above.

Method 1

This method relates to the conversion of halogen, amino or cyano of A' to amidino of A.

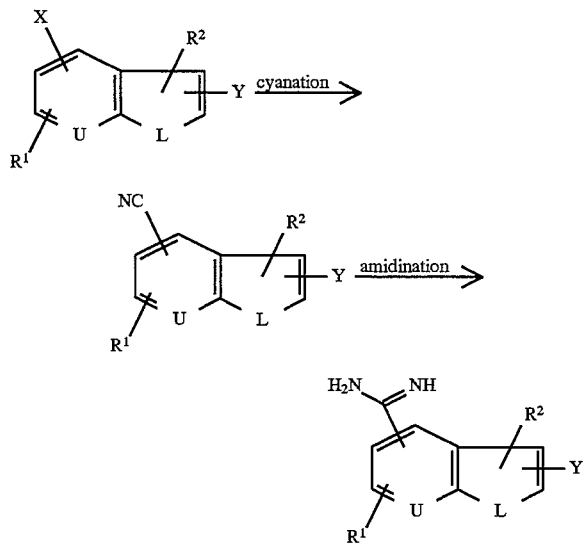

wherein X is halogen (same as the above-mentioned) or amino; Y is a group of the formula (ii)

$$-CO-M-B \quad \text{(ii)}$$

wherein B and M are as defined above, or a group of the formula (iii)

$$-COOR^{11} \quad \text{(iii)}$$

wherein $R^{11}$ is hydrogen or alkyl (same as the above-mentioned) and other symbols are as defined above.

Cyanation is explained in the following.

When X is halogen in the above formula, a nitrile compound is obtained by substitution with a metallic cyanide compound.

Examples of the metallic cyanide compound include copper (I) cyanide, potassium cyanide and sodium cyanide. The reaction solvent is exemplified by 1,3-dimethyl-2-imidazolidinone, N,N-dimethylformamide an N-methyl-2-pyrrolidone. The reaction temperature is from room temperature to about 250° C. and the reaction time is from several hours to 3 days, with preference given to a reaction at about 80° C.–230° C. for several hours to one day.

When X is amino, conversion to cyanide is done by Sandmeyer reaction. A salt (e.g., hydrochloride and sulfate) of the starting amine compound is diazotized with sodium nitrite to give a diazonium salt, which is added with a metallic cyanide compound to give a nitrile compound.

Examples of the preferable metallic cyanide compound include copper (I) cyanide, potassium cyanide and sodium cyanide. In addition, a complex of potassium cyanide and nickel cyanide, nickel sulfate, nickel chloride and the like can be also used. While the reaction solvent is preferably water, tetrahydrofuran, dioxane, ethanol and the like may be used along with water where necessary. For preventing generation of hydrogen cyanide, sodium carbonate is added for neutralization before the addition of a metallic cyanide compound or a sodium carbonate buffer of a metallic cyanide compound is used. The reaction temperature is not more than room temperature, preferably under ice-cooling, and the reaction time is about 0.5–5 hours. Ultimately, heating at about 40° C.–60° C. for about 0.5–1 hour terminates the reaction.

Now, amidination is explained. This reaction can be carried out by a known method via an imidate compound or a thiocarbamoyl compound (see Organic Functional Group Preparations, III, Academic, Chapter 6 or Leo Alig et al., Journal of Medicinal Chemistry 1992, Vol. 35 (No. 23), 4393–4407).

A method via an imidate compound comprises reacting an equivalent to large excess alcohol such as methanol, ethanol, propanol and butanol with a nitrile compound in the presence of a hydrogen halide such as hydrogen chloride and hydrogen bromide to give an imidate compound. Where necessary, an aliphatic ether (e.g., diethyl ether), hydrocarbon halide (e.g., chloroform and methylene chloride) or an aprotic solvent (e.g., benzene) may be used. The reaction temperature is about −10° C. to +30° C. and the reaction time is from several hours to 2 days, with preference given to a reaction from under ice-cooling to room temperature for about 8–15 hours.

The obtained imidate compound is reacted with ammonia to give an amidine compound. A solvent such as alcohol (e.g., methanol, ethanol and propanol), aliphatic ether (e.g., diethyl ether), hydrocarbon halide (e.g., chloroform and methylene chloride), an aprotic solvent (e.g., benzene), N,N-dimethylformamide and dimethyl sulfoxide is used. Ammonium chloride is preferably present in this reaction with ammonia. The reaction temperature is about −10° C.–+100° C. and the reaction time is from several hours to 20 hours. A reaction in methanol, ethanol or propanol at about 50° C.–80° C. for several hours is preferable.

A method via a thiocarbamoyl compound comprises reacting hydrogen sulfide with a nitrile compound in a solvent such as pyridine, triethylamine, N,N-dimethylformamide or a mixed solvent thereof to give a thiocarbamoyl compound. The reaction temperature is from under ice-cooling to room temperature and the reaction time is from about 5 hours to one day, with preference given to a reaction at room temperature for about 10–20 hours.

The obtained thiocarbamoyl compound is reacted with an alkyl halide such as methyl iodide and ethyl bromide in a solvent such as acetone, dioxane and tetrahydrofuran. The reaction temperature is about 50° C.–100° C. and the reaction time is abut 0.5–10 hours. The intermediate obtained here is, with or without isolation, reacted with ammonia or an ammonia derivative such as ammonium acetate and ammonium chloride to give an amidine compound. A solvent such as alcohol (e.g., methanol, ethanol and propanol) and N,N-dimethylformamide is used. Preferably, the compound is reacted with ammonium acetate in a solvent of methanol or ethanol. The reaction temperature is about 50° C.–100° C. and the reaction time is about several hours to 10 hours.

Method 2

This method is a conversion of an optionally protected amino of A' to guanidino of A.

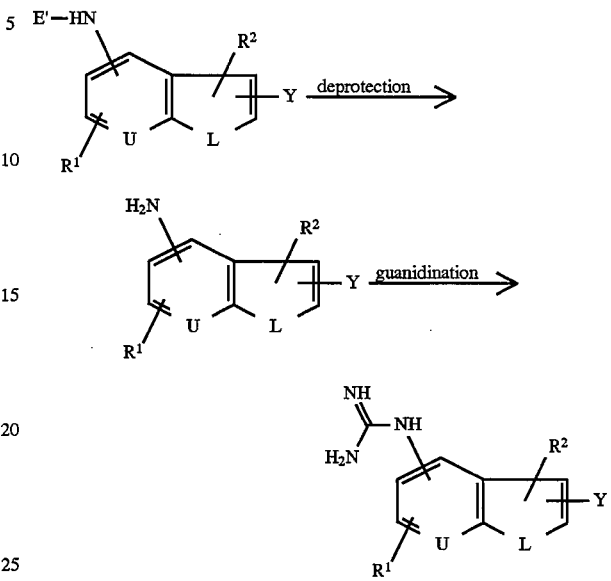

wherein E' is an amino-protecting group (same as the above mentioned) and other symbols are as defined above.

The deprotection of the amino-protecting group can be carried out by a conventional method as mentioned above.

The conversion to guanidino can be carried out according to a known method using cyanamide, formamidinesulfinic acid or aminoiminomethanesulfonic acid (see T. Nakayama et al., Chem. Pharm. Bull. Vol. 41(1), 117–125 (1993) or A. E. Miller et al., Synthesis 1986, 777–779).

For example, when a salt (e.g., hydrochloride and sulfate) of the starting material amine compound is reacted with cyanamide to give a guadinino compound, an alcohol such as methanol and ethanol is used as a solvent. The reaction temperature is about 60°–80° C. and the reaction time is from several hours to one day.

In the above production method, protection and deprotection of amino group, esterification of carboxylic acid and hydrolysis of ester can be performed as necessary by a conventional method.

The starting material carboxylic acid (II) and its reactive derivative and compound (III) can be produced by a method conventionally known. A particularly useful starting compound such as benzofurancarboxylic acid, indolecarboxylic acid and benzo[b]thiophenecarboxylic acid, all having a cyano group in the phenyl nucleus, as well as furo[2,3-b]pyridinecarboxylic acid having a cyano group in the pyridine nucleus can be synthesized according to the method described in literatures [see O. Dann et al., Liebigs Ann. Chem. 1982, 1836–1869, O. Dann et al., Liebigs Ann. Chem. 1986, 438–455, A. J. Bridges et al., Tetrahedron Letters, Vol. 33 (No.49), 7499–7502 (1992), J. Heterocyclic Chem., Vol. 3, 202–205, Japanese Patent Unexamined Publication No. 208946/1993].

The compound (I) of the present invention thus synthesized can be obtained at an optional purity by appropriately applying a known method for separation and purification, such as concentration, extraction, chromatography, reprecipitation and recrystallization.

The pharmacologically acceptable salt of said compound (I) can be also produced by a known method. Various isomers of said compound (I) can be produced by a known method.

Specific examples of the compound (I) of the present invention are shown in the following Tables 1–14 and Tables 15–18, to which the compounds of the present invention are not limited.

In the Tables, $E_1$ means acetoxymethyloxycarbonyl, $E_2$ means allyloxycarbonyl, $E_3$ means (1-acetoxyethyl) oxycarbonyl, $E_4$ means methoxycarbonyl, $E_5$ means pivaloyloxymethyloxycarbonyl, $E_6$ means n-butyryloxymethyloxycarbonyl, Z means benzyloxycarbonyl, Boc means t-butoxycarbonyl, Me means methyl, Et means ethyl, isoPr means isopropyl, nBu means n-butyl, tBu means t-butyl, nPen means n-pentyl, nHex means n-hexyl, c.Hex means cyclohexyl, Ac means acetyl, Bn means benzyl, and (S) and (R) mean absolute configurations. In the Tables, $R^7$ in $B_{48}$, and $B_{49}$ is the same group as $R^5$.

TABLE 1

| Compound No. | A (binding site) | L | binding site of CO | $R^1$ | $R^2$ | M | B | $R^5$ |
|---|---|---|---|---|---|---|---|---|
| 1 | Bn—HN(HN=)C— (5) | O | 2 | H | H | NH | $B_1$ | Et |
| 2 | Z—HN(HN=)C— (5) | O | 2 | H | H | NH | $B_1$ | Et |
| 3 | $E_1$—HN(HN=)C— (5) | O | 2 | H | H | NH | $B_1$ | H |
| 4 | Z—HN(HN=)C— (5) | O | 2 | H | H | NH | $B_1$ | H |
| 5 | Bn—HN(HN=)C— (5) | O | 2 | H | H | NH | $B_1$ | H |
| 6 | $H_2N(HN=)C—$ (5) | O | 2 | H | H | NH | $B_1$ | Me |
| 7 | $H_2N(HN=)C—$ (5) | O | 2 | H | H | NH | $B_1$ | Et |
| 8 | $H_2N(HN=)C—$ (5) | O | 2 | H | H | NH | $B_1$ | tBu |
| 9 | $H_2N(HN=)C—$ (6) | O | 2 | H | H | NH | $B_1$ | tBu |
| 10 | $H_2N(HN=)C—$ (5) | O | 2 | H | H | NH | $B_1$ | H |
| 11 | $H_2N(HN=)C—$ (5) | O | 3 | H | H | NH | $B_1$ | H |
| 12 | $H_2N(HN=)C—$ (6) | O | 2 | H | H | NH | $B_1$ | H |
| 13 | $H_2N(HN=)C—$ (5) | O | 2 | H | 3-Me | NH | $B_1$ | tBu |
| 14 | $H_2N(HN=)C—$ (5) | O | 2 | H | 3-Cl | NH | $B_1$ | H |
| 15 | $H_2N(HN=)C—$ (5) | O | 2 | H | 3-OH | NH | $B_1$ | H |
| 16 | $H_2N(HN=)C—$ (5) | O | 2 | H | 3-Me | NH | $B_1$ | H |
| 17 | $H_2N(HN=)C—$ (5) | O | 2 | H | 3-OMe | NH | $B_1$ | H |
| 18 | $H_2N(HN=)C—$ (5) | O | 2 | 7-Cl | H | NH | $B_1$ | H |
| 19 | $H_2N(HN=)C—$ (5) | O | 2 | 7-OMe | H | NH | $B_1$ | H |
| 20 | $H_2N(HN=)C—$ (5) | O | 2 | H | H | N-Me | $B_1$ | tBu |

TABLE 2

| Compound No. | A (binding site) | L | binding site of CO | $R^1$ | $R^2$ | M | B | $R^5$ |
|---|---|---|---|---|---|---|---|---|
| 21 | $H_2N(HN=)C—$ (5) | O | 2 | H | H | N-Me | $B_1$ | H |
| 22 | $H_2N(HN=)C—$ (5) | O | 2 | H | H | N-Pr | $B_1$ | H |
| 23 | $H_2N(HN=)C—$ (5) | O | 2 | H | H | NH | $B_2$ | H |
| 24 | $H_2N(HN=)C—$ (5) | O | 2 | H | H | NH | $B_3$ | H |
| 25 | $H_2N(HN=)C—$ (5) | O | 2 | H | H | NH | $B_4$ | H |
| 26 | Bn—HN(HN=)C— (5) | O | 2 | H | H | NH | $B_5$ | H |
| 27 | $H_2N(HN=)C—$ (5) | O | 2 | H | H | NH | $B_5$ | Et |
| 28 | $H_2N(HN=)C—$ (5) | O | 2 | H | H | NH | $B_5$ | tBu |
| 29 | $H_2N(HN=)C—$ (5) | O | 2 | H | H | NH | $B_5$ | H |
| 30 | $H_2N(HN=)C—$ (6) | O | 2 | H | H | NH | $B_5$ | H |
| 31 | $H_2N(HN=)C—$ (5) | O | 2 | 7-Me | H | NH | $B_5$ | H |
| 32 | $H_2N(HN=)C—$ (5) | O | 2 | 7-OMe | H | NH | $B_5$ | H |
| 33 | $E_2$—HN(HN=)C— (5) | O | 2 | H | H | NH | $B_6$ | H |
| 34 | Bn—HN(HN=)C— (5) | O | 2 | H | H | NH | $B_6$ | H |
| 35 | $H_2N(HN=)C—$ (5) | O | 2 | H | H | NH | $B_6$ | Me |
| 36 | $H_2N(HN=)C—$ (5) | O | 2 | H | H | NH | $B_6$ | Bn |
| 37 | $H_2N(HN=)C—$ (5) | O | 2 | H | H | NH | $B_6$ | H |
| 38 | $H_2N(HN=)C—$ (6) | O | 2 | H | H | NH | $B_6$ | H |

TABLE 2-continued $$\text{structure with A at 4/5, R}^1 \text{ at 6/7, L}_1 \text{ at position 1, R}^2 \text{ at 3, CO-M-B at 2}$$

| Compound No. | A (binding site) | L | binding site of CO | $R^1$ | $R^2$ | M | B | $R^5$ |
|---|---|---|---|---|---|---|---|---|
| 39 | $H_2N(HN=)C-$ (5) | O | 2 | 7-OAc | H | NH | $B_6$ | H |
| 40 | $H_2N(HN=)C-$ (5) | O | 2 | H | H | NH | $B_7$ | Me |

TABLE 3

| Compound No. | A (binding site) | L | binding site of CO | $R^1$ | $R^2$ | M | B | $R^5$ |
|---|---|---|---|---|---|---|---|---|
| 41 | $H_2N(HN=)C-$ (5) | O | 2 | H | H | NH | $B_7(S)$ | Et |
| 42 | $H_2N(HN=)C-$ (5) | O | 2 | H | H | NH | $B_{22}(S)$ | Et |
| 43 | $H_2N(HN=)C-$ (5) | O | 2 | H | H | NH | $B_9(S)$ | Et |
| 44 | $H_2N(HN=)C-$ (5) | O | 2 | H | H | NH | $B_{10}(S)$ | Et |
| 45 | $H_2N(HN=)C-$ (5) | O | 2 | H | H | NH | $B_{11}(S)$ | Et |
| 46 | $H_2N(HN=)C-$ (5) | O | 2 | H | H | NH | $B_{11}(S)$ | H |
| 47 | $H_2N(HN=)C-$ (5) | O | 2 | H | H | NH | $B_8(S)$ | H |
| 48 | $H_2N(HN=)C-$ (5) | O | 2 | H | H | NH | $B_7$ | H |
| 49 | $H_2N(HN=)C-$ (5) | O | 2 | H | H | NH | $B_7(S)$ | H |
| 50 | $H_2N(HN=)C-$ (5) | O | 2 | H | H | NH | $B_7(R)$ | H |
| 51 | $H_2N(HN=)C-$ (5) | O | 2 | H | H | NH | $B_{12}$ | H |
| 52 | $H_2N(HN=)C-$ (5) | O | 2 | H | H | NH | $B_{13}$ | H |
| 53 | $H_2N(HN=)C-$ (5) | O | 2 | H | H | NH | $B_{14}$ | H |
| 54 | $H_2N(HN=)C-$ (5) | O | 2 | H | H | NH | $B_{15}(S)$ | Et |
| 55 | $H_2N(HN=)C-$ (5) | O | 2 | H | H | NH | $B_{15}(S)$ | H |
| 56 | $H_2N(HN=)C-$ (5) | O | 2 | H | H | NH | $B_{10}(S)$ | H |
| 57 | $H_2N(HN=)C-$ (5) | O | 2 | H | H | NH | $B_{16}$ | H |
| 58 | $H_2N(HN=)C-$ (5) | O | 2 | H | H | NH | $B_{17}(S)$ | H |
| 59 | $H_2N(HN=)C-$ (5) | O | 2 | H | H | NH | $B_{18}$ | H |
| 60 | $H_2N(HN=)C-$ (5) | O | 2 | H | H | NH | $B_{19}$ | H |
| 61 | $H_2N(HN=)C-$ (5) | O | 2 | H | H | NH | $B_9(S)$ | H |

TABLE 4

| Compound No. | A (binding site) | L | binding site of CO | $R^1$ | $R^2$ | M | B | $R^5$ |
|---|---|---|---|---|---|---|---|---|
| 62 | $H_2N(HN=)C-$ (5) | O | 2 | H | H | NH | $B_{20}$ | H |
| 63 | $H_2N(HN=)C-$ (5) | O | 2 | H | H | NH | $B_{21}$ | H |
| 64 | $H_2N(HN=)C-$ (5) | O | 2 | H | H | NH | $B_{22}$ | H |
| 65 | $H_2N(HN=)C-$ (5) | O | 2 | H | H | NH | $B_{23}$ | H |
| 66 | $H_2N(HN=)C-$ (5) | O | 2 | H | H | NH | $B_{24}$ | H |
| 67 | $H_2N(HN=)C-$ (5) | O | 2 | H | H | NH | $B_{25}$ | H |
| 68 | $H_2N(HN=)C-$ (5) | O | 2 | H | H | NH | $B_{26}$ | Et |
| 69 | $Z-HN(HN=)C-$ (5) | O | 2 | H | H | NH | $B_{27}$ | Et |
| 70 | $H_2N(HN=)C-$ (5) | O | 2 | H | H | NH | $B_{28}$ | H |
| 71 | $H_2N(HN=)C-$ (5) | O | 2 | H | H | NH | $B_{29}$ | H |
| 72 | $H_2N(HN=)C-$ (5) | O | 2 | H | H | NH | $B_{30}$ | H |

TABLE 4-continued

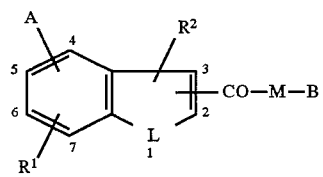

| Compound No. | A (binding site) | L | binding site of CO | $R^1$ | $R^2$ | M | B | $R^5$ |
|---|---|---|---|---|---|---|---|---|
| 73 | $H_2N(HN=)C-$ (5) | O | 2 | H | H | NH | $B_{31}$ | H |
| 74 | $H_2N(HN=)C-$ (5) | O | 2 | H | H | NH | $B_{26}$ | H |
| 75 | $H_2N(HN=)C-$ (5) | O | 2 | H | H | NH | $B_{32}$ | H |
| 76 | $E_3-HN(HN=)C-$ (5) | O | 2 | H | H | O | $B_1$ | Et |
| 77 | $H_2N(HN=)C-$ (5) | O | 2 | H | H | O | $B_1$ | Et |
| 78 | $H_2N(HN=)C-$ (5) | O | 2 | H | H | O | $B_1$ | H |
| 79 | $H_2N(HN=)C-$ (5) | O | 2 | H | H | O | $B_5$ | Et |
| 80 | $H_2N(HN=)C-$ (5) | O | 2 | H | H | O | $B_5$ | H |
| 81 | $H_2N(HN=)C-$ (5) | O | 2 | H | H | O | $B_6$ | H |

TABLE 5

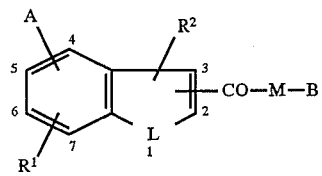

| Compound No. | A (binding site) | L | binding site of CO | $R^1$ | $R^2$ | M | B | $R^5$ |
|---|---|---|---|---|---|---|---|---|
| 82 | $H_2N(HN=)C-$ (5) | O | 2 | H | H | O | $B_7(S)$ | H |
| 83 | $H_2N(HN=)C-NH-$ (5) | O | 2 | H | H | NH | $B_1$ | tBu |
| 84 | $H_2N(HN=)C-NH-$ (5) | O | 2 | H | H | NH | $B_1$ | H |
| 85 | $H_2N(HN=)C-NH-$ (6) | O | 2 | H | H | NH | $B_1$ | H |
| 86 | $E_1-HN(HN=)C-NH-$ (5) | O | 2 | H | H | NH | $B_5$ | Et |
| 87 | $H_2N(HN=)C-NH-$ (5) | O | 2 | H | H | NH | $B_5$ | H |
| 88 | $H_2N(HN=)C-NH-$ (5) | O | 2 | H | H | NH | $B_6$ | H |
| 89 | $H_2N(HN=)C-NH-$ (5) | O | 2 | H | H | NH | $B_7$ | H |
| 90 | $E_4-HN(HN=)C-$ (5) | NH | 2 | H | H | NH | $B_1$ | Et |
| 91 | $E_5-HN(HN=)C-$ (6) | NH | 2 | H | H | NH | $B_1$ | Et |
| 92 | $H_2N(HN=)C-$ (6) | NH | 2 | H | H | NH | $B_1$ | Et |
| 93 | $H_2N(HN=)C-$ (6) | NH | 2 | H | H | NH | $B_1$ | tBu |
| 94 | $H_2N(HN=)C-$ (6) | NH | 2 | H | H | NH | $B_1$ | c.Hex |
| 95 | $H_2N(HN=)C-$ (6) | NH | 2 | H | H | NH | $B_1$ | H |
| 96 | $H_2N(HN=)C-$ (6) | NH | 3 | H | H | NH | $B_1$ | H |
| 97 | $H_2N(HN=)C-$ (6) | NH | 2 | H | 3-Me | NH | $B_1$ | Et |
| 98 | $H_2N(HN=)C-$ (6) | NH | 2 | H | 3-Cl | NH | $B_1$ | H |
| 99 | $H_2N(HN=)C-$ (6) | NH | 2 | H | 3-Me | NH | $B_1$ | H |
| 100 | $H_2N(HN=)C-$ (6) | NH | 2 | H | H | NH | $B_5$ | Et |
| 101 | $H_2N(HN=)C-$ (6) | NH | 2 | H | H | NH | $B_5$ | H |

TABLE 6

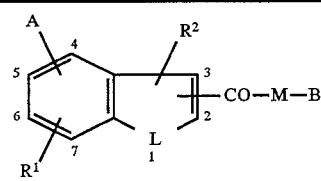

| Compound No. | A (binding site) | L | binding site of CO | $R^1$ | $R^2$ | M | B | $R^5$ |
|---|---|---|---|---|---|---|---|---|
| 102 | $H_2N(HN=)C-$ (6) | NH | 2 | H | H | NH | $B_6$ | Bn |
| 103 | $H_2N(HN=)C-$ (6) | NH | 2 | H | H | NH | $B_6$ | H |
| 104 | $H_2N(HN=)C-$ (6) | NH | 2 | H | 3-Cl | NH | $B_6$ | H |
| 105 | $Bn-HN(HN=)C-$ (6) | NH | 2 | H | H | NH | $B_7$ | H |

TABLE 6-continued

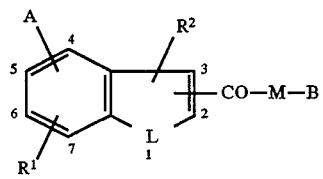

| Compound No. | A (binding site) | L | binding site of CO | $R^1$ | $R^2$ | M | B | $R^5$ |
|---|---|---|---|---|---|---|---|---|
| 106 | $H_2N(HN=)C-$ (6) | NH | 2 | H | H | NH | $B_7$ | Me |
| 107 | $H_2N(HN=)C-$ (6) | NH | 2 | H | H | NH | $B_7(S)$ | H |
| 108 | $H_2N(HN=)C-$ (6) | NH | 2 | H | 3-Me | NH | $B_7$ | H |
| 109 | $H_2N(HN=)C-$ (6) | NH | 2 | H | H | NH | $B_{12}(S)$ | H |
| 110 | $H_2N(HN=)C-$ (6) | NH | 2 | H | H | NH | $B_{17}$ | H |
| 111 | $H_2N(HN=)C-$ (6) | NH | 2 | H | H | NH | $B_{33}$ | H |
| 112 | $H_2N(HN=)C-$ (6) | NH | 2 | H | H | O | $B_1$ | H |
| 113 | $H_2N(HN=)C-NH-$ (5) | NH | 2 | H | H | NH | $B_1$ | H |
| 114 | $H_2N(HN=)C-NH-$ (6) | NH | 2 | H | H | NH | $B_5$ | H |
| 115 | $H_2N(HN=)C-NH-$ (5) | NH | 2 | H | H | NH | $B_6$ | H |
| 116 | $Boc-HN(HN=)C-$ (5) | N-Me | 2 | H | H | NH | $B_1$ | Et |
| 117 | $H_2N(HN=)C-$ (6) | N-Me | 2 | H | H | NH | $B_1$ | tBu |
| 118 | $H_2N(HN=)C-$ (6) | N-Me | 2 | H | H | NH | $B_1$ | H |
| 119 | $H_2N(HN=)C-$ (6) | N-Me | 2 | H | 3-Cl | NH | $B_1$ | H |
| 120 | $H_2N(HN=)C-$ (6) | N-Me | 2 | H | 3-Me | NH | $B_1$ | H |
| 121 | $H_2N(HN=)C-$ (6) | N-Me | 2 | H | 3-OAc | NH | $B_1$ | H |

TABLE 7

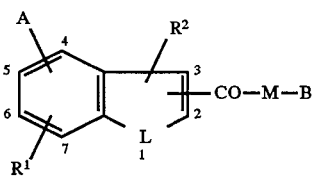

| Compound No. | A (binding site) | L | binding site of CO | $R^1$ | $R^2$ | M | B | $R^5$ |
|---|---|---|---|---|---|---|---|---|
| 122 | $H_2N(HN=)C-$ (5) | N-Me | 2 | H | H | NH | $B_5$ | H |
| 123 | $H_2N(HN=)C-$ (6) | N-Me | 2 | H | H | NH | $B_5$ | H |
| 124 | $H_2N(HN=)C-$ (6) | N-Me | 2 | H | H | NH | $B_6$ | H |
| 125 | $H_2N(HN=)C-$ (6) | N-Me | 2 | H | H | NH | $B_7$ | Me |
| 126 | $H_2N(HN=)C-NH-$ (6) | N-Me | 2 | H | H | NH | $B_1$ | H |
| 127 | $H_2N(HN=)C-NH-$ (5) | N-Me | 2 | H | H | NH | $B_5$ | H |
| 128 | $H_2N(HN=)C-NH-$ (6) | N-Me | 2 | H | H | NH | $B_6$ | H |
| 129 | $H_2N(HN=)C-NH-$ (6) | N-Me | 2 | H | H | NH | $B_7$ | H |
| 130 | $E_6-HN(HN=)C-$ (5) | S | 2 | H | H | NH | $B_1$ | H |
| 131 | $H_2N(HN=)C-$ (5) | S | 2 | H | H | NH | $B_1$ | tBu |
| 132 | $H_2N(HN=)C-$ (6) | S | 2 | H | H | NH | $B_1$ | tBu |
| 133 | $H_2N(HN=)C-$ (6) | S | 2 | H | H | NH | $B_1$ | c.Hex |
| 134 | $H_2N(HN=)C-$ (5) | S | 2 | H | H | NH | $B_1$ | H |
| 135 | $H_2N(HN=)C-$ (6) | S | 2 | H | H | NH | $B_1$ | H |
| 136 | $E_1-HN(HN=)C-$ (6) | S | 2 | H | H | NH | $B_5$ | Et |
| 137 | $H_2N(HN=)C-$ (6) | S | 2 | H | H | NH | $B_5$ | Et |
| 138 | $H_2N(HN=)C-$ (6) | S | 2 | H | H | NH | $B_5$ | H |
| 139 | $H_2N(HN=)C-$ (6) | S | 2 | H | H | NH | $B_6$ | H |
| 140 | $H_2N(HN=)C-$ (6) | S | 2 | H | H | NH | $B_7(S)$ | H |
| 141 | $H_2N(HN=)C-$ (6) | S | 2 | H | H | NH | $B_{13}$ | H |

TABLE 8

| Compound No. | A (binding site) | L | binding site of CO | $R^1$ | $R^2$ | M | B | $R^5$ |
|---|---|---|---|---|---|---|---|---|
| 142 | $H_2N(HN=)C-$ (6) | S | 2 | H | H | NH | $B_{17}(S)$ | H |
| 143 | $H_2N(HN=)C-$ (6) | S | 2 | H | H | NH | $B_{24}$ | H |
| 144 | $H_2N(HN=)C-$ (6) | S | 2 | H | H | NH | $B_{32}$ | H |
| 145 | $H_2N(HN=)C-NH-$ (5) | S | 2 | H | H | NH | $B_1$ | Et |
| 146 | $H_2N(HN=)C-NH-$ (5) | S | 2 | H | H | NH | $B_1$ | H |
| 147 | $H_2N(HN=)C-NH-$ (5) | S | 2 | H | H | NH | $B_5$ | H |
| 148 | $H_2N(HN=)C-NH-$ (6) | s | 2 | H | H | NH | $B_5$ | H |
| 149 | $H_2N(HN=)C-NH-$ (6) | S | 2 | H | H | NH | $B_6$ | H |
| 150 | $H_2N(HN=)C-NH-$ (6) | S | 2 | H | H | O | $B_6$ | H |
| 151 | $H_2N(HN=)C-$ (5) | O | 2 | H | H | O | $B_{35}$ | tBu |
| 152 | $H_2N(HN=)C-$ (5) | O | 2 | H | H | O | $B_{35}$ | H |
| 153 | $H_2N(HN=)C-$ (5) | O | 2 | H | H | O | $B_{41}$ | H |
| 154 | $Z-HN(HN=)C-$ (5) | O | 2 | H | H | NH | $B_{39}$ | Et |
| 155 | $E_1-HN(HN=)C-$ (5) | O | 2 | H | H | NH | $B_{38}$ | Et |
| 156 | $E_4-HN(HN=)C-$ (5) | O | 2 | H | H | NH | $B_{38}$ | Et |
| 157 | $Bn-HN(HN=)C-$ (5) | O | 2 | H | H | NH | $B_{38}$ | Et |
| 158 | $H_2N(HN=)C-$ (5) | O | 2 | H | H | NH | $B_{38}$ | Me |
| 159 | $H_2N(HN=)C-$ (5) | O | 2 | H | H | NH | $B_{39}$ | Et |
| 160 | $H_2N(HN=)C-$ (5) | O | 2 | H | H | NH | $B_{39}$ | isoPr |
| 161 | $H_2N(HN=)C-$ (5) | O | 2 | H | H | NH | $B_{39}$ | tBu |

TABLE 9

| Compound No. | A (binding site) | L | binding site of CO | $R^1$ | $R^2$ | M | B | $R^5$ |
|---|---|---|---|---|---|---|---|---|
| 162 | $H_2N(HN=)C-$ (5) | O | 2 | H | H | NH | $B_{39}$ | c.Hex |
| 163 | $H_2N(HN=)C-$ (5) | O | 2 | H | H | NH | $B_{39}$ | $-CH_2CH_2OH$ |
| 164 | $H_2N(HN=)C-$ (5) | O | 2 | H | H | NH | $B_{36}$ | $-CH_2CH_2OH$ |
| 165 | $H_2N(HN=)C-$ (5) | O | 2 | H | H | NH | $B_{38}$ | H |
| 166 | $H_2N(HN=)C-$ (5) | O | 2 | H | H | NH | $B_{40}$ | H |
| 167 | $H_2N(HN=)C-$ (5) | O | 2 | H | H | NH | $B_{39}$ | H |
| 168 | $H_2N(HN=)C-$ (6) | O | 3 | H | H | NH | $B_{38}$ | H |
| 169 | $H_2N(HN=)C-$ (5) | O | 2 | H | 3-Me | NH | $B_{38}$ | H |
| 170 | $Z-HN(HN=)C-$ (5) | O | 2 | H | H | NH | $B_{36}$ | tBu |
| 171 | $Bn-HN(HN=)C-$ (5) | O | 2 | H | H | NH | $B_{36}$ | tBu |
| 172 | $Z-HN(HN=)C-$ (5) | O | 2 | H | H | NH | $B_{36}$ | H |
| 173 | $Bn-HN(HN=)C-$ (5) | O | 2 | H | H | NH | $B_{36}$ | H |
| 174 | $H_2N(HN=)C-$ (5) | O | 2 | H | H | NH | $B_{36}$ | Et |
| 175 | $H_2N(HN=)C-$ (5) | O | 2 | H | H | NH | $B_{36}$ | nBu |
| 176 | $H_2N(HN=)C-$ (5) | O | 2 | H | H | NH | $B_{36}$ | tBu |
| 177 | $H_2N(HN=)C-$ (5) | O | 2 | H | H | NH | $B_{36}$ | Bn |
| 178 | $H_2N(HN=)C-$ (5) | O | 2 | H | H | NH | $B_{37}$ | H |
| 179 | $H_2N(HN=)C-$ (5) | O | 2 | H | H | NH | $B_{36}$ | H |
| 180 | $H_2N(HN=)C-$ (6) | O | 2 | H | H | NH | $B_{35}$ | H |
| 181 | $H_2N(HN=)C-$ (5) | O | 2 | H | 3-Me | NH | $B_{36}$ | tBu |

TABLE 10

Structure: benzene ring with positions 4,5,6,7 and substituents A, R², R¹; five-membered ring with L₁, position 2, position 3, CO—M—B

| Compound No. | A (binding site) | L | binding site of CO | R¹ | R² | M | B | R⁵ |
|---|---|---|---|---|---|---|---|---|
| 182 | H₂N(HN=)C— (5) | O | 2 | H | 3-Me | NH | B₃₆ | H |
| 183 | H₂N(HN=)C— (5) | O | 2 | H | 3-OMe | NH | B₃₆ | tBu |
| 184 | H₂N(HN=)C— (5) | O | 2 | H | 3-OMe | NH | B₃₆ | H |
| 185 | E₁—HN(HN=)C— (5) | O | 2 | H | H | NH | B₄₁ | Et |
| 186 | Z—HN(HN=)C— (5) | O | 2 | H | H | NH | B₄₁ | Et |
| 187 | E₄—HN(HN=)C— (5) | O | 2 | H | H | NH | B₄₁ | Et |
| 188 | Bn—HN(HN=)C— (5) | O | 2 | H | H | NH | B₄₁ | Et |
| 189 | Z—HN(HN=)C— (5) | O | 2 | H | H | NH | B₄₁ | H |
| 190 | Bn—HN(HN=)C— (5) | O | 2 | H | H | NH | B₄₁ | H |
| 191 | H₂N(HN=)C— (5) | O | 2 | H | H | NH | B₄₁ | Et |
| 192 | H₂N(HN=)C— (5) | O | 2 | H | H | NH | B₄₁ | H |
| 193 | H₂N(HN=)C— (5) | O | 2 | H | H | O | B₄₁ | Et |
| 194 | H₂N(HN=)C— (5) | O | 2 | H | H | NH | B₄₂ | tBu |
| 195 | H₂N(HN=)C— (5) | O | 2 | H | H | NH | B₄₃ | H |
| 196 | H₂N(HN=)C— (5) | O | 2 | H | H | NH | B₄₄ | H |
| 197 | H₂N(HN=)C— (5) | O | 2 | H | H | NH | B₄₅ | tBu |
| 198 | H₂N(HN=)C— (5) | O | 2 | H | H | NH | B₄₅ | H |
| 199 | H₂N(HN=)C— (5) | O | 2 | H | H | NH | B₄₆ | H |
| 200 | H₂N(HN=)C— (5) | O | 2 | H | H | NH | B₄₇ | H |
| 201 | Z—HN(HN=)C— (5) | O | 2 | H | H | NH | B₄₈ | tBu |

TABLE 11

Structure: benzene ring with positions 4,5,6,7 and substituents A, R², R¹; five-membered ring with L₁, position 2, position 3, CO—M—B

| Compound No. | A (binding site) | L | binding site of CO | R¹ | R² | M | B | R⁵ |
|---|---|---|---|---|---|---|---|---|
| 202 | H₂N(HN=)C— (5) | O | 2 | H | H | NH | B₄₈ | Et |
| 203 | H₂N(HN=)C— (5) | O | 2 | H | H | NH | B₄₈ | tBu |
| 204 | H₂N(HN=)C— (5) | O | 2 | H | H | NH | B₄₈ | H |
| 205 | H₂N(HN=)C— (5) | O | 2 | H | H | NH | B₄₉ | H |
| 206 | H₂N(HN=)C— (6) | NH | 2 | H | 3-Me | NH | B₃₈ | H |
| 207 | Boc—HN(HN=)C— (6) | NH | 2 | H | H | NH | B₃₅ | Et |
| 208 | Bn—HN(HN=)C— (6) | NH | 2 | H | H | NH | B₃₆ | H |
| 209 | H₂N(HN=)C— (6) | NH | 2 | H | H | NH | B₃₆ | Et |
| 210 | H₂N(HN=)C— (6) | NH | 2 | H | H | NH | B₃₆ | tBu |
| 211 | H₂N(HN=)C— (5) | NH | 2 | H | H | NH | B₃₇ | H |
| 212 | H₂N(HN=)C— (6) | NH | 2 | H | H | NH | B₃₆ | H |
| 213 | E₅—HN(HN=)C— (6) | NH | 2 | H | H | NH | B₄₁ | Et |
| 214 | H₂N(HN=)C— (6) | NH | 2 | H | H | NH | B₄₁ | Et |
| 215 | H₂N(HN=)C— (6) | NH | 2 | H | H | NH | B₄₁ | H |
| 216 | H₂N(HN=)C— (6) | NH | 2 | H | H | NH | B₄₃ | H |
| 217 | H₂N(HN=)C— (6) | NH | 2 | H | H | NH | B₄₄ | H |
| 218 | E₁—HN(HN=)C— (6) | NH | 2 | H | H | NH | B₃₈ | Et |
| 219 | H₂N(HN=)C— (6) | NH | 2 | H | H | NH | B₃₈ | Et |
| 220 | H₂N(HN=)C— (6) | NH | 2 | H | H | NH | B₃₉ | H |
| 221 | H₂N(HN=)C— (6) | NH | 2 | H | H | O | B₃₈ | H |

TABLE 12

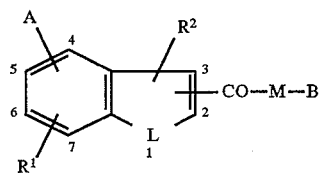

| Compound No. | A (binding site) | L | binding site of CO | $R^1$ | $R^2$ | M | B | $R^5$ |
|---|---|---|---|---|---|---|---|---|
| 222 | $H_2N(HN=)C-$ (6) | NH | 2 | H | H | O | $B_{35}$ | H |
| 223 | $H_2N(HN=)C-$ (6) | NH | 2 | H | H | O | $B_{41}$ | H |
| 224 | $H_2N(HN=)C-$ (6) | N—Me | 2 | H | H | NH | $B_{38}$ | H |
| 225 | $Bn-HN(HN=)C-$ (6) | S | 2 | H | H | NH | $B_{38}$ | H |
| 226 | $H_2N(HN=)C-$ (6) | S | 2 | H | H | NH | $B_{38}$ | Et |
| 227 | $H_2N(HN=)C-$ (6) | S | 2 | H | H | NH | $B_{39}$ | Et |
| 228 | $H_2N(HN=)C-$ (6) | S | 3 | H | H | NH | $B_{38}$ | H |
| 229 | $H_2N(HN=)C-$ (6) | S | 2 | H | H | NH | $B_{36}$ | nHex |
| 230 | $H_2N(HN=)C-$ (6) | S | 2 | H | H | NH | $B_{36}$ | Et |
| 231 | $H_2N(HN=)C-$ (5) | S | 2 | H | H | NH | $B_{35}$ | H |
| 232 | $H_2N(HN=)C-$ (6) | S | 2 | H | H | NH | $B_{36}$ | H |
| 233 | $H_2N(HN=)C-$ (6) | S | 2 | H | H | NH | $B_{41}$ | H |
| 234 | $H_2N(HN=)C-$ (6) | S | 2 | H | H | NH | $B_{38}$ | H |
| 235 | $Bn-HN(HN=)C-$ (6) | S | 2 | H | H | NH | $B_{41}$ | H |

TABLE 13

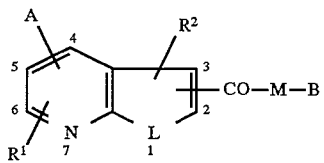

| Compound No. | A (binding site) | L | binding site of CO | $R^1$ | $R^2$ | M | B | $R^5$ |
|---|---|---|---|---|---|---|---|---|
| 236 | $E_3-HN(HN=)C-$ (5) | O | 2 | H | H | NH | $B_1$ | H |
| 237 | $Bn-HN(HN=)C-$ (5) | O | 2 | H | H | NH | $B_1$ | H |
| 238 | $H_2N(HN=)C-$ (5) | O | 2 | H | H | NH | $B_1$ | tBu |
| 239 | $H_2N(HN=)C-$ (5) | O | 2 | H | H | NH | $B_1$ | H |
| 240 | $H_2N(HN=)C-$ (5) | O | 2 | H | H | O | $B_1$ | H |
| 241 | $H_2N(HN=)C-$ (5) | O | 2 | H | H | NH | $B_5$ | Et |
| 242 | $H_2N(HN=)C-$ (5) | O | 2 | H | H | NH | $B_5$ | H |
| 243 | $Z-HN(HN=)C-$ (5) | O | 2 | H | H | NH | $B_{34}$ | Et |
| 244 | $H_2N(HN=)C-$ (5) | O | 2 | H | H | NH | $B_{34}$ | Bn |
| 245 | $H_2N(HN=)C-$ (5) | O | 2 | H | H | NH | $B_{34}$ | Et |
| 246 | $H_2N(HN=)C-$ (5) | O | 2 | H | H | NH | $B_{34}$ | H |
| 247 | $H_2N(HN=)C-$ (5) | O | 2 | H | H | NH | $B_6$ | H |
| 248 | $H_2N(HN=)C-$ (5) | O | 2 | H | H | O | $B_6$ | H |
| 249 | $H_2N(HN=)C-$ (5) | O | 2 | H | H | NH | $B_{17}$ | Et |
| 250 | $H_2N(HN=)C-$ (5) | O | 2 | H | H | NH | $B_7$ | H |
| 251 | $H_2N(HN=)C-$ (5) | O | 2 | H | H | NH | $B_{28}$ | H |
| 252 | $Boc-HN(HN=)C-$ (5) | O | 2 | H | H | NH | $B_{36}$ | Et |
| 253 | $H_2N(HN=)C-$ (5) | O | 2 | H | H | NH | $B_{36}$ | c.Hex |
| 254 | $H_2N(HN=)C-$ (5) | O | 2 | H | H | NH | $B_{36}$ | tBu |
| 255 | $H_2N(HN=)C-$ (5) | O | 2 | H | H | NH | $B_{36}$ | H |
| 256 | $H_2N(HN=)C-$ (5) | O | 2 | H | H | N—Me | $B_{36}$ | H |

TABLE 14
| Compound No. | A (binding site) | L | binding site of CO | $R^1$ | $R^2$ | M | B | $R^5$ |
|---|---|---|---|---|---|---|---|---|
| 257 | Z—HN(HN=)C— (5) | O | 2 | H | H | NH | $B_{39}$ | Et |
| 258 | $E_1$—HN(HN=)C— (5) | O | 2 | H | H | NH | $B_{39}$ | H |
| 259 | $H_2$N(HN=)C— (5) | O | 2 | H | H | NH | $B_{39}$ | isoPr |
| 260 | $H_2$N(HN=)C— (5) | O | 2 | H | H | NH | $B_{39}$ | Et |
| 261 | $H_2$N(HN=)C— (5) | O | 2 | H | H | NH | $B_{39}$ | H |
| 262 | $E_1$—HN(HN=)C— (5) | O | 2 | H | H | NH | $B_{41}$ | H |
| 263 | $H_2$N(HN=)C— (5) | O | 2 | H | H | NH | $B_{41}$ | H |
| 264 | $H_2$N(HN=)C— (5) | O | 2 | H | H | NH | $B_{43}$ | Et |
| 265 | $H_2$N(HN=)C— (5) | O | 2 | H | H | NH | $B_{43}$ | H |
| 266 | $H_2$N(HN=)C— (5) | O | 2 | H | H | NH | $B_{48}$ | tBu |
| 267 | $H_2$N(HN=)C— (5) | O | 2 | H | H | NH | $B_{48}$ | H |
| 268 | $H_2$N(HN=)C— (5) | O | 2 | H | H | NH | $B_{44}$ | H |
| 269 | $H_2$N(HN=)C— (5) | O | 2 | H | H | NH | $B_{47}$ | H |
TABLE 15
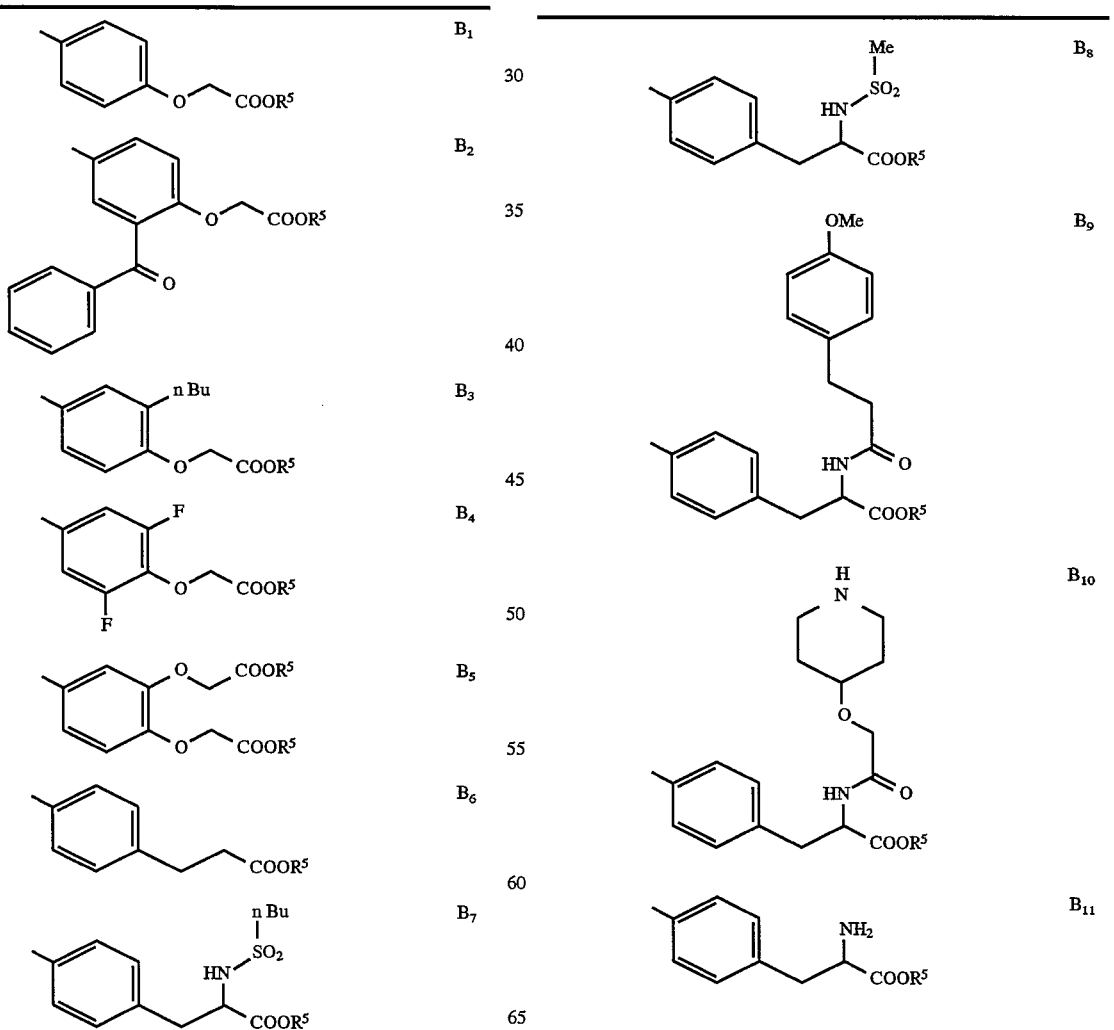

TABLE 15-continued
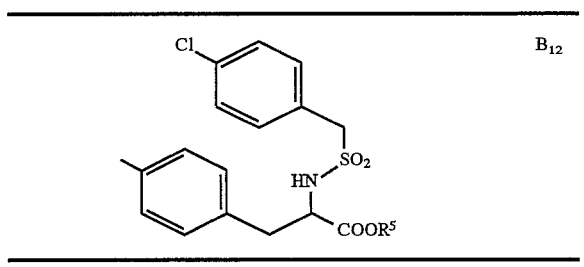 B_12
TABLE 16
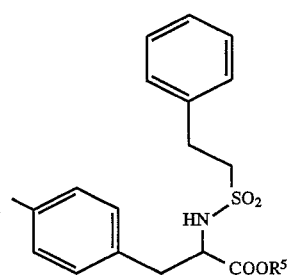 B_13
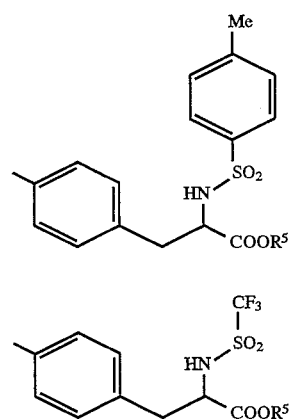 B_14, B_15
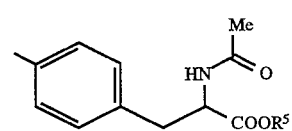 B_16
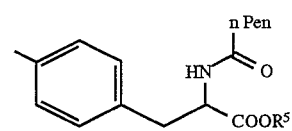 B_17
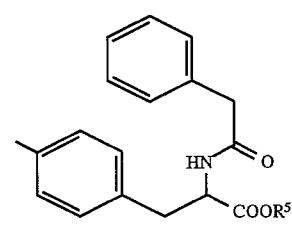 B_18
TABLE 16-continued
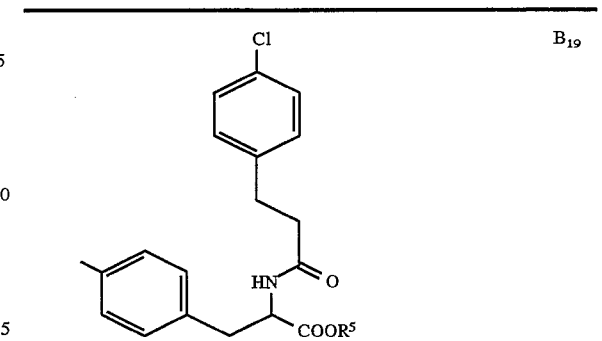 B_19, B_20, B_21, B_22, B_23, B_24
TABLE 17
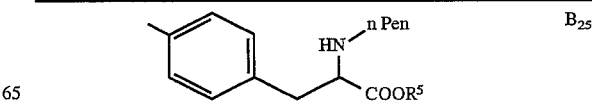 B_25

TABLE 17-continued
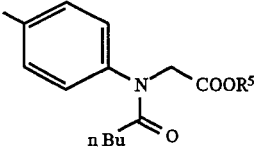 B26
 B27
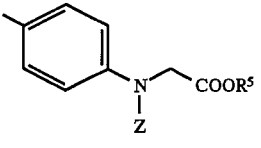 B28
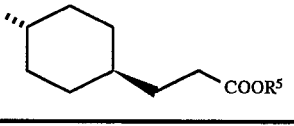 B29
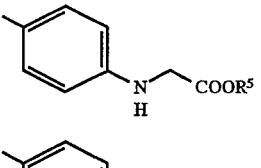 B30
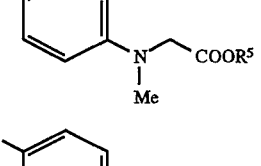 B31
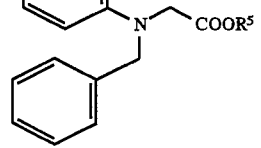 B32
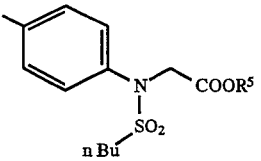 B33
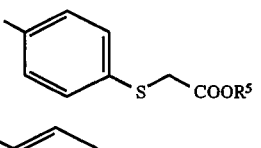 B34
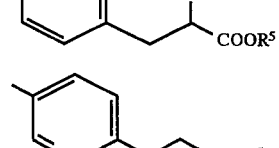 B35
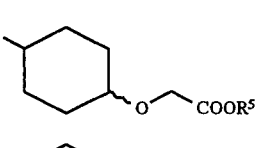 B36
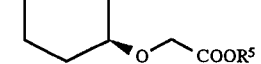 B37
TABLE 17-continued
 B38
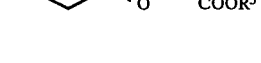 B39
TABLE 18
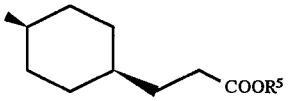 B40
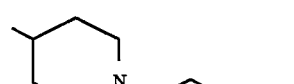 B41
 B42
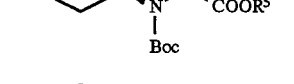 B43
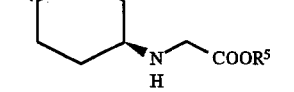 B44
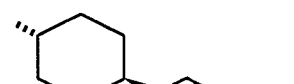 B45
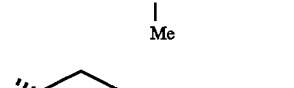 B46
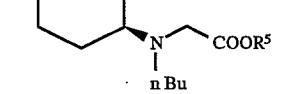 B47

TABLE 18-continued

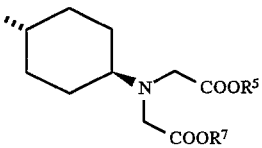

B48

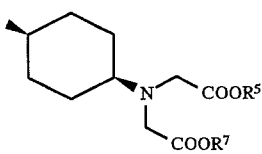

B49

Of the above-mentioned compounds, particularly preferable compounds are as follows.

Compound (10) 4-[(5-amidino-2-benzofuranyl)carbonylamino]phenoxyacetic acid

Compound (29) [[4-[(5-amidino-2-benzofuranyl)carbonylamino]-ophenylene]dioxy]diacetic acid Compound (48) 3-[4-[(5-amidino-2-benzofuranyl)carbonylamino]phenyl]2-(n-butylsulfonylamino)propionic acid Compound (159) ethyl trans-3-[4-[(5-amidino-2-benzofuranyl)carbonylamino]cyclohexyl]propionate Compound (167) trans-3-[4-[(5-amidino-2-benzofuranyl)carbonylamino]cyclohexyl]propionic acid Compound (174) ethyl trans-[4-[(5-amidino-2-benzofuranyl)carbonylamino]cyclohexyloxy]acetate Compound (179) trans-[4-[(5-amidino-2-benzofuranyl)carbonylamino]cyclohexyloxy]acetic acid Compound (192) 3-[4-[(5-amidino-2-benzofuranyl)carbonylamino]piperidino]propionic acid Compound (203) di-t-butyl trans-[4-[(5-amidino-2-benzofuranyl)-carbonylamino]cyclohexylamino]diacetate Compound (204) trans-[4-[(5-amidino-2-benzofuranyl)carbonylamino]cyclohexylamino]diacetic acid Compound (232) trans-[4-[(6-amidinobenzo[b]thien-2-yl)carbonylamino]cyclohexyloxy]acetic acid The compound (I) and pharmacologically acceptable salts thereof of the present invention have superior GPIIb/IIIa antagonism in mammals such as human, mouse, rat, rabbit, dog and cat. They have low toxicity and can be administered orally. They show persistent life in blood and have less side-effects such as prolonged bleeding time.

Accordingly, the compound (I) and pharmacologically acceptable salts thereof are useful as GPIIb/IIIa antagonists. They inhibit the formation of thrombus of platelets and serve well for the prophylaxis and treatment of the diseases caused by the formation of thrombus of platelets, such as thrombosis, stroke, heart failure, inflammation and arteriosclerosis.

The compound (I) and pharmacologically acceptable salts thereof of the present invention are applicable to the diseases and the like, such as ischemic heart diseases [e.g., angina pectoris (insecurity or effort), myocardial infarction, and after PTCA (percutaneous transluminal coronary angioplasty)], cerebrovascular diseases [e.g., TIA (transient ischemic attack), cerebral infarction (thrombus, embolus) and subarachnoid hemorrhage (vascular contraction)], heart vascular surgeries [e.g., valve substitution operation, A–C bypass (prevention of graft obstruction after coronary bypass operation), blood circulation reconstructive surgery, arteriovenous shunt, peripheral arterial obliteration (e.g., ASO (arteriosclerotic obliteration) and Burger disease), deep phlebothrombosis and artery-dependent congenital heart disease], respiratory diseases [e.g., pulmonary embolism, bronchial asthma, pulmonary, edema, ARDS (adult respiratory distress syndrome) and pulmonary hypertension], renal diseases (e.g., nephrotic syndrome and glomerular nephritis), collagen diseases [e.g., SLE (systemic lupus erythematode), RA (rheumatoid arthritis) and PSS (progressive systemic sclerosis) (Raynaud phenomenon)], artificial organs [e.g., pump oxygenator, and artificial dialysis], and others [e.g., essential thrombocythemia, TTP (thrombotic thrombocytopenic purpura), HUS (hemolytic uremic syndrome), DIC (disseminated intravascular coagulation), Kawasaki's disease, diabetes, organ transplantation, arteriosclerosis, vibration disease, shock, oxytocic action, peptic ulcer, reinforcing effects of t-PA (tissue plasminogen activator) and eclampsia].

Moreover, said compound (I) and pharmacologically acceptable salts thereof inhibit metastasis of tumor cells. They also accelerate the cure of wounds. They prevent deterioration of bones and can be used for the treatment of osteoporosis.

The GPIIb/IIIa-antagonistic action of the compound (I) and pharmacologically acceptable salts thereof of the present invention can be clarified by, for example, determining, by a known method, the inhibitory activity against ADP (adenosine 5'-diphosphate) aggregation of platelets and inhibitory activity against the binding of fibrinogen to platelets (see literatures of Leo Alig et al and G. D. Hartmans et al mentioned above).

The compound (I') which is encompassed in the compound (I) of the present invention and salts thereof can be converted to an inclusion compound with a cyclodextrin or a derivative thereof, for improving water-solubility. Said inclusion compound is a compound obtained by the inclusion of the compound (I') or its salt by a cyclodextrin or its derivative.

The salt of the compound (I') is exemplified by the above-mentioned pharmacologically acceptable salts.

Examples of the cyclodextrin or its derivatives which can be used for preparing an inclusion compound include α-cyclodextrin, β-cyclodextrin, γ-cyclodextrin, derivatives of these such as ester compound at hydroxy of glucose residue (e.g., acetylated compound), ether compound thereof (e.g., methylated compound, hydroxyethylated compound and hydroxypropylated compound), nitrogen-containing compound thereof (e.g., aminomethylcyclodextrin), sulfur-containing compound thereof (e.g., cyclodextrinsulfate), acid group-containing compound thereof (e.g., carboxymethylcyclodextrin) and sugar-containing compound thereof (e.g., glucosylated compound and mantosylated compound).

The method for preparing an inclusion compound is not particularly limited and can be a method known per se. The mixing ratio of [compound (I') or a salt thereof]: [cyclodextrin or a derivative thereof]is preferably 1:0.5–1:50, particularly preferably 1:1–1:10.

When the compound (I), a pharmacologically acceptable salt thereof or the above-mentioned inclusion compound of the present invention is used as the above-mentioned pharmaceutical product, pharmacologically acceptable additives such as carriers, excipients and diluents are appropriately admixed with pharmaceutically necessary ingredients, and the mixture is formulated into pharmaceutical compositions such as powders, granules, tablets, capsules, syrups, injections, ointments and creams, which are orally or parenterally administered. The above preparations contain an effective amount of the compound (I) or a pharmacologically acceptable salt thereof.

The dose of said compound (I) or a pharmacologically acceptable salt thereof varies depending on the administration route, symptom, body weight, age of patients and the like, and can be appropriately determined according to the administration object. Generally, they are orally administered to an adult in a dose of 0.01–1,000 mg/kg body weight/day, preferably 0.05–500 mg/kg body weight/day in one to several doses.

In said compound (I), the group A has or does not have an amino-protecting group and the group B has a free carboxylic group or an ester thereof. The above groups are appropriately selected according to the administration route, the kind of diseases, the object of treatment and the like, in consideration of efficacy, duration of efficacy, toxicity, solubility, stability, absorption and the like, and all of them afford useful GPIIb/IIIa antagonists.

The present invention is explained in more detail in the following by illustrative examples, to which the present invention is not limited.

The determination of $^1$H-NMR was performed at 200 MHz unless otherwise specifically indicated.

EXAMPLE 1

(1) t-Butyl 4-aminophenoxyacetate

4-Nitrophenol (13.9 g, 100 mmol) was dissolved in N,N-dimethylformamide (20 ml), and t-butyl bromoacetate (29.3 g, 150 mmol) and potassium carbonate (27.6 g, 200 mmol) were added, which was followed by stirring at 70° C. for 4 hours. The reaction mixture was diluted with ethyl acetate (100 ml), washed with water, and the aqueous layer was extracted with ethyl acetate. The extract and the previously-obtained organic layer were combined. The mixture was washed with water and dried over anhydrous magnesium sulfate. After filtration, low boiling matters were distilled away from the filtrate under reduced pressure, and the residue was purified by silica gel column chromatography (n-hexane/ethyl acetate=5/1) and recrystallized from a mixed solvent of ethyl acetate and n-hexane to give 21.8 g of t-butyl 4-nitrophenoxyacetate as pale-yellow crystals (86%).

IR(KBr): 1740, 1590, 1500, 1330, 1240, 1160 cm$^{-1}$ $^1$H-NMR (DMSO-d$_6$) $\delta_{TMS}$: 8.21 (d,J=7.1 Hz,2H), 7.13 (d,J=7.1 Hz,2H), 4.86(s,2H), 1.43(s,9H)

t-Butyl 4-nitrophenoxyacetate (19.3 g, 76.0 mmol) was dissolved in ethanol (100 ml) and 10% palladium-carbon (1.0 g) was added. The mixture was stirred at room temperature for 18 hours under a hydrogen atmosphere. The reaction mixture was filtrated and low boiling matters were distilled away from the filtrate under reduced pressure to give 16.8 g of t-butyl 4-aminophenoxyacetate as a pale-brown solid (99%).

IR(neat): 3350, 2950, 1740, 1510, 1220, 1150 cm$^{-1}$ $^1$H-NMR (DMSO-d$_6$) $\delta_{TMS}$: 6.62(d,J=6.6 Hz,2H), 6.49(d, J=6.6 Hz,2H), 4.63(s,2H), 1.43(s,2H), 1.41(s, 9H)

(2) t-Butyl 4-[(5-cyano-2-benzofuranyl)carbonylamino]phenoxyacetate

5-Cyano-2-benzofurancarboxylic acid (300 mg, 1.60 mmol) and t-butyl 4-aminophenomyacetate (395 mg, 1.76 mmol) were dissolved in N,N-dimethylformamide (40 ml), and 1-hydroxy-1H-benzotriazole (238 mg, 1.76 mmol) and 1-(3-dimethylaminopropyl)-3-ethylcarbodiimide (342 mg, 1.76 mmol) were added. The mixture was stirred at room temperature for 18 hours. Water (100 ml) was added to the reaction mixture, and the mixture was extracted with ethyl acetate. The extract was washed with water and saturated brine, and dried over anhydrous magnesium sulfate. After filtration, low boiling matters were distilled away from the filtrate under reduced pressure and the residue was purified by silica gel column chromatography (n-hexane/ethyl acetate=1/1) to give 512 mg of t-butyl 4-[(5-cyano-2-benzofuranyl)carbonylamino]phenoxyacetate as a pale-yellow solid (82%).

IR(KBr): 2200, 1750, 1680, 1605, 1530, 1505 cm$^{-1}$ $^1$H-NMR (CDCl$_3$) $\delta_{TMS}$: 8.07(d,J=0.8 Hz, 1H), 7.75–7.60 (m,5H), 6.94(d,2H), 4.53(s,2H), 1.50(s,9H)

(3) t-Butyl 4-[(5-amidino-2-benzofuranyl)carbonylamino]phenoxyacetate (compound (8))

t-Butyl 4-[(5-cyano-2-benzofuranyl)carbonylamino]phenoxyacetate (430 mg, 1.10 mmol) was dissolved in a mixed solution of pyridine (30 ml) and triethylamine (7 ml), and hydrogen sulfide gas was blown in for 10 minutes at room temperature, which was followed by stirring for 18 hours. Low boiling matters were distilled away from the reaction mixture under reduced pressure and the residue was dissolved in ethyl acetate. The mixture was washed with a 2N aqueous potassium hydrogensulfate solution, water and saturated brine, and dried over anhydrous magnesium sulfate. After filtration, low boiling matters were distilled away from the filtrate under reduced pressure to give t-butyl 4-[(5-thiocarbamoyl-2-benzofuranyl)carbonylamino]phenoxyacetate as a yellow solid. The solid was dissolved in acetone (50 ml) and methyl iodide (2 ml) was added. The mixture was refluxed under heating for 40 minutes. Low boiling matters were distilled away from the reaction mixture under reduced pressure to give t-butyl 4-[[5-[(1-methylthio)iminomethyl]-2-benzofuranyl)carbonylamino]phenoxyacetate as a yellow solid. Thereto were added methanol (30 ml) and ammonium acetate (280 mg, 3.64 mmol), and the mixture was refluxed under heating for 3 hours. Low boiling matters were distilled away from the reaction mixture under reduced pressure and the residue was purified by silica gel column chromatography (chloroform/methanol=100/3-3/1) to give 596 mg of hydriodide of compound (8) as a yellow solid (quantitatively in 3 steps).

IR(KBr): 3700–2900, 1730, 1640, 1600 cm$^{-1}$ $^1$H-NMR (DMSO-d$_6$) $\delta_{TMS}$: 8.32(s,1H), 8.00–7.80(m, 3H), 7.69(d,2H), 6.93(d,2H), 4.65(s,2H), 1.44(s,9H)

EXAMPLE 2

4-[(5-Amidino-2-benzofuranyl)carbonylamino]phenoxyacetic acid (compound (10))

Methylene chloride (25 ml) was added to hydriodide (537 mg, 1.00 mmol) of compound (8), and trifluoroacetic acid (8 ml) was added, which was followed by stirring at room temperature for 2 hours. Diethyl ether (100 ml) was added to the reaction mixture and the mixture was stirred for 10 minutes. The resulting precipitate was collected by filtration and washed with diethyl ether to give 380 mg of hydriodide of compound (10) as a pale-brown solid (79%).

Melting point: >250° C.

IR(KBr): 1740, 1690, 1610, 1540, 1505 cm$^{-1}$ $^1$H-NMR (DMSO-d$_6$, 500 MHz) $\delta_{TMS}$: 10.57(s,1H), 9.38 (bs,2H), 9.11(bs,2H), 8.34(d,J=1.7 Hz,1H), 7.97(d,J=8.8 Hz,1H), 7.91(s,1H), 7.89(dd,J=1.7,8.8 Hz, 1H), 7.72–7.69 (m,2H), 6.97–6.93(m,2H), 4.67(s,2H)

EXAMPLE 3 t-Butyl 4-[(5-amidino-3-methyl-2-benzofuranyl)carbonylamino]phenoxyacetate (compound (13))

In the same manner as in Example 1 (2), 5-cyano-3-methyl-2-benzofurancarboxylic acid (427 mg, 1.86 mmol)

and t-butyl aminophenoxyacetate (500 mg, 2.24 mmol) were condensed and purified by silica gel column chromatography (n-hexane/ethyl acetate=7/3) to give 562 mg of t-butyl 4-[(5-cyano-3-methyl-2-benzofuranyl)carbonylamino]-phenoxyacetate as a colorless solid (74%).

IR(KBr): 2450, 1715, 1660, 1610, 1535, 1505, 1210, 1150 cm$^{-1}$ $^1$H-NMR (DMSO-d$_6$) $\delta_{TMS}$: 8.23(s,1H), 8.00–7.99(m, 1H), 7.72(dd,J=1.6,8.6 Hz,1H), 7.63–7.59(m,3H), 6.95–6.91(m,2H), 4.52(s,2H), 2.69(s,3H), 1.50(s,9H)

In the same manner as in Example 1 (3), the cyano group of t-butyl -4-[(5-cyano-3-methyl-2-benzofuranyl) carbonylamino]phenoxyacetate (550 mg, 1.35 mmol) was converted to an amidino group, which was followed by purification by silica gel column chromatography (chloroform/methanol=95/5-85/15) to give 520 mg of hydriodide of compound (13) as a pale-brown solid (70% in 3 steps).

$^1$H-NMR (DMSO-d$_6$) $\delta_{TMS}$: 9.32(bs,4H), 8.33–8.32(m, 1H), 7.91–7.89(m,2H), 7.71(d,J=9.1 Hz,2H), 6.81(d,J=9.1 Hz,2H), 4.65(s,2H), 2.64(s,3H), 1.44(s,9H)

EXAMPLE 4

4-[(5-Amidino-3-methyl-2-benzofuranyl)carbonylamino] phenoxyacetic acid (compound (16))

In the same manner as in Example 2, hydriodide (510 mg, 0.925 mmol) of compound (13) was treated with trifluoroacetic acid (6 ml) to give 382 mg of hydroiodide of compound (16) as a brown solid (83%).

Melting point: 220°–228° C. (dec.)

IR(KBr): 3300, 3100, 1730, 1670, 1610, 1535, 1510, 1205, 1140 cm$^{-1}$ $^1$H-NMR (DMSO-d$_6$, 500 MHz) $\delta_{TMS}$: 10.42(s,1H), 9.38 (bs,2H), 9.14(bs,2H), 8.34(d,J=1.8 Hz,1H), 7.92(dd,J=1.8, 8.6 Hz,1H), 7.90(d,J=8.6 Hz,1H), 7.73–7.70(m,2H), 6.94–6.91(m,2H), 4.67(s,2H), 2.64(s,3H)

EXAMPLE 5

(1) t-Butyl 4-(methylamino)phenoxyacetate t-Butyl 4-aminophenoxyacetate (7.00 g, 31.4 mmol) and succinimide (3.11 g, 31.4 mmol) were added to ethanol (40 ml), and a 37% aqueous formaldehyde solution (2.55 g, 31.4 mmol) was added. The mixture was refluxed under heating for 4 hours. Low boiling matters were distilled away from the reaction mixture under reduced pressure and the residue was purified by silica gel column chromatography (ethyl acetate) to give 8.37 g of t-butyl 4-(succinimidomethylamino)phenoxyacetate as a yellow solid (84%). This solid (8.30 g, 26.0 mmol) was dissolved in dimethyl sulfoxide (50 ml) and sodium borohydride (989 mg, 26.0 mmol) was added, which was followed by stirring at 100° C. for 30 minutes. After cooling, water was poured into the reaction mixture and the mixture was extracted with diethyl ether. The extract was washed with water and saturated brine, and dried over anhydrous magnesium sulfate. After filtration, low boiling matters were distilled away from the filtrate under reduced pressure and the residue was purified by silica gel column chromatography (n-hexane/ ethyl acetate=1/1) to give 3.62 g of t-butyl 4-(methylamino) phenoxyacetate as a yellow oil (59%).

$^1$H-NMR (DMSO-d$_6$) $\delta_{TMS}$: 6.69(d,2H), 6.45(d,2H), 4.51 (s,2H), 2.61(d,J=5.2 Hz,3H), 1.42(s,9H)

(2) t-Butyl 4-[(5-amidino-2-benzofuranyl)carbonyl-N-methylamino]phenoxyacetate (compound (20))

In the same manner as in Example 1 (2), 5-cyano-2-benzofurancarboxylic acid (300 mg, 1.60 mmol) and t-butyl 4-(methylamino)phenoxyacetate (417 mg, 1.76 mmol) were condensed and purified by silica gel column chromatography (chloroform/methanol=10/1) to quantitatively give 652 mg of t-butyl 4-[(5-cyano-2-benzofuranyl)carbonyl-N-methylamino]phenoxyacetate as a yellow solid.

$^1$H-NMR (DMSO-d$_6$) $\delta_{TMS}$: 8.15(s,1H), 7.96(s,1H), 7.82–7.65(m,2H), 7.31(d,2H), 6.95(d,2H), 4.69(s,2H), 3.36 (s,3H), 1.40(s,9H)

In the same manner as in Example 1 (3), the cyano group of t-butyl 4-[(5-cyano-2-benzofuranyl)carbonyl-N-methylamino]phenoxyacetate (652 mg, 1.60 mmol) was converted to an amidino group and 392 mg of hydriodide of compound (20) was obtained as a yellow solid (44% in 3 steps).

$^1$H-NMR (DMSO-d$_6$) $\delta_{TMS}$: 8.08(s,1H), 7.76(s,2H), 6.46 (bs,1H), 7.31(d,2H), 6.96(d,2H), 4.69(s,2H), 3.37(s,3H), 1.42(s,9H)

EXAMPLE 6

4-[(5-Amidino-2-benzofuranyl)carbonyl-N-methylamino] phenoxyacetic acid (compound (21))

In the same manner as in Example 2, hydroiodide (390 mg, 0.708 mmol) of compound (20) was treated with trifluoroacetic acid (5 ml) to give 281 mg of hydriodide of compound (21) as a yellow solid (80%).

Melting point: 185°–195° C. (dec.)

IR(KBr): 3700–2800, 1750, 1690, 1640, 1505 cm$^{-1}$ $^1$H-NMR (DMSO-d$_6$, 500 MHz) $\delta_{TMS}$: 13.11(bs,1H), 9.26(bs,2H), 9.16(bs,2H), 8.10(s,1H), 7.76(s,2H), 7.32(d, 2H), 6.97(d,2H), 6.43(bs,1H), 4.71(s,2H), 3.37(s,3H)

EXAMPLE 7

(1) Di-t-butyl [(4-amino-o-phenylene)dioxy]diacetate

4-Nitrocatechol (7.95 g, 51.3 mmol) and t-butyl bromoacetate (25.0 g, 128 mmol) were dissolved in N,N-dimethylformamide (100 ml) and potassium carbonate (19.7 g, 143 mmol) was added, which was followed by stirring at more temperature for 24 hours. Water was poured into the reaction mixture and the mixture was extracted with diethyl ether. The extract was washed with water and saturated brine, and dried over anhydrous magnesium sulfate. After filtration, low boiling matters were distilled away from the filtrate under reduced pressure and the residue was recrystallized from a mixed solution of n-hexane and ethyl acetate to give 18.10 g of di-t-butyl [(4-nitro-o-phenylene)dioxy] diacetate as colorless crystals (61%). The crystals (13.10 g, 34.1 mmol) was dissolved in ethyl acetate (70 ml) and 10% palladium-carbon (1.3 g) was added. The mixture was stirred at room temperature for 5 hours under a hydrogen atmosphere. The reaction mixture was filtered through Celite and low boiling matters were distilled away from the filtrate under reduced pressure to give 11.81 g of di-t-butyl [(4-amino-o-phenylene)dioxy]diacetate as a colorless oil (98%).

IR(KBr): 3350, 3000, 1740, 1510, 1150 cm$^{-1}$ $^1$H-NMR (CDCl$_3$) $\delta_{TMS}$: 6.79(m,1H), 6.27–6.20(m,2H), 4.54(s,2H), 4.50(s,2H), 1.48(s,1H), 1.47(s,9H)

(2) Di-t-butyl [[4-[(5-amidino-2-benzofuranyl) carbonylamino]-o-phenylene]dioxy]diacetate (compound (28))

In the manner as in Example 1 (2), 5-cyano-2-benzofurancarboxylic acid (200 mg, 1.07 mmol) and t-butyl [(4-amino-o-phenylene)dioxy]diacetate (415 mg, 1.17 mmol) were condensed and purified by silica gel column chromatography (n-hexane/ethyl acetate=3/1-1/1) to give 473 mg of di-t-butyl [[4-[(5-cyano-2-benzofuranyl)carbonylamino]-o-phenylene]dioxy]diacetate as a colorless solid (84%).

IR(KBr): 2220, 1740, 1735, 1640, 1275–1215 cm$^{-1}$ $^1$H-NMR (DMSO-d$_6$) $\delta_{TMS}$: 8.07(s,1H), 7.78–7.66(m, 2H), 7.61(s,1H), 7.52(d,J=2.4 Hz, 1H), 7.15(dd,J=8.7,2.4 Hz,1H), 6.90(d,J=8.7 Hz,1H), 4.65(s,2H), 4.61(s,2H), 1.50 (s,9H), 1.48(s,9H)

In the same manner as in Example 1 (3), the cyano group of di-t-butyl [[4-[(5-cyano-2-benzofuranyl)carbonylamino]-o-phenylene]dioxy]-diacetate (463 mg, 0.881 mmol) was converted to an amidino group and purified by silica gel column chromatography (chloroform/methanol=95/5-85/15) to give 244 mg of hydriodide of compound (28) as a yellow solid (42% in 3 steps).

$^1$H-NMR (DMSO-d$_6$) $\delta_{TMS}$: 10.52(bs,1H), 9.34(bs,4H), 8.33(s,1H), 8.00–7.85(m,3H), 7.52(d,J=2.1 Hz,1H), 7.35 (dd,J=8.9,2.1 Hz,1H), 6.93(d,J=8.9 Hz,1H), 4.66(s,4H), 1.45(s,9H), 1.44(s,9H)

EXAMPLE 8

[[4-[(5-Amidino-2-benzofuranyl)carbonylamino]-o-phenylene]dioxy]diacetic acid (compound (29))

In the same manner as in Example 2, hydriodide (187 mg, 0.280 mmol) of compound (28) was treated with trifluoroacetic acid (3 ml) to give 127 mg of hydriodide of compound (29) as a pale-brown solid (82%).

Melting point: >250° C.

IR(KBr): 3300, 1660, 1200, 1135 cm$^{-1}$ $^1$H-NMR (DMSO-d$_6$, 500 MHz) $\delta_{TMS}$: 13.01(bs,1H), 13.00(bs,1H), 10.55(bs,1H), 9.38(s,2H), 9.24(s,2H), 8.33(d, J=1.7 Hz,1H), 7.96(d,J=8.8 Hz,1H), 7.89(dd,J=1.7,8.8 Hz,1H), 7.89(s,1H), 7.43–7.41(m,2H), 6.93(d,J=9.5 Hz, 1H), 4.69(s,2H), 4.68(s,2H)

EXAMPLE 9

(1) Methyl 3-(4-aminophenyl)propionate

4-Aminocinnamic acid (15.0 g, 77.6 mmol) was added to a mixed solvent of methanol (250 ml) and chloroform (150 ml), and sulfuric acid (3 ml) was added, which was followed by refluxing under heating for 47 hours. The reaction mixture was concentrated under reduced pressure, and the residue was made weak alkaline with a saturated aqueous sodium hydrogencarbonate and the mixture was extracted with ethyl acetate. The extract was washed with water and saturated brine, and dried over anhydrous magnesium sulfate. After filtration, low boiling matters were distilled away from the filtrate under reduced pressure to give 7.84 g of methyl 4-aminocinnamate as a yellow solid (72%). This solid (7.80 g, 44.1 mmol) was dissolved in methanol (250 ml) and 10% palladium-carbon (780 mg) was added. The mixture was stirred at room temperature for 19 hours under a hydrogen atmosphere. The reaction mixture was filtered through Celite and low boiling matters were distilled away from the filtrate under reduced pressure. The residue was purified by silica gel column chromatography (n-hexane/ethyl acetate=3/1) to give 5.98 g of methyl 3-(4-aminophenyl)propionate as a colorless solid (76%).

Melting point: 47°–49.5° C.

IR(KBr): 3700–2500, 1710, 1600, 1500, 1425 cm$^{-1}$ $^1$H-NMR (CDCl$_3$) $\delta_{TMS}$: 6.97(d,2H), 6.61 (d,2H), 3.66(s, 3H), 2.83(t,J=6.8 Hz,2H), 2.57 (t,J=6.8 Hz,2H)

(2) Methyl 3-[4-[(5-amidino-2-benzofuranyl) carbonylamino]phenyl]propionate (compound (35))

In the same manner as in Example 1 (2), 5-cyano-2-benzofurancarboxylic acid (200 mg, 1.07 mmol) and methyl 3-(4-aminophenyl)propionate (211 mg, 1.18 mmol) were condensed to quantitatively give 371 mg of methyl 3-[4-[(5-cyano-2-benzofuranyl)carbonylamino]phenyl]propionate as a yellow solid.

IR(KBr): 2200, 1735, 1685, 1600, 1520 cm$^{-1}$ $^1$H-NMR (DMSO-d$_6$) $\delta_{TMS}$: 10.59(bs,1H), 8.44(s,1H), 7.94(s,2H), 7.86(s,1H), 7.69(d,2H), 7.22(d,2H), 3.59(s,3H), 2.84(t,J=7.0 Hz,2H), 2.63(t,J=7.0 Hz,2H)

In the same manner as in Example 1 (3), the cyano group of methyl 3-[4-[(5-cyano-2-benzofuranyl)carbonylamino]phenyl]propionate (350 mg, 7.01 mmol) was converted to an amidino group and purified by silica gel column chromatography (methylene chloride/methanol=100/3-5/1) to give 206 mg of hydriodide of compound (35) as a yellow solid (41% in 3 steps).

IR(KBr): 7700, 7645, 7600, 7535 cm$^{-1}$ $^1$H-NMR (DMSO-d$_6$) $\delta_{TMS}$: 10.59(bs,1H), 9.36(bs,2H), 8.92(bs,2H), 8.33(s,1H), 8.01–7.85(m,3H), 7.70(d,2H), 7.24 (d,2H), 3.59(s,3H), 2.85(t,J=7.4 Hz,2H), 2.64(t,J=7.4 Hz,2H)

EXAMPLE 10

3-[4-[(5-Amidino-2-benzofuranyl)carbonylamino]phenyl] propionate (compound (37))

Hydriodide (762 mg, 0.329 mmol) of compound (35) was suspended in tetrahydrofuran (6 ml) and a 1N aqueous sodium hydroxide solution (3.0 ml, 3.0 mmol) was added, which was followed by stirring at room temperature for one hour. The reaction mixture was adjusted to pH 2 with 1N hydrochloric acid and concentrated under reduced pressure. The resulting precipitate was collected by filtration and washed with water to give 82 mg of hydrochloride of compound (37) as a yellow solid (64%).

Melting point: >250° C.

IR(KBr): 3600–2700, 1700, 7650, 1600, 1535 cm$^{-1}$ $^1$H-NMR (DMSO-d$_6$) $\delta_{TMS}$: 12.11(bs,1H), 10.67(s,1H), 9.47(bs,2H), 9.26(bs,2H), 8.37(d,J=1.8 Hz, 1H), 8.02(s,1H), 7.97(d,J=8.8 Hz,1H), 7.91(dd,J=1.8,8.8 Hz, 1H), 7.73(d, 2H), 7.23(d,2H), 2.82(t,J=7.7 Hz,2H), 2.57(t,J=7.7 Hz,2H)

EXAMPLE 11

(1) Methyl 3-(4-aminophenyl)-2-(n-butylsulfonylamino) propionate

2-Amino-3-(4-nitrophenyl)propionic acid (4.60 g, 27.9 mmol) was added to a mixed solution of methanol (100 ml) and chloroform (50 ml), and sulfuric acid (3 ml) was added, which was followed by refluxing under heating for 30 hours. The reaction mixture was concentrated under reduced pressure and water was added to the residue. The pH was adjusted to 8–9 with a 1N aqueous sodium hydroxide solution and the mixture was extracted with chloroform. The extract was washed with water and saturated brine, and dried over anhydrous magnesium sulfate. After filtration, low boiling matters were distilled away from the filtrate under reduced pressure to give 4.06 g of methyl 2-amino-3-(4-nitrophenyl)propionate as a yellow oil (83%). This oil (4.00 g, 17.8 mmol) was dissolved in acetonitrile (56 ml), and pyridine (1.76 ml, 21.4 mmol) and n-butylsulfonyl chloride (2.80 g, 17.8 mmol) were sequentially added, which was followed by stirring at 70° C. for 4.5 hours. After cooling, the reaction mixture was poured into water (70 ml) and extracted with ethyl acetate. The extract was washed with water and saturated brine, and dried over anhydrous magnesium sulfate. After filtration, low boiling matters were distilled away from the filtrate under reduced pressure to give 4.06 g of methyl 2-(n-butylsulfonylamino)-3-(4-nitrophenyl)propionate as an orange oil (66%). This oil (3.40 g, 9.88 mmol) was dissolved in acetic acid (130 ml) and 10% palladium-carbon (1.5 g) was added. The mixture was stirred for 3 days under a hydrogen atmosphere. The reaction mixture was filtered through Celite and acetic acid was distilled away from the filtrate under reduced pressure to quantitatively give 3.16 g of methyl 3-(4-aminophenyl)-2-(n-butylsulfonylamino) propionate as a brown solid.

$^1$H-NMR (CDCl$_3$) $\delta_{TMS}$: 7.50–7.25(m,4H), 4.25–4.05(m, 1H), 3.65(s,3H), 3.04(dd,J=5.6,13.6 Hz,1H), 2.84(dd,J=9.6, 13.6 Hz,1H), 2.72(t,J=7.4 Hz,2H), 1.60–1.10(m,4H), 0.81 (t,J=7.2 Hz,3H)

(2) Methyl 3-[4-[(5-amidino-2-benzofuranyl)carbonylamino]phenyl]-2-(n-butylsulfonylamino) propionate (compound (40))

In the same manner as in Example 1 (2), 5-cyano-2-benzofurancarboxylic acid (200 mg, 1.07 mmol) and methyl 3-(4-aminophenyl)-2-(n-butylsulfonylamino)propionate (371 mg, 1.18 mmol) were condensed to give 188 mg of methyl 2-(n-butylsulfonylamino)-3-[4-[(5-cyano-2-benzofuranyl)carbonylamino]phenyl]propionate as a yellow solid (36%).

$^1$H-NMR (DMSO-d$_6$) $\delta_{TMS}$: 10.63(s,1H), 8.36(s,1H), 8.00–7.30(m,7H), 4.22–3.97(m,1H), 3.66(s,3H), 3.00–2.60 (m,4H), 1.50–1.05(m,4H), 0.85–0.65(m,3H)

In the same manner as in Example 1 (3), the cyano group of methyl 2-(n-butylsulfonylamino)-3-[4-[(5-cyano-2-benzofuranyl)carbonylamino]phenyl]propionate (225 mg, 0.466 mmol) was converted to an amidino group and purified by silica gel column chromatography (chloroform/methanol=10/1) to give 89 mg of hydriodide of compound (40) as a yellow solid (30% in 3 steps).

$^1$H-NMR (DMSO-d$_6$) $\delta_{TMS}$: 10.62(s,1H), 8.33(s,1H), 8.20–7.60(m,5H), 7.29(d,2H), 4.30–4.00(m,1H), 3.66(s, 3H), 3.00–2.60(m,4H), 1.50–1.00(m,4H), 0.85–0.70(m,3H)

EXAMPLE 12

3-[4-[(5-Amidino-2-benzofuranyl)carbonylamino]phenyl]-2-(n-butylsulfonylamino)propionic acid (compound (48))

Hydriodide (89 mg, 0.14 mmol) of compound (40) was suspended in tetrahydrofuran (2 ml) and a solution of lithium hydroxide (15.0 mg, 0.34 mmol) dissolved in water (4 ml) was added, which was followed by stirring at room temperature for 1.5 hours. The reaction mixture was washed with ethyl acetate, and the aqueous layer was adjusted to pH 2 with 1N hydrochloric acid and concentrated under reduced pressure. The resulting precipitate was collected by filtration and washed with water to give 35 mg of hydrochloride of compound (48) as a colorless solid (47%).

Melting point: >250° C.

IR(KBr): 3700–2700, 1740, 1660, 1605, 1540 cm$^{-1}$ $^1$H-NMR (DMSO-d$_6$, 500 MHz) $\delta_{TMS}$: 10.67(bs,1H), 9.44(bs,2H), 9.16(bs,2H), 8.00(s,1H), 7.98(d,J=8.6 Hz, 1H), 7.91(dd,J=1.9,8.6 Hz,1H), 7.75(d,2H), 7.60(d,J=9.2 Hz,1H), 7.30(d,2H), 4.00(d,J=5.0 Hz,1H), 3.04(dd,J=5.0,13.8 Hz,1H), 2.77(dd,J=10.0,13.8 Hz, 1H), 2.64(t,J=7.6 Hz,2H), 1.40–1.20(m,2H), 1.20–1.15(m,2H), 0.76(t,J=7.8 Hz,3H)

EXAMPLE 13

(1) t-Butyl 3-(4-aminocyclohexyl)propionate

Tetrahydrofuran (280 ml) was added to (methoxymethyl)triphenylphosphonium chloride (27.8 g, 81.1 mmol) and a solution (50.0 ml, 80.0 mmol) of 1.6M n-butyllithium in n-hexane was dropwise added at −40° C. over 30 minutes, which was followed by stirring for one hour. Then, a solution of 4-(benzyloxycarbonylamino) cyclohexanone (20.0 g, 81.0 mmol) dissolved in tetrahydrofuran (200 ml) was dropwise added over 30 minutes. The mixture was warmed to room temperature and stirred for 3.5 hours. The reaction mixture was poured into a saturated aqueous ammonium chloride solution and the organic layer was separated. The aqueous layer was extracted with ethyl acetate and the extract and the organic layer were combined. The mixture was washed with water and saturated brine, and dried over anhydrous magnesium sulfate. After filtration, low boiling matters were distilled away from the filtrate under reduced pressure and the residue was purified by silica gel column chromatography (n-hexane/ethyl acetate=4/1) to give 7.02 g of 4-(benzyloxycarbonylamino)cyclohexylidenemethyl methyl ether as a colorless solid (32%).

IR (neat): 3600–3100, 2900, 1670, 1530, 1300 cm$^{-1}$ $^1$H-NMR (CDCl$_3$) $\delta_{TMS}$: 7.33(m,5H), 5.77(s,1H), 5.10(s, 2H), 4.69(bs,1H), 3.63(m,1H), 3.53(s,3H), 2.20–1.80(m, 6H), 1.34–1.05(m,2H)

4-(Benzyloxycarbonylamino)cyclohexylidenemethyl methyl ether (7.00 g, 25.5 mmol) was dissolved in tetrahydrofuran (50 ml) and 4N hydrochloric acid (25 ml) was added, which was followed by stirring at room temperature for 4 hours. The reaction mixture was made weak alkaline with a saturated aqueous sodium hydrogencarbonate solution and extracted with ethyl acetate. The extract was washed with water and saturated brine, and dried over anhydrous magnesium sulfate. After filtration, low boiling matters were distilled away from the filtrate under reduced pressure to give 6.25 g of 4-(benzyloxycarbonylamino) cyclohexylcarbaldehyde as a colorless solid (94%)

$^1$H-NMR (CDCl$_3$) $\delta_{TMS}$: 9.65, 9.61(each s,1H), 7.34(m, 5H), 5.02(s,2H), 4.73(m,1H), 3.50(m,1H), 2.30–1.10(m, 9H)

Sodium hydride (60%, 1.17 g, 28.9 mmol) was suspended in tetrahydrofuran (240 ml) and a solution of t-butyl diethylphosphonoacetate (95% purity, 6.15 g, 25.8 mmol) dissolved in tetrahydrofuran (60 ml) was dropwise added over 15 minutes under ice-cooling. The mixture was warmed to room temperature and stirred for 30 minutes. The reaction mixture was again ice-cooled and a solution of 4-(benzyloxycarbonylamino)cyclohexylcarbaldehyde (6.15 g, 23.4 mmol) in tetrahydrofuran (60 ml) was dropwise added over 45 minutes, which was followed by stirring at room temperature for one hour. Low boiling matters were distilled away from the reaction mixture under reduced pressure, and ethyl acetate and saturated brine were added to the residue. The organic layer was separated, washed with water and saturated brine, and dried over anhydrous magnesium sulfate. After filtration, low boiling matters were distilled away from the filtrate under reduced pressure. The residue was purified by silica gel column chromatography (n-hexane/ethyl acetate=4/1) to give 7.02 g of t-butyl β-[4-(benzyloxycarbonylamino)cyclohexyl] acrylate as a colorless solid (32%).

IR(KBr): 3700–3100, 2900, 1710, 1700, 1650, 1510 cm$^{-1}$ $^1$H-NMR (CDCl$_3$) $\delta_{TMS}$: 7.34(m,5H), 6.83(dd,J=6.8,15.8 Hz,0.5H), 6.75(dd,J=6.8,15.8 Hz,0.5H), 5.72(dd,J=1.3,15.8 Hz,0.5H), 5.68(dd,J=1.3,15.8 Hz,0.5H), 5.08(s,2H), 4.85, 4.75(each bs,1H), 3.81, 3.45(each bs,1H), 1.48(s,9H), 2.30–1.10(m,8H)

t-Butyl β-[4-(benzyloxycarbonylamino)cyclohexyl] acrylate (7.00 g, 19.5 mmol) was dissolved in methanol (200 ml) and 10% palladium-carbon (700 mg) was added. The mixture was stirred at room temperature for 24 hours under a hydrogen atmosphere. The reaction mixture was filtrated and low boiling matters were distilled away from the filtrate under reduced pressure. The residue was washed with a mixed solution of n-hexane and ethyl acetate to give 3.78 g of t-butyl 3-(4-aminocyclohexyl)propionate as a colorless solid (85%).

Melting point: 39°–40° C.

IR(KBr) :2900, 1720, 1360, 1160 cm$^{-1}$ $^1$H-NMR (CDCl$_3$) $\delta_{TMS}$: 8.00(bs,2H), 2.88(m,1H), 2.19 (m,2H), 1.91(d,J=9.9 Hz,2H), 1.73(d,J=9.9 Hz,2H), 1.39(s, 9H), 1.60–0.80(m,8H)

(2) Methyl 3-[4-[(5-amidino-2-benzofuranyl) carbonylamino]cyclohexyl ]propionate (compound (158))

In the same manner as in Example 1 (2), 5-cyano-2-benzofurancarboxylic acid (203 mg, 1.08 mmol) and t-butyl 3-(4-aminocyclohexyl)propionate (295 mg, 1.30 mmol) were condensed and purified by silica gel column chromatography (n-hexane/ethyl acetate=2/1) to give 165 mg of t-butyl 3-[4-[(5-cyano-2-benzofuranyl)carbonylamino] cyclohexyl]propionate as a colorless solid (38%).

IR(KBr): 2910, 2210, 1715, 1680, 1595, 1505, 1455, 885 cm$^{-1}$ $^1$H-NMR (CDCl$_3$) $\delta_{TMS}$: 8.04(s,1H), 7.71–7.57(m,2H), 7.50(s,1H), 6.68, 6.42(each d,J=8.0 Hz, 1H), 4.29–4.21, 3.98–3.90(each m,1H), 2.30–1.08(m,13H), 1.45(s,9H)

t-Butyl 3-[4-[(5-cyano-2-benzofuranyl)carbonylamino] cyclohexyl ]propionate (160 mg, 0.403 mmol) was dissolved in methanol (40 ml) and the solution was ice-cooled. Hydrogen chloride gas was blown in for 20 minutes, which was followed by stirring for 3 hours. Low boiling matters were distilled away from the reaction mixture under reduced pressure, and chloroform (20 ml) and a saturated aqueous sodium hydrogencarbonate solution (20 ml) were added to the obtained residue. The mixture was stirred for 30 minutes. The organic layer was partitioned and the aqueous layer was extracted with chloroform. The extract and the organic layer were combined, washed with water and saturated brine, and dried over anhydrous magnesium sulfate. After filtration, low boiling matters were distilled away from the filtrate under reduced pressure and ammonium chloride (60 mg, 1.12 mmol), a solution (10 ml) of ammonia in methanol, and methanol (20 ml) were added to the residue. The mixture was refluxed under heating for 3 hours. Low boiling matters were distilled away from the reaction mixture under reduced pressure, and the residue was purified by silica gel column chromatography (chloroform/methanol=95/5-85/15) to give 54 mg of hydrochloride of compound (158) as a colorless solid (33% in 2 steps).

$^1$H-NMR (DMSO-d$_6$, 500 MHz) $\delta_{TMS}$: 8.66, 8.48(each d,J=7.6 Hz,1H), 8.33–8.31(m1H), 7.92–7.88(m,2H), 7.78, 7.75(each s,1H), 4.09–3.72(m,1H), 3.60, 3.59(each s,3H), 2.33(t,J=8.2 Hz,2H), 1.85–0.97(m,1H)

EXAMPLE 14

3-[4-[(5-Amidino-2-benzofuranyl)carbonylamino] cyclohexyl]propionic acid (compound (165))

In the same manner as in Example 10, hydrochloride (50 mg, 0.12 mmol) of compound (158) was hydrolyzed with a 1N aqueous sodium hydroxide solution (2.0 ml, 2.0 mmol) to give 14 mg of hydrochloride of compound (165) as a colorless solid (29%).

Melting point: >250° C.

IR(KBr): 3250, 3050, 2910, 1670, 1635, 1590, 1520, 1450 cm$^{-1}$ $^1$H-NMR (DMSO-d$_6$) $\delta_{TMS}$: 9.41(bs,2H), 9.16(bs,2H), 8.65, 8.50(each d,J=8.5 Hz,1H), 7.9–7.84(m,2H), 7.76, 7.73 (each s,1H), 3.93–3.76(m1H), 2.24(t,J=7.5 Hz,2H), 1.88–0.98(m,11H)

EXAMPLE 15

(1) Ethyl 4-aminophenoxyacetate

4-Nitrophenol (25.0 g, 180 mmol) and ethyl bromoacetate (20.0 ml, 180 mmol) were dissolved in N,N-dimethylformamide (40 ml), and potassium carbonate (27.4 g, 198 mmol) was added. The mixture was stirred at room temperature for 16 hours under a nitrogen atmosphere. The reaction mixture was poured into water (100 ml) and extracted with an equivalent mixture of n-hexane and ethyl acetate. The extract was washed with water and saturated brine, and dried over anhydrous magnesium sulfate. After filtration, low boiling matters were distilled away from the filtrate under reduced pressure to quantitatively give 40.5 g of ethyl 4-aminophenoxyacetate as a colorless solid.

IR(KBr): 3700–2900, 1755, 1590, 1500 cm$^{-1}$ $^1$H-NMR (DMSO-d$_6$) $\delta_{TMS}$: 8.25–8.16(m,2H), 7.20–7.12 (m,2H), 4.99(s,2H), 4.18(q,J=7.1 Hz,2H), 1.22(t,J=7.1 Hz,3H)

(2) 5-(Benzyloxycarbonylamidino)-2-benzofurancarboxylic acid

Ethanol (100 ml) was added to ethyl 5-cyano-2-benzofurancarboxylate (4.0 g, 18.6 mmol) and the mixture was ice-cooled. Hydrogen chloride gas was blown in for 15 minutes and the mixture was stirred at room temperature for 14 hours. Low boiling matters were distilled away from the reaction mixture under reduced pressure and the residue was dissolved in chloroform (200 ml). A saturated aqueous sodium hydrogencarbonate solution (200 ml) was added and the mixture was stirred for 10 minutes. The organic layer was partitioned, washed with water and saturated brine, and dried over anhydrous magnesium sulfate. After filtration, low boiling matters were distilled away from the filtrate under reduced pressure to quantitatively give 4.85 g of ethyl 5-[(1-ethoxy)iminomethyl]-2-benzofurancarboxylate as a yellow solid.

IR(KBr): 3700–3100, 2950, 1710, 1635, 1575 cm$^{-1}$ $^1$H-NMR (DMSO-d$_6$, 500 MHz) $\delta_{TMS}$: 8.28(d,J=1.8 Hz,1H), 8.04(dd,J=1.8,8.8 Hz,1H), 7.82(s,1H), 7.78(d,J=8.8 Hz,1H),4.38(q,J=7.2 Hz,2H), 4.27(q,J=7.1 Hz,2H), 1.40–1.30 (m,6H)

Ammonium chloride (1.05 g, 19.5 mmol), a solution (14.2 ml) of ammonia in ethanol, and ethanol (100 ml) were added to ethyl 5-[(1-ethoxy) iminomethyl]-2-benzofurancarboxylate (4.85 g, 18.6 mmol), and the mixture was refluxed under heating for 2 hours in a nitrogen atmosphere. Low boiling matters were distilled away from the reaction mixture under reduced pressure and the residue was washed with diethyl ether to give 4.85 g of hydrochloride of ethyl 5-amidino-2-benzofurancarboxylate as a pale-yellow solid (97%).

IR(KBr): 3600–2800, 1710, 1690, 1650 cm$^{-1}$ $^1$H-NMR (DMSO-d$_6$, 500 MHz) $\delta_{TMS}$: 10.00–8.40(bs, 4H), 8.34(s,1H), 8.00(d,J=8.9 Hz,1H), 7.97–7.93(m,2H), 4.39(d,J=7.2 Hz,2H), 1.36(t,J=7.2 Hz,3H)

Tetrahydrofuran (7.5 ml) and a 1N aqueous sodium hydroxide solution (7.5 ml, 7.5 mmol) were added to hydrochloride (1.00 g, 3.72 mmol) of ethyl 5-amidino-2-benzofurancarboxylate, and the mixture was stirred at room temperature for one hour. The reaction mixture was concentrated under reduced pressure to about 1/2 and washed with chloroform. The aqueous layer was adjusted to pH 2–3 with 1N hydrochloric acid. The resulting precipitate was collected by filtration and washed with water to give 791 mg of hydrochloride of 5-amidino-2-benzofurancarboxylic acid as a pale-yellow solid (88%).

IR(KBr): 3600–2600, 1710, 1690, 1610, 1570 cm$^{-1}$ $^1$H-NMR (DMSO-d$_6$, 500 MHz) $\delta_{TMS}$: 9.52(bs,2H), 9.38 (bs,2H), 8.34(d,J=1.7 Hz,1H), 7.97(d,J=8.8 Hz,1H), 7.94 (dd,J=1.7,8.8 Hz,1H), 7.84(s,1H)

Tetrahydrofuran (200 ml) was added to hydrochloride (7.55 g, 31.4 mmol) of 5-amidino-2-benzofurancarboxylic acid, and the mixture was ice-cooled. The mixture was maintained at pH 10 with a 1N aqueous sodium hydroxide solution while dropwise addition of benzyloxycarbonyl chloride (6.74 ml, 47.0 mmol) over about 15 minutes. The mixture was stirred for 30 minutes and then at room temperature for 2 hours. The reaction mixture was concentrated under reduced pressure. The resulting precipitate was collected by filtration, and washed with water and an equivalent mixture of n-hexane and ethyl acetate to give 7.94 g of 5-(benzyloxycarbonylamidino)-2-benzofurancarboxylic acid as a pale-yellow solid (75%).

IR(KBr): 3600–2900, 1650, 1600, 1560 cm$^{-1}$ $^1$H-NMR (DMSO-d$_6$) $\delta_{TMS}$: 9.23(bs,2H), 8.32(d,J=1.7 Hz,1H), 7.96(dd,J=1.7,8.8 Hz,1H), 7.61 (d,J=8.8 Hz,1H), 7.45–7.30(m,5H), 7.07(s,1H), 5.12(s,2H)

(3) Ethyl 4-[[(5-(benzyloxycarbonylamidino)-2-benzofuranyl]carbonylamino]phenoxyacetate (compound (2))

5-(Benzyloxycarbonylamidino)-2-benzofurancarboxylic acid (2.00 g, 6.18 mmol) and ethyl 4-aminophenoxyacetate (1.32 g, 6.79 mmol) were dissolved in N,N-dimethylformamide (100 ml), and 1-hydroxy-1H-benzotriazole (919 mg, 6.79 mmol) and 1-(3-dimethylaminopropyl)-3-ethylcarbodiimide (1.30 g, 6.79 mmol) were added. The mixture was stirred at room temperature for 14 hours. Water (250 ml) was added to the reaction mixture, and the resulting precipitate was collected by filtration and washed with water to give 2.73 g of compound (2) as a colorless solid (91%).

IR(KBr): 3700–3000, 1750, 1650, 1605 cm$^{-1}$ $^1$H-NMR (DMSO-d$_6$) $\delta_{TMS}$: 10.51 (bs,1H), 9.23(bs,2H), 8.49(d,J=1.4 Hz,1H), 8.11 (dd,J=1.4,8.8 Hz,1H), 7.85–7.80 (m,2H), 7.73–7.65(m,2H), 6.99–6.92(m,2H), 5.13(s,2H), 4.77(s,2H), 4.17(q,J=7.0 Hz,2H), 1.22(t,J=7.0 Hz,3H) MS (SIMS) (m/z) 516 (MH$^+$)

EXAMPLE 16

4-[[(5-(Benzyloxycarbonylamidino)-2-benzofuranyl] carbonylamino]phenoxyacetic acid (compound (4))

In the same manner as in Example 10, compound (2) (540 mg, 1.05 mmol) was hydrolyzed to give 493 mg of compound (4) as a yellow solid (96%).

IR(KBr): 3700–2400, 1740, 1670 cm$^{-1}$ $^1$H-NMR (DMSO-d$_6$) $\delta_{TMS}$: 10.57(s,1H), 8.39(s,1H), 8.05–7.85(m,3H), 7.72–7.66(m,2H), 7.47–7.37(m,5H), 6.97–6.90(m,2H), 5.29(s,2H), 4.67(s,2H)

EXAMPLE 17

Ethyl 4-[(5-amidino-2-benzofuranyl)carbonylamino] phenoxyacetate (compound (7))

Tetrahydrofuran (300 ml), 1N hydrochloric acid (7 ml, 7 mmol) and 10% palladium-carbon were added to compound (2) (2.70 g, 5.24 mmol). The mixture was stirred at room temperature for 2 hours under a hydrogen atmosphere. The reaction mixture was filtered through Celite. Low boiling matters were distilled away from the filtrate under reduced pressure and the residue was purified by silica gel column chromatography (chloroform/methanol=4/1) to give 1.55 g of hydrochloride of compound (7) as a pale-yellow solid (71%).

IR(KBr) :3700–2800, 1740, 1680, 1650 cm$^{-1}$ $^1$H-NMR (DMSO-d$_6$) $\delta_{TMS}$: 10.70(bs,1H), 9.35(bs,4H), 8.36(d,J=1.0 Hz,1H), 8.00–7.90(m,3H), 7.76–7.70(m,2H), 6.93–6.70(m,2H), 4.77(s,2H), 4.17(q,J=7.1 Hz,2H), 1.23(t, J=7.1 Hz,3H)

EXAMPLE 18

Ethyl 4-[(5-benzylamidino-2-benzofuranyl)carbonylamino] phenoxyacetate (compound (1))

5-Cyano-2-benzofurancarboxylic acid (830 mg, 4.43 mmol) and ethyl 4-aminophenoxyacetate (910 mg, 4.66 mmol) were dissolved in N,N-dimethylformamide (40 ml), and 1-hydroxy-1H-benzotriazole (630 mg, 4.66 mmol) and 1-(3-dimethylaminopropyl)-3-ethylcarbodiimide (893 mg, 4.66 mmol) were added. The mixture was stirred at room temperature for 13 hours. Water (100 ml) was added to the reaction mixture. The resulting precipitate was collected by filtration and washed with water to give 1.49 g of ethyl 4-[(5-cyano-2-benzofuranyl)carbonylamino] phenoxyacetate as a colorless solid (92%).

$^1$H-NMR (DMSO-d$_6$) $\delta_{TMS}$: 10.59(s,1H), 8.43(s,1H), 7.93(s,2H), 7.84(s,1H), 7.70(d,J=9.0 Hz,2H), 6.95(d,J=9.0 Hz,2H), 4.18(q,J=7.1 Hz,2H), 1.22(t,J=7.1 Hz,3H)

Ethyl 4-[(5-cyano-2-benzofuranyl)carbonylamino] phenoxyacetate (1.49 g, 4.09 mmol) was dissolved in a mixed solvent of pyridine (50 ml) and triethylamine (5 ml). A hydrogen sulfide gas was blown in for 10 minutes at room temperature and the mixture was stirred for 16 hours. Low boiling matters were distilled away from the reaction mixture under reduced pressure to give ethyl 4-[(5-thiocarbamoyl-2-benzofuranyl)carbonylamino] phenoxyacetate as a yellow solid. Acetone (100 ml) and iodomethane (10 ml) were added to this solid, and the mixture was refluxed under heating for 2 hours. The reaction mixture was heated to room temperature. The resulting precipitate was collected by filtration to give ethyl 4-[[5-[(1-methylthio)iminomethyl]-2-benzofuranyl] carbonylamino]phenoxyacetate as a yellow solid. To this solid was added ethanol (50 ml) and benzylamine (0.5 ml, 4.6 mmol), and the mixture was refluxed under heating for 2 hours. The reaction mixture was concentrated to about 10 ml under reduced pressure, and diethyl ether (40 ml) was added. The resulting precipitate was collected by filtration to give 1.70 g of hydriodide of compound (1) as a yellow solid (69% in three steps).

$^1$H-NMR (DMSO-d$_6$) $\delta_{TMS}$: 10.57(s,4H), 9.82–9.55(m, 3H), 8.31 (d,J=2.0 Hz,1H), 7.98(d,J=9.0 Hz,1H), 7.91 (s,1H), 7.86(dd,J=2.0,9.0 Hz,4H), 7.71(d,J=9.0 Hz,2H), 7.47–7.36(m,5H), 6.96(d,J=9.0 Hz,2H), 4.78(s,2H), 4.71(s, 2H), 4.18(q,J=7.4 Hz,2H), 1.22(t,J=7.4 Hz,3H)

EXAMPLE 19

4-[(5-Benzylamidino-2-benzofuranyl)carbonylamino] phenoxy-acetic acid (compound (5))

In the same manner as in Example 10, hydriodide (502 mg, 0.837 mmol) of compound (1) was hydrolyzed to that of Example 10 to quantitatively give 400 mg of hydrochloride of compound (5) as a colorless solid.

$^1$H-NMR (DMSO-d$_6$) $\delta_{TMS}$: 10.66(s,1H), 10.30–9.30(m, 3H), 8.34(s,1H), 7.97–7.87(m,3H), 7.71(d,J=9.0 Hz,2H), 7.52–7.32(m,5H), 6.90(d,J=9.0 Hz,2H), 4.75(s,2H), 4.58 (s, 2H)

EXAMPLE 20

(1) 6-Amidino-2-benzofurancarboxylic acid

A method similar to that of Example 15 (2) was applied. That is, ethyl 6-cyano-2-benzofurancarboxylate (135 mg, 0.628 mmol) was allowed to react with ethanol in the presence of hydrogen chloride to give 137 mg of ethyl 6-[(1-ethoxy)iminomethyl)]-2-benzofurancarboxylate as an orange solid (84%).

$^1$H-NMR (CDCl$_3$) $\delta_{TMS}$: 8.03–8.02(m,1H), 7.30–7.20(m, 1H), 7.53(s,1H), 4.45(q,J=7.1 Hz,2H), 4.36(q,J=7.1 Hz,2H), 1.50–1.40(m,6H)

Ethyl 6-[(1-ethoxy)iminomethyl)]-2-benzofurancarboxylate (137 mg, 0.525 mmol) was allowed to react with ammonia to give 132 mg of ethyl 6-amidino-2-benzofurancarboxylate hydrochloride as a yellow solid (94%).

$^1$H-NMR (DMSO-d$_6$) $\delta_{TMS}$: 9.33(bs,4H), 8.26(s,1H), 8.01 (d,J=8.4 Hz,1H), 7.87(d,J=1.4 Hz,1H), 7.76(dd,J=1.4, 8.6 Hz,1H), 4.38(q,J=7.2 Hz,2H), 1.34(t,J=7.2 Hz,3H)

Ethyl 6-amidino-2-benzofurancarboxylate hydrochloride (129 mg, 0.480 mmol) was hydrolyzed with a 1N aqueous sodium hydroxide solution to give 65 mg of 6-amidino-2-benzofurancarboxylic acid hydrochloride as a brown solid (56%).

IR(KBr): 3700–2700, 1680, 1590 cm$^{-1}$ $^1$H-NMR (DMSO-d$_6$) $\delta_{TMS}$: 9.46(bs,2H), 9.18(bs,2H), 8.24(s,1H), 8.02(d,J=8.3 Hz,1H), 7.92–7.74(m,2H)

(2) t-Butyl 4-[(6-amidino-2-benzofuranyl)carbonylamino] phenoxyacetate (compound (9))

In the same manner as in Example 15 (3), 6-amidino-2-benzofurancarboxylic acid hydrochloride (63 mg, 0.26 mmol) and t-butyl 4-aminophenoxyacetate (66 mg, 0.30 mmol) were condensed and purified by silica gel column chromatography (chloroform/methanol=100/3-3/1) to give 109 mg of hydrochloride of compound (9) as a colorless solid (9 1%).

IR(KBr): 1750, 1710, 1630 cm$^{-1}$ $^1$H-NMR (DMSO-d6) $\delta_{TMS}$: 10.65(bs,1H), 8.20(s,1H), 8.05(d,J=7.8 Hz,1H), 7.90(s,1H), 7.80–7.60(m,3H), 6.97–6.90(m,2H), 4.65(m,2H), 1.44(s,9H)

EXAMPLE 21

4-[(6-Amidino-2-benzofuranyl)carbonylamino] phenoxyacetic acid (compound (12))

In the same manner as in Example 2, hydrochloride (109 mg, 2.45 mmol) of compound (9) was treated with trifluoroacetic acid (2.5 ml) to quantitatively give 96 mg of hydrochloride of compound (12) as a pale-yellow solid.

Melting point: >250° C.

IR(KBr): 3700–2800, 1730, 1690, 1520, 1505 cm$^{-1}$ $^1$H-NMR (DMSO-d$_6$, 500 MHz) $\delta_{TMS}$: 10.63(bs, 1H), 9.45(bs,2H), 9.32(bs,2H), 8.20(s,1H), 8.06(d,J=8.3 Hz,1H), 7.89(d,J=1.6 Hz,1H), 7.79(dd,J=1.6,8.3 Hz,1H), 7.72–7.69 (m,2H), 6.97–6.93(m,2H), 4.67(s,2H)

EXAMPLE 22

(1) t-Butyl trans-(4-aminocyclohexyloxy)acetate

To a mixture of trans-4-aminocyclohexanol (5.00 g, 43.4 mmol), N,N-dimethylurea (3.82 g, 43.4 mmol), 37% formalin (50 ml), N-methylmorpholine (9.54 ml, 86.8 mmol) and dioxane (10 ml) was added toluene (200 ml), and the mixture was heated for about 5 hours while removing water for azeotropic distillation. Low boiling matters were distilled away from the reaction mixture under reduced pressure, and the residue was purified by silica gel column chromatography (methylene chloride/methanol=50/1-10/1) to give 7.40 g of trans-5-(4-hydroxycyclohexyl)-1,3-dimethylhexahydro-2-oxo-1,3,5-triazine as colorless solid (75%).

$^1$H-NMR (CDCl$_3$) $\delta_{TMS}$: 4.21 (s,4H), 3.68–3.55(m,1H), 3.46(d,J=4.6 Hz,1H), 2.85(s,6H), 2.90–2.74(m,1H), 2.13–1.88(m,4H), 1.46–1.23(m,4H)

trans-5-(4-Hydroxycyclohexyl)-1,3-dimethylhexahydro-2-oxo-1,3,5-triazine (1.00 g, 4.40 mmol) and t-butyl bromoacetate (1.29 g, 6.60 mmol) were dissolved in toluene (13 ml), and tetra-n-butylammonium hydrogensulfate (45 mg, 0.13 mmol) was added to the mixture. A solution of sodium hydroxide (13.2 g, 330 mmol) dissolved in water (13.2 ml) was dropwise added, and the mixture was stirred at room temperature for 15 hours. The organic layer was partitioned, washed with water and dried over anhydrous magnesium sulfate. After filtration, low boiling matters were distilled away from the filtrate under reduced pressure, and the residue was purified by silica gel column chromatography (methylene chloride/methanol=20/1) to give 680 mg of trans-5-[4-[(t-butoxycarbonyl)methyloxy]cyclohexyl]-1,3-dimethylhexahydro-2-oxo-1,3,5-triazine as a colorless solid $^1$H-NMR (CDCl$_3$) $\delta_{TMS}$: 4.20(s,4H), 3.98(s,2H), 3.49–3.23(m,1H), 2.84(s,6H), 2.88–2.75(m,1H), 2.18–2.06 (m,2H), 2.06–1.93(m,2H), 1.47(s,9H), 1.44–1.16 (m,4H)

trans-5-[4-[(t-Butoxycarbonyl)methyloxy]cyclohexyl]-1,3-dimethylhexahydro-2-oxo-1,3,5-triazine (300 mg, 0.879 mmol) was dissolved in t-butanol (5 ml) and a saturated aqueous ammonium chloride solution (5 ml) was added, which was followed by refluxing under heating for 2 hours. The reaction mixture was adjusted to pH 10 with a 1N aqueous sodium hydroxide solution and extracted with benzene. The extract was washed with water and saturated brine, and dried over anhydrous sodium sulfate. After filtration, low boiling matters were distilled away from the filtrate under reduced pressure and the residue was purified by silica gel column chromatography (methylene chloride/methanol=10/1-5/1) to give 130 mg of t-butyl trans-(4-aminocyclohexyloxy)acetate as a colorless solid (57%).

$^1$H-NMR (CDCl$_3$) $\delta_{TMS}$: 3.98(s,2H), 4.24–3.42(m,1H), 2.88–2.69(m,1H), 2.45–1.82(m,6H), 1.47(s,9H), 1.50–1.07 (m,4H)

(2) t-Butyl trans[4-[[5-(benzyloxycarbonylamidino)-2-benzofuranyl]-carbonylamino]cyclohexyloxy]acetate (compound (170))

In the same manner as in Example 15 (3), 5-(benzyloxycarbonyl-amidino)-2-benzofurancarboxylic acid (183 mg, 0.541 mmol) and t-butyl trans-(4-aminocyclohexyloxy)acetate (124 mg, 0.541 mmol) were condensed, and purified by silica gel column chromatography (methylene chloride/methanol=30/1-10/1) to give 251 mg of compound (170) as a colorless solid (84%).

$^1$H-NMR (CDCl$_3$) $\delta_{TMS}$: 8.21(d,J=1.3 Hz,1H), 7.95(dd, J=1.3,8.8 Hz,1H), 7.60–7.27(m,7H), 6.45(d,J=8.0 Hz, 1H), 5.22(s,2H), 4.00(s,2H), 4.05–3.92(m,1H), 3.48–3.30(m,1H), 2.25–2.17(m,4H), 1.48(s,9H), 1.60–1.24(m,4H)

EXAMPLE 23 trans-[4-[(5-Amidino-2-benzofuranyl)carbonylamino] cyclohexyloxy]acetic acid (compound (179))

t-Butanol (13 ml) and 10% palladium-carbon (20 mg) were added to compound (170) (135 mg, 0.246 mmol) and the mixture was refluxed under heating for 7 hours under a hydrogen atmosphere. The reaction mixture was filtered through Celite and low boiling matters were distilled away from the filtrate under reduced pressure. Trifluoroacetic acid (1 ml) was added to the residue and the mixture was stirred at room temperature for one hour. Diethyl ether was added to the reaction mixture and the resulting precipitate was collected by filtration and washed with diethyl ether to give 103 mg of trifluoroacetate of compound (179) as a colorless solid (88%).

$^1$H-NMR (DMSO-d$_6$, 500 MHz) $\delta_{TMS}$: 2.90–12.00(m, 1H), 9.36(bs,2H), 9.18(bs,2H), 8.64(d,J=8.0 Hz,1H), 8.28(s, 1H), 7.97–7.82(m,2H), 7.71(s,1H), 4.03(s,2H), 3.90–3.65 (m1H), 3.55–3.25(m,1H), 2.13–1.96(m,2H), 1.96–1.81(m, 2H), 1.57–1.11(m,4H)

Trifluoroacetate (100 mg, 0.211 mmol) of compound (179) was dissolved in acetic acid (5 ml) at 70° C. Concentrated sulfuric acid (31 mg, 0.317 mmol) was gradually added, and the mixture was stirred as it was for 30 minutes. The reaction mixture was heated to room temperature and diethyl ether (20 ml) was added. The precipitated sediment was washed with diethyl ether and collected by filtration to give 92 mg of sulfide of compound (179) as a colorless solid (95%).

$^1$H-NMR (DMSO-de) $\delta_{TMS}$: 9.35(bs,2H), 8.94(bs,2H), 8.64(d,J=8.0 Hz, 1H), 8.28(d,J=1.8 Hz,1H), 7.92(d,J=8.8 Hz,1H), 7.84(dd,J=8.8, 1.8 Hz,1H), 7.72(s,1H), 4.04(s,2H), 3.95–3.65(m,1H), 3.45–3.20 (m,1H), 2.15–1.75(m,4H), 1.60–1.15(m,4H)

EXAMPLE 24

(1) 5-Guanidino-2-benzofurancarboxylic acid

Ethanol (30 ml) and cyanamide (298 mg, 7.09 mmol) were added to hydrochloride (856 mg, 3.54 mmol) of ethyl 5-amino-2-benzofurancarboxylate, and the mixture was stirred with heating at about 50° C. for 24 hours. Low boiling matters were distilled away from the reaction mixture under reduced pressure and the residue was purified by silica gel column chromatography (chloroform/methanol=100/3-3/1) to give 902 mg of ethyl 5-guanidino-2-benzofurancarboxylate as a colorless solid (90%).

IR(KBr): 2500, 1720, 1670, 1630, 1600, 1560 cm$^{-1}$ $^1$H-NMR (DMSO-d$_6$) $\delta_{TMS}$: 8.00–7.90(m,2H), 7.68(d,J= 2.1 Hz, 1H), 7.38(dd,J=2.1,8.6 Hz,1H), 8.00–7.00(bs,2H), 4.38(q,J=7.2 Hz,2H), 1.35(t,J=7.2 Hz,3H) Hydrochloride (900 mg, 3.18 mmol) of ethyl 5-guanidino-2-benzofurancarboxylate was suspended in tetrahydrofuran (8 ml), and a 1N aqueous sodium hydroxide solution (8.0 ml, 8.0 mmol) was added, which was followed by stirring at room temperature for 2 hours. The reaction mixture was adjusted to pH 2–3 with 1N hydrochloric acid and concentrated under reduced pressure. The precipitate was collected by filtration and washed with water to give 336 mg of hydrochloride of 5-guanidino-2-benzofurancarboxylic acid as a colorless solid IR(KBr): 3700–3000, 2300, 1720, 1685, 1630 cm$^{-1}$ $^1$H-NMR (DMSO-d$_6$) $\delta_{TMS}$: 10.07(bs,1H), 7.80–7.30(bs, 1H), 7.77(d,J=8.9 Hz,1H), 7.70–7.65(m,2H), 7.37(dd,J=2.2, 8.9 Hz,1H)

(2) t-Butyl 4-[(5-guanidino-2-benzofuranyl)carbonylamino] phenoxyacetate (compound (83))

5-Guanidino-2-benzofurancarboxylic hydrochloride (100 mg, 0.391 mmol) and t-butyl 4-aminophenoxyacetate (96.0 mg, 0.431mmol) were dissolved in N,N-dimethylformamide (4 ml). 1-Hydroxy-1H-benzotriazole (58.2 mg, 0.431 mmol) and diisopropylcarbodiimide (54.3 mg, 0.431 mmol) were added and the mixture was stirred at about 50° C. for 15 hours. Low boiling matters were distilled away from the reaction mixture under reduced pressure and the residue was purified by silica gel column chromatography (chloroform/methanol=100/3-3/1) to give 144 mg of hydrochloride of compound (83) as a colorless solid (80%).

IR(KBr): 3700–3000, 1740, 1600, 1605, 1510 cm$^{-1}$ $^1$H-NMR (DMSO-d$_6$) $\delta_{TMS}$: 10.53(bs,1H), 7.79–7.65(m, 3H), 7.65–7.40(bs,4H), 7.34(dd,J=2.1,9.0 Hz,1H), 6.95–6.87(m,2H), 4.64(s,2H), 1.44(s,9H)

EXAMPLE 25

4-[(5-Guanidino-2-benzofuranyl)carbonylamino] phenoxyacetic acid (compound (84))

In the same manner as in Example 2, hydrochloride (140 mg, 0.304 mmol) of compound (83) was treated with trifluoroacetic acid (2.8 ml) to quantitatively give 123 mg of hydrochloride of compound (84) as a pale-yellow solid.

Melting point: 135°–145° C. (dec.)

IR(KBr) :3700–3000, 1670, 1510 cm$^{-1}$ $^1$H-NMR (DMSO-d$_6$, 500 MHz) $\delta_{TMS}$: 10.50(bs,1H), 9.97(bs,1H), 7.79–7.77(m,2H), 7.73–7.70(m,3H), 7.65–7.36 (bs,4H), 7.35(dd,J=2.2,8.9 Hz, 1H), 6.95–6.92(m,2H), 4.66 (s,2H)

EXAMPLE 26 t-Butyl 4-[(6-amidino-2-indolyl)carbonylamino] phenoxyacetate (compound (93))

In the same manner as in Example 1 (2), 6-cyano-2-indolcarboxylic acid (295 mg, 1.59 mmol) and t-butyl 4-aminophenoxyacetate (386 mg, 1.74 mmol) were condensed and purified by silica gel column chromatography (n-hexane/ethyl acetate=1/2) to quantitatively give 622 mg of t-butyl 4-[(6-cyano-2-indolyl)carbonylamino] phenoxyacetate as a pale-brown solid.

IR(KBr) :3700–2900, 2200, 1730, 1650, 1540 cm$^{-1}$ $^1$H-NMR (DMSO-d,) $\delta_{TMS}$: 12.23(bs,1H), 10.32(bs,1H), 8.00–7.85(m,2H), 7.68(d,2H), 7.55–7.35(m,2H), 6.94(d, 2H), 4.64(s,2H), 1.44(s,9H)

In the same manner as in Example 1 (3), the cyano group of t-butyl 4-[(6-cyano-2-indolyl)carbonylamino] phenoxyacetate (630 mg, 1.61 mmol) was converted to an amidino group to give 891 mg of hydriodide of compound (93) as a viscous brown oil (quantitatively in 3 steps).

$^1$H-NMR (DMSO-d$_6$) $\delta_{TMS}$: 10.33(bs,1H), 7.95–7.86(m, 2H), 7.69(d,2H), 7.51(s,1H), 7.43(d,J=9.2 Hz,1H), 6.94(d, 2H), 4.65(s,2H), 1.44(s,9H)

EXAMPLE 27

4-[(6-Amidino-2-indolyl)carbonylamino]phenoxyacetic acid (compound (95))

In the same manner as in Example 2, hydriodide (891 mg, 1.61 mmol) of compound (93) was treated with trifluoroacetic acid (10 ml) to give 489 mg of hydriodide of compound (95) as a brown solid (63%).

Melting point: 205°–245 C. (dec.)

IR(KBr): 3700–3100, 1660, 1520, 1400 cm$^{-1}$ $^1$H-NMR (DMSO-d$_6$, 500 MHz) $\delta_{TMS}$: 10.33(bs,1H), 9.27(bs,2H), 8.82(bs,2H), 7.95(s,1H), 7.91 (d,J=8.4 Hz, 1H), 7.70(d,2H), 7.51(s,1H), 7.45(dd,J=1.3,8.4 Hz, 1H), 6.95(d,2H), 4.67(s,2H)

EXAMPLE 28 t-Butyl 4-[(6-amidino-1-methyl-2-indolyl)carbonylamino] phenoxyacetate (compound (117))

In the same manner as in Example 1 (2), 6-cyano-1-methyl-2-indolcarboxylic acid (52 mg, 0.26 mmol) and t-butyl 4-aminophenoxyacetate (63 mg, 0.29 mmol) were condensed to quantitatively give 109 mg of t-butyl 4-[(6-cyano-1-methyl-2-indolyl)carbonylamino]phenoxyacetate as a colorless solid.

IR(KBr): 3700–3000, 2200, 1740, 1505 cm$^{-1}$ $^{1}$H-NMR (CDCl$_3$) $\delta_{TMS}$: 6.93(d,2H),4.52(s,2H), 4.11(s,3H), 1.50 (s,9H)

In the same manner as in Example 1(3), the cyano group of t-butyl 4-[(6-cyano-1-methyl-2-indolyl)carbonylamino] phenoxyacetate (105 mg, 0.259 mmol) was converted to an amidino group to give 240 mg of hydriodide of compound (117) as a brown solid (quantitatively in 3 steps).

IR(KBr): 3700–2900, 1640, 1400 cm$^{-1}$ $^{1}$H-NMR (DMSO-d$_6$) $\delta_{TMS}$: 10.23(bs,1H), 8.18(s,1H), 7.91(d,J=8.8 Hz, 1H), 7.67(d,2H), 7.54(d,J=8.8 Hz, 1H), 7.36(s,1H), 6.92(d,2H), 4.64(s,2H), 4.09(s,3H), 1.44(s,9H)

EXAMPLE 29

4-[(6-Amidino-1-methyl-2-indolyl)carbonylamino] phenoxyacetic acid (compound (118))

In the same manner as in Example 2, hydriodide (240 mg, 0.26 mmol) of compound (117) was treated with trifluoroacetic acid (2 ml) to quantitatively give 128 mg of hydriodide of compound (118) as a yellow solid.

Melting point: >250° C.

IR(KBr): 3700–2800, 1640, 1505, 1390 cm$^{-1}$ $^{1}$H-NMR (DMSO-d$_6$, 500 MHz) $\delta_{TMS}$: 9.28(bs,2H), 8.90 (bs,2H), 8.19(s, 1H), 7.92(d,J=8.4 Hz, 1H), 7.67(d,2H), 7.54(dd,J=1.5,8.4 Hz, 1H), 7.37(s,1H), 6.94(d,2H), 4.64(s, 2H), 4.09 (s,3H)

EXAMPLE 30 t-Butyl 4-[(5-amidinobenzo[b]thien-2-yl)carbonylamino] phenoxyacetate (compound (131))

In the same manner as in Example 1 (2), 5-cyanobenzo [b]thiene-2-carboxylic acid (520 mg, 2.56 mmol) and t-butyl 4-aminophenoxyacetate (632 mg, 2.82 mmol) were condensed to give 888 mg of t-butyl 4-[(5-cyanobenzo [b]thien-2-yl)carbonylamino]phenoxyacetate as an orange solid (85%).

IR(KBr): 2200, 1740, 1635, 1600, 1500 cm$^{-1}$ $^{1}$H-NMR (DMSO-d$_6$) $\delta_{TMS}$: 10.59(bs,1H), 8.61(d,J=1.5 Hz, 1H), 8.40(s,1H), 8.30(d,J=8.4 Hz, 1H), 7.83(dd,J=1.5, 8.4 Hz,1H), 7.65(d,2H), 6.94(d,2H), 4.65(s,2H), 1.44 (s, 9H)

In the same manner as in Example 1 (3), the cyano group of t-butyl 4-[(5-cyanobenzo[b]thien-2-yl)carbonylamino] phenoxyacetate (850 mg, 2.08 mmol) was converted to an amidino group to give 469 mg of hydriodide of compound (131) as a yellow solid (41% in 3 steps).

IR(KBr): 1755, 1640, 1510, 1230, 1160 cm$^{-1}$ $^{1}$H-NMR (DMSO-d$_6$) $\delta_{TMS}$: 8.45(s,1H), 8.35–8.26(m, 1H), 7.84(d,J=8.4 Hz,1H), 7.66(d,2H), 6.93(d,2H), 4.63(s, 2H), 1.45(s,9H)

EXAMPLE 31

4-[(5-Amidinobenzo[b]thien-2-yl)carbonylamino] phenoxyacetic acid (compound (134))

In the same manner as in Example 2, hydriodide (459 mg, 0.830 mmol) of compound (131) was treated with trifluoroacetic acid (7 ml) to give 338 mg of hydriodide of compound (134) as a brown solid (84%).

Melting point: >210° C. (dec.)

IR(KBr): 3700–2700, 1680, 1640, 1510 cm$^{-1}$ $^{1}$H-NMR (DMSO-d$_6$, 500 MHz) $\delta_{TMS}$: 10.58(bs,1H), 9.42(bs,2H), 9.28(bs,2H), 8.42(m,2H), 8.32(d,J=8.6 Hz,1H), 7.84(dd,J=1.8,8.6 Hz,1H), 7.68–7.65(m,2H), 6.97–6.93(m,2H), 4.67(s,2H)

EXAMPLE 32 t-Butyl 4-[(6-amidinobenzo[b]thien-2-yl)carbonylamino] phenoxyacetate (compound (132))

In the same manner as in Example 1 (2), 6-cyanobenzo [b]thiene-2-carboxylic acid (280 mg, 1.38 mmol) and t-butyl 4-aminophenoxyacetate (341 mg, 1.52 mmol) were condensed and purified by silica gel column chromatography (n-hexane/ethyl acetate=1/3) to give 485 mg of t-butyl 4-[(6-cyanobenzo[b]thien-2-yl)carbonylamino] phenoxyacetate as a yellow solid (90%).

IR(KBr) :2200, 1740, 1635, 1500 cm$^{-1}$ $^{1}$H-NMR (DMSO-d$_6$) $\delta_{TMS}$: 10.6(s,1H), 8.70(s,1H), 8.41 (s,1H), 8.19(d,J=8.4 Hz, 1H), 7.82(dd,J=1.4,8.4 Hz,1H), 7.65(d,2H), 6.93(d,2H), 4.65(s,2H), 1.44 (s, 9H)

In the same manner as in Example 1 (3), the cyano group of t-butyl 4-[(6-cyanobenzo[b]thien-2-yl)carbonylamino] phenoxyacetate (475 mg, 1.22 mmol) was converted to an amidino group to give 462 mg of hydriodide of compound (132) as a yellow solid (68% in 3 steps).

IR(KBr): 3700–2700, 1730, 1635, 1500 cm$^{-1}$ $^{1}$H-NMR (DMSO-d$_6$) $\delta_{TMS}$: 10.58(s,1H), 10.0–8.50(bs, 4H), 8.57(s,1H), 8.43(s,1H), 8.24(d,J=8.5 Hz,1H), 7.81 (d,J=8.5 Hz,1H), 7.66(d,2H), 6.96(d,2H), 4.65(s,2H), 1.44 (s,9H)

EXAMPLE 33

4-[(6-Amidinobenzo[b]thien-2-yl)carbonylamino] phenoxyacetic acid (compound (135))

In the same manner as in Example 2, hydriodide (407 mg, 0.736 mmol) of compound (132) was treated with trifluoroacetic acid (7 ml) to give 345 mg of hydriodide of compound (135) as a red-brown solid (94%).

Melting point: >250° C.

IR(KBr): 3700–2800, 1740, 1680, 1635, 1500 cm$^{-1}$ $^{1}$H-NMR (DMSO-d$_6$, 500 MHz) $\delta_{TMS}$: 10.59(s,1H), 9.41 (bs,2H), 9.21(bs,2H), 8.58(s,1H), 8.44(s,1H), 8.23(d,J=8.5 Hz, 1H), 7.81(dd,J=1.5,8.5 Hz, 1H), 7.67(d,2H), 6.95(d,2H), 4.67(s,2H)

EXAMPLE 34

Ethyl trans-3-[4-[[5-(benzyloxycarbonylamidino)-2-benzofuranyl]carbonylamino]cyclohexyl]propionate (compound (154))

In the same manner as in Example 15 (3), 5-(benzyloxycarbonyl-amidino)-2-benzofurancarboxylic acid (3.98 g, 11.8 mmol) and ethyl trans-3-(4-aminocyclohexyl)propionate (3.00 g, 14.1 mmol) were condensed and purified by silica gel column chromatography (n-hexane/ethyl acetate=1/1-0/1) to give 4.66 g of compound (154) as a colorless solid (76%).

IR (KBr): 1730, 1640, 1600, 1530 cm$^{-1}$ $^{1}$H-NMR (CDCl$_3$, 500 MHz) $\delta_{TMS}$: 8.23(d,J=1.7 Hz, 1H), 7.95(dd,J=8.8,1.7 Hz, 1H), 7.53(d,J=8.8 Hz, 1H), 7.50–7.25 (m,6H), 6.47(d,J=7.0 Hz, 1H), 5.22(s,2H), 4.13(q,J=7.1

Hz,2H), 3.93–3.90(m,1H), 2.38–2.30(m,2H), 2.15–2.05(m, 2H), 1.86–1.80(m,2H), 1.48–1.40(m,2H), 1.32–1.22(m,5H), 1.15–1.00(m,2H)

EXAMPLE 35

Ethyl trans-3-[4-[(5-amidino)-2-benzofuranyl)carbonylamino]cyclohexyl]propionate (compound (159))

In the same manner as in Example 17, compound (154) (2.85 g, 5.48 mmol) was subjected to hydrogen reduction and purified by silica gel column chromatography (chloroform/methanol=4/1) to give 2.18 g of hydrochloride of compound (159) as a colorless solid (94%).

Melting point: >250° C.

IR(KBr): 3700–2600, 1720, 1640, 1520 cm$^{-1}$ $^1$H-NMR (DMSO-d$_6$, 500 MHz) $\delta_{TMS}$: 9.31(bs,1H), 8.67 (d,J=8.1 Hz, 1H), 8.30(d,J=1.8 Hz, 1H), 7.90(d,J=8.7 Hz, 1H), 7.87(dd,J=8.7,1.8 Hz, 1H), 7.74(s,1H), 4.05(q,J=7.1 Hz,2H), 3.78–3.71(m,1H), 2.35–2.26(m,2H), 1.88–1.71(m, 1H), 1.48–1.35(m,1H), 1.2–1.35(m,1H), 1.07–0.97(m,2H)

EXAMPLE 36 trans-3-[4-[(5-Amidino-2-benzofuranyl)carbonylamino] cyclohexyl]propionate (compound (167))

In the same manner as in Example 10, hydrochloride (1.59 g, 3.77 mmol) of compound (159) was hydrolyzed to give 1.45 g of hydrochloride of compound (167) as a pale-brown solid (67%).

Melting point: >250° C.

IR(KBr) :3600–2500, 1700, 1630, 1500 cm$^{-1}$ $^1$H-NMR (DMSO-d$_6$, 500 MHz) $\delta_{TMS}$: 9.47(bs,2H), 9.20 (bs,2H), 8.67(d,J=8.2 Hz,1H), 8.30(d,J=1.4 Hz, 1H), 7.94–7.71(m, 2H), 7.63(s,1H), 3.80–3.69(m,1H), 2.28–2.19 (m,2H), 1.89–1.71(m,4H), 1.49–1.20(m,1H), 1.20–1.10(m, 1H), 1.07–0.95(m,2H)

Hydrochloride (1.00 g, 2.54 mmol) of compound (167) was dissolved in acetic acid (100 ml) at 70° C. and concentrated sulfuric acid (2.71 ml, 50.77 mmol) was gradually added. The mixture was stirred until the precipitated crystals dissolved again. The reaction mixture was cooled to room temperature and diethyl ether (200 ml) was added. The precipitated sediment was washed with diethyl ether and collected by filtration to quantitatively give 1.15 g of sulfate of compound (167) as a colorless solid.

$^1$H-NMR (DMSO-d$_6$) $\delta_{TMS}$: 9.36(bs,2H), 8.96(bs,2H), 8.63(d,J=8.1 Hz,1H), 8.28(d,J=1.7 Hz,1H), 7.92(d,J=8.8 Hz, 1H), 7.84(dd,J=8.8,1.7 Hz, 1H), 7.71(s, 1H), 3.90–3.65(m, 1H), 2.24(t,J=7.5 Hz,2H), 2.00–1.65(m,4H), 1.60–0.90(m, 7H)

EXAMPLE 37

Isopropyl trans-3-[4-[(5-amidino-2-benzofuranyl)carbonylamino]cyclohexyl]propionate (compound (160))

Isopropanol (10 ml) was added to hydrochloride (100 mg, 0.254 mmol) of compound (167) and a hydrogen chloride gas was blown in for 5 minutes, which was followed by stirring at room temperature for hours. Low boiling matters were distilled away from the reaction mixture under reduced pressure and the residue was purified by silica gel column chromatography (chloroform/methanol=97/3) to give 101 mg of hydrochloride of compound (160) as a colorless solid (91%).

IR(KBr): 3700–2700, 1720, 1630, 1520 cm$^{-1}$ $^1$H-NMR (DMSO-d$_6$, 500 MHz) $\delta_{TMS}$: 9.46(bs,2H), 9.21 (bs,2H), 8.66(d,J=8.2 Hz, 1H), 8.30(d,J=1.3 Hz, 1H), 7.92–7.85(m,2H), 7.74(s,1H), 4.92–4.85(m1H), 3.77–3.72 (m1H), 2.27(t,J=7.7 Hz,2H), 1.86–1.73(m,4H), 1.48–1.36 (m,4H), 1.19–1.17(m,7H), 1.17–0.97(m,2H)

EXAMPLE 38

Cyclohexyl trans-3-[4-[(5-amidino-2-benzofuranyl) carbonylamino]cyclohexyl]propionate (compound (162))

In the same manner as in Example 37, cyclohexanol was reacted with hydrochloride (100 mg, 0.254 mmol) of compound (167) to give 109 mg of hydrochloride of compound (162) as a colorless solid (90%).

IR(KBr) :1720, 1635, 1520 cm$^{-1}$ $^1$H-NMR (DMSO-d$_6$, 500 MHz) $\delta_{TMS}$: 9.70–9.00(bs,4H), 8.66(d,J=8.2 Hz,1H), 8.30(d,J=1.8 Hz, 1H), 7.90(d,J=8.8 Hz,1H), 7.87(dd,J=8.8,1.8 Hz, 1H), 7.73(s,1H), 4.68–4.62 (m,1H), 3.78–3.71(m1H), 2.29(t,J=7.6 Hz,2H), 1.88–1.81 (m,2H), 1.81–1.70(m,4H), 1.70–1.60(m,2H), 1.53–1.45(m, 4H), 1.45–1.30(m,5H), 1.30–1.10(m,2H), 1.05–0.95(m, 2H)

EXAMPLE 39

2-Hydroxyethyl trans-3-[4-[(5-amidino-2-benzofuranyl) carbonylamino]cyclohexyl]propionate (compound (163))

Ethylene glycol (3 ml) and methanesulfonic acid (75 mg, 0.780 mmol) were added to hydrochloride (250 mg, 0.635 mmol) of compound (167) and the mixture was stirred at 100° C. for 30 minutes. Ethylene glycol was distilled away from the reaction mixture (0.5 mmHg/60° C.) and the residue was washed with diethyl ether to give 309 mg of methanesulfonate of compound (163) as a colorless solid (95%).

Melting point: 206°–209° C.

IR(KBr): 3700–3150, 3100, 2900, 2850, 1710, 1680, 1638, 1595, 1527 cm$^{-1}$ $^1$H-NMR (DMSO-d$_6$) $\delta_{TMS}$: 9.37(bs,2H), 9.06(bs,2H), 8.64(d,J=7.9 Hz,1H), 8.29(s,1H), 7.92(d,J=8.9 Hz, 1H), 7.85(dd,J=8.8,1.7 Hz,1H), 7.72(s,1H), 4.03(t,J=5.1 Hz,2H), 3.90–3.65(m,1H), 3.56(t,J=5.1 Hz,2H), 2.34(s,3H), 2.34(t, J=7.7 Hz,2H), 1.95–1.70(m,4H), 1.60–0.88(m,7H)

EXAMPLE 40

2-Hydroxyethyl trans-[4-[(5-amidino-2-benzofuranyl) carbonylamino]cyclohexyloxy]acetate (compound (164))

In the same manner as in Example 39, ethylene glycol was reacted with trifluoroacetate (50 mg, 0.106 mmol) of compound (179) to give 42 mg of methanesulfonate of compound (164) as a colorless solid (78%).

Melting point: 212°–215° C.

IR(KBr): 3700–2500, 1740, 1690, 1638, 1595, 1535, 1505 cm$^{-1}$ $^1$H-NMR (DMSO-d$_6$)$\delta_{TMS}$: 9.35(bs,2H), 9.01(bs,2H), 8.64(d,J=8.1 Hz,1H), 8.28(d,J=1.2 Hz,1H), 7.92(d,J=8.8 Hz, 1H), 7.84(dd,J=8.8,1.7 Hz,1H), 7.72(s,1H), 4.15(s,2H), 4.10 (t,J=5.1 Hz,2H), 3.95–3.65(m, 1H), 3.58(t,J=5.0 Hz,2H), 3.40–3.25(m, 1H), 2.35(s, 3H), 2.15–1.80(m,4H), 1.60–1.15 (m, 4H)

EXAMPLE 41 n-Butyl trans-[4-[(5-amidino-2-benzofuranyl) carbonylamino]cyclohexyl]acetate (compound (175))

In the same manner as in Example 39, n-butanol was reacted with trifluoroacetate (200 mg, 0.422 mmol) of compound (179) to give 190 mg of methanesulfonate of compound (175) as a colorless solid (88%).

¹H-NMR (DMSO-d₆) δ$_{TMS}$: 9.35(bs,2H), 8.98(bs,2H), 8.70–8.55(bd,1H), 8.28(d,J=1.2 Hz,1H), 7.97–7.75(m,2H), 7.72(s,1H), 4.14(s,2H), 4.10(q,J=6.5 Hz,2H), 3.92–3.70(m, 1H), 3.45–3.20(m,1H), 2.34(s,3H), 2.12–1.78(m,4H), 1.68–1.15(m,8H), 0.90(t,J=7.2 Hz,3H)

EXAMPLE 42

Ethyl trans-[4-[(5-amidino-2-benzofuranyl)carbonylamino]-cyclohexyloxy]acetate (compound (174))

Ethanol (8 ml) and methanesulfonic acid (360 mg, 3.74 mmol) were added to hydrochloride (300 mg, 0.758 mmol) of compound (179) and the mixture was refluxed under heating for one hour. The reaction mixture was concentrated to about 1/4 under reduced pressure and diethyl ether (8 ml) was added. The precipitated sediment was washed with diethyl ether to give 350 mg of methanesulfonate of compound (174) as a colorless solid (95%).

Melting point: 242°–245° C.

IR(KBr): 3600–2700, 1745, 1673, 1635, 1590, 1520 cm⁻¹

¹H-NMR (DMSO-d₆) δ$_{TMS}$: 9.36(bs,2H), 9.06(bs,2H), 8.65(d,J=8.0 Hz, 1H), 8.29(d,J=1.0 Hz, 1H), 7.95–7.80(m, 2H), 7.72(s,1H), 4.13(s,2H), 4.12(q,J=7.1 Hz, 2H), 3.93–3.68(m1H), 3.50–3.20(m,1H), 2.38(s,3H), 2.15–1.78 (m,4H), 1.21(t,J=7.1 Hz,3H), 1.60–1.15(m,4H)

EXAMPLE 43 t-Butyl trans-[4-[(5-amidino-3-methyl-2-benzofuranyl)carbonylamino]cyclohexyloxy]acetate (compound (181))

In the same manner as in Example 1 (2), 5-cyano-3-methyl-2-benzofurancarboxylic acid (312 mg, 1.55 mmol) and t-butyl trans-(4-aminocyclohexyloxy)acetate (380 mg, 1.66 mmol) were condensed to give 534 mg of t-butyl trans-[4-[(5-cyano-3-methyl-2-benzofuranyl)carbonylamino]cyclohexyloxy]acetate as a colorless solid (84%).

IR(KBr): 3250, 2900, 2200, 1750, 1630, 1120 cm⁻¹

¹H-NMR (CDCl₃) δ$_{TMS}$: 7.96(d,J=1.5 Hz, 1H), 7.68(dd, J=8.6,1.5 Hz, 1H), 7.53(d,J=8.6 Hz, 1H), 6.42(d,J=7.9 Hz, 1H), 4.01(s,2H), 4.07–3.92(m1H), 3.45–3.34(m1H), 2.63(s, 3H), 2.17–2.12(m,4H), 1.49(s,9H), 1.55–1.26(m,4H)

In the same manner as in Example 1 (3), the cyano group of t-butyl trans-[4-[(5-cyano-3-methyl-2-benzofuranyl) carbonylamino]cyclohexyloxy]acetate (530 mg, 1.28 mmol) was converted to an amidino group to give 459 mg of hydriodide of compound (181) as a pale-brown solid (64%).

IR(KBr): 3250, 2900, 1720, 1640, 1600, 1110 cm⁻¹

¹H-NMR (DMSO-d₆, 500 MHz) δ$_{TMS}$: 9.33(bs,4H), 8.45 (d,J=8.1 Hz,1H), 8.29(d,J=1.9 Hz, 1H), 7.88(dd,J=8.7,1.9 Hz, 1H), 7.83(d,J=8.7 Hz,1H), 4.00(S,2H), 3.80–3.78(m, 1H), 2.58(s,3H), 2.62–2.54(m, 1H), 2.04–2.02(m,2H), 1.85–1.82(m,2H), 1.43(s,9H), 1.56–1.39(m,2H), 1.31–1.25 (m,2H)

EXAMPLE 44 trans-[4-[(5-Amidino-3-methyl-2-benzofuranyl)carbonylamino]cyclohexyloxy]acetic acid (compound (182))

In the same manner as in Example 2, hydriodide (435 mg, 0.780 mmol) of compound (181) was treated with trifluoroacetic acid (7 ml) to give 356 mg of hydriodide of compound (182) as a yellow solid (91%).

¹H-NMR (DMSO-d₆, 500 MHz) 12.52(bs,1H), 9.36(s, 2H), 9.17(s,2H), 8.46(d,J=8.1 Hz, 1H), 8.29(d,J=1.9 Hz, 1H), 7.87(dd,J=8.7,1.9 Hz,1H), 7.83(d,J=8.7 Hz,1H), 4.04 (s,2H), 3.80–3.77(m1H), 3.34–3.29(m1H), 2.57(s,3H), 2.05–2.03(m,2H), 1.85–1.83(m,2H), 1.49–1.41 (m,2H), 1.30–1.25(m,2H)

EXAMPLE 45

(1) 5-Cyano-3-methoxy-2-benzofurancarboxylic acid

Methyl 5-bromo-2-hydroxybenzoate (25.6 g, 129 mmol), copper(I) cyanide (20.8 g, 257 mmol) and copper sulfate (200 mg) were added to N-methyl-2-pyrrolidone (250 ml) and the mixture was refluxed under heating for 2 hours under a nitrogen atmosphere. The reaction mixture was cooled to room temperature and poured into a mixture of water (500 ml) and ethylenediamine (10 ml). After filtration, the filtrate was extracted with ethyl acetate. The extract was washed with water and saturated brine, and dried over anhydrous magnesium sulfate. After filtration, low boiling matters were distilled away from the filtrate under reduced pressure and the residue was purified by silica gel column chromatography (ethyl acetate/n-hexane=5/1) to give 3.35 g of methyl 5-cyano-2-hydroxybenzoate as a colorless solid (15%). This solid (3.35 g, 18.9 mmol) and potassium carbonate (5.23 g, 37.0 mmol) were added to N,N-dimethylformamide (45 ml), and ethyl bromoacetate (2.21 ml, 19.9 mmol) was gradually added, which was followed by stirring at room temperature for 18 hours. Water was added to the reaction mixture and the mixture was extracted with an equivalent mixture of ethyl acetate and n-hexane. The extract was washed with water and saturated brine, and dried over anhydrous magnesium sulfate. After filtration, low boiling matters were distilled away from the filtrate under reduced pressure to give a crude product of ethyl 4-cyano-2-methoxycarbonylphenoxyacetate. This product (3.39 g, 19.3 mmol) was dissolved in ethanol (20 ml) and the obtained solution was gradually added to a solution of metallic sodium (622 mg, 27.1 mmol) dissolved in ethanol (50 ml). The mixture was stirred at room temperature for 45 minutes. Low boiling matters were distilled away from the reaction mixture under reduced pressure and water (200 ml) was added to the residue. Dilute hydrochloric acid was added to adjust the pH to 2–3. The resulting precipitate was collected by filtration to quantitatively give 2.98 g of ethyl 5-cyano-3-hydroxy-2-benzofurancarboxylate as a colorless solid.

IR(KBr): 2200, 1680, 1620, 1590 cm⁻¹ ¹H-NMR (DMSO-d₆, 500 MHz) δ$_{TMS}$: 8.38(s,1H), 7.91(d,J=8.7 Hz, 1H), 7.80(d,J=8.7 Hz, 1H), 4.33(q,J=7.1 Hz,2H), 1.32(t,J= 7.1 Hz,3H)

Ethyl 5-cyano-3-hydroxy-2-benzofurancarboxylate (200 mg, 0.866 mmol), dimethyl sulfate (131 mg, 1.04 mmol) and potassium carbonate (132 mg, 0.953 mmol) were added to acetone (140 ml), and the mixture was refluxed under heating for 1.5 hours. Low boiling matters were distilled away from the reaction mixture under reduced pressure and water (200 ml) was added to the residue, which was followed by extraction with ethyl acetate. The extract was washed with water and saturated brine, and dried over anhydrous magnesium sulfate. After filtration, low boiling matters were distilled away from the filtrate under reduced pressure to give 193 mg of ethyl 5-cyano-3-methoxy-2-benzofurancarboxylate (91%). The obtained compound (170 mg, 0.694 mmol) was dissolved in methanol (5 ml) and potassium hydroxide (160 mg, 2.86 mmol) was added, which was followed by refluxing under heating for 45 minutes. Low boiling matters were distilled away from the reaction mixture under reduced pressure and 1N hydrochloric acid was added to the residue to adjust the pH to 2–3. The resulting precipitate was collected by filtration to give 123 mg of 5-cyano-3-methoxy-2-benzofurancarboxylic acid as a colorless solid (82%).

IR(KBr): 2300, 1690, 1585, 1490 cm$^{-1}$ $^1$H-NMR (DMSO-d$_6$, 500 MHz) $\delta_{TMS}$: 8.56(s, 1H), 7.94(dd,J=8.8,1.7 Hz, 1H), 7.85(d,J=8.8 Hz, 1H), 4.22(s,3H) (2) t-Butyl trans-[4-[(5-amidino-3-methoxy-2-benzofuranyl)carbonylamino]cyclohexyloxy]acetate (compound (183))

In the same manner as in Example 1 (2), 5-cyano-3-methoxybenzofuran-2-carboxylic acid (220 mg, 1.01 mmol) and t-butyl 3-(4-amino-cyclohexyl)propionate (244 mg, 1.06 mmol) were condensed to give 316 mg of t-butyl trans-[4-[(5-cyano-3-methoxy-2-benzofuranyl)carbonylamino]cyclohexyloxy]acetate as a colorless solid (73%).

IR(KBr): 2200, 1740, 1640, 1540 cm$^{-1}$ $^1$H-NMR (DMSO-d$_6$, 500 MHz) $\delta_{TMS}$: 8.48(d,J=1.3 Hz,1H), 7.90(dd, J=8.6, 1.3 Hz, 1H), 7.80(d,J=8.6 Hz, 1H), 4.20(s,3H), 3.35–3.25(m,1H), 3.82–3.73(m,1H), 2.05–1.95(m,2H), 1.90–1.80(m,2H), 1.43(s,9H), 1.50–1.10(m,4H)

In the same manner as in Example 1 (3), the cyano group of t-butyl trans-[4-[(5-cyano-3-methoxy-2-benzofuranyl) carbonylamino]-cyclohexyloxy]acetate (310 mg, 0.724 mmol) was converted to an amidino group and purified by silica gel (Chromatorex, NH type, Fuji Silysia Chemical) column chromatography (chloroform/methanol=30/1-1/1) to give 185 mg of compound (183) as a colorless solid (57%).

IR(KBr): 1740, 1640, 1520 cm$^{-1}$ $^1$H-NMR (CDCl$_3$) $\delta_{TMS}$: 8.05(s,1H), 7.67(dd,J=8.7,1.5 Hz, 1H), 7.51(d,J=8.7 Hz, 1H), 7.79–7.60(m,1H), 4.29(s, 3H), 4.10–4.00(m1H), 4.01(s,2H), 3.45–3.35(m,1H), 2.20–2.00(m,1H), 1.49(s,9H), 1.70–1.30(m,1H)

EXAMPLE 46 trans-[4-[(5-Amidino-3-methoxy-2-benzofuranyl)carbonylamino]cyclohexyloxy]acetic acid (compound (184))

In the same manner as in Example 2, compound (183) (180 mg, 0.404 mmol) was treated with trifluoroacetic acid (2 ml) to give 179 mg of trifluoroacetate of compound (184) as a colorless solid (86%).

Melting point: 130°–131° C.

IR(KBr): 1720, 1640, 1530 cm$^{-1}$ $^1$H-NMR (DMSO-d$_6$, 500 MHz) $\delta_{TMS}$: 12.50(bs,1H), 9.38(bs,2H), 9.15(bs,2H), 8.35(d,J=1.8 Hz,1H), 7.98(d,J= 8.0 Hz,1H), 7.88(dd,J=8.8 Hz,1H), 7.84(d,J=8.8 Hz,1H), 4.27(s,3H), 4.03(s,2H), 3.85–3.70(m,1H), 3.40–3.30(m,1H), 2.10–2.00(m,2H), 1.90–1.80(m,2H), 1.50–1.43(m,2H), 1.43–1.20(m,2H)

EXAMPLE 47 t-Butyl trans-[4-[(5-benzylamidino-2-benzofuranyl) carbonylamino]cyclohexyloxy]acetate (compound (171))

The same method as in Example 18 was employed. That is, 5-cyano-2-benzofurancarboxylic acid (749 mg, 4.00 mmol) and t-butyl trans-(4-aminocyclohexyloxy)acetate (917 mg, 4.00 mmol) were condensed to give 1.24 g of t-butyl trans-[4-[(5-cyano-2-benzofuranyl)carbonylamino] cyclohexyloxy]acetate as a colorless solid (78%).

IR(KBr): 3600–3100, 2900, 2200, 1740, 1640, 1562, 1524 cm$^{-1}$ $^1$H-NMR (CDCl$_3$) $\delta_{TMS}$: 8.04(d,J=1.4 Hz,1H), 7.69(dd, J=8.6,1.6 Hz, 1H), 7.60(d,J=8.5 Hz,1H), 7.51(s,1H), 6.43(d, J=7.9 Hz,1H), 4.02(s,2H), 4.10–3.85(m1H), 3.50–3.30(m, 1H), 2.28–2.15(m,4H), 1.49(s,9H), 1.78–1.20(m,4H)

Then, the cyano group of t-butyl trans-[4-[(5-cyano-2-benzofuranyl)carbonylamino]cyclohexyloxy]acetate (1.2 4 g, 3.11 mmol) was converted to a benzylamidino group and the compound was purified by silica gel column chromatography (chloroform/methanol=50/1-5/1), whereafter by silica gel (Chromatorex, NH type, Fuji Silysia Chemical) column chromatography (chloroform/methanol=100/1-20/1) to give 701 mg of compound (171) as a colorless solid (78%).

IR(KBr): 3700–3000, 2920, 1740, 1640, 1590, 1525 cm$^{-1}$ $^1$H-NMR (DMSO-d$_6$) $\delta_{TMS}$: 8.49(d,1H), 8.31(s,1H), 7.97(d, J=8.8 Hz, 1H), 7.64(d,J=8.8HZ, 1H), 7.57(s,1H), 7.50–7.15 (m,8H), 6.80–6.40(m,2H), 4.38(s,2H), 4.00(s,2H), 3.90–3.68(m,1H), 3.50–3.30(m,1H), 2.12–1.78(m,4H), 1.43 (s,9H), 1.60–1.10(m,4H)

EXAMPLE 48 trans-[4-[(5-Benzylamidino-2-benzofuranyl) carbonylamino]-cyclohexyloxy]acetic acid (compound (173))

In the same manner as in Example 2, compound (171) (420 mg, 0.83 mmol) was treated with trifluoroacetic acid (3 ml) to give 395 mg of trifluoroacetate of compound (173) as a colorless solid (84%).

Melting point: 102°–105° C.

IR(KBr): 3600–2700, 1640, 1590, 1520 cm$^{-1}$ $^1$H-NMR (DMSO-d$_6$, 500 MHz) $\delta_{TMS}$: 10.31(t,J=5.2HZ, 1H), 9.64(s,1H), 9.24(s,1H), 8.66(d,J=8.0 Hz, 1H), 8.25(d, J=1.7 Hz, 1H), 7.91(d,J=8.8 Hz, 1H), 7.83(dd,J=8.7,1.8 Hz,1H), 7.71(s,1H), 7.50–7.30(m,5H), 4.70(d,J=5.9 Hz,2H), 4.04(s,2H), 3.85–3.72(m,1H), 3.40–3.20(m,1H), 2.10–1.80 (m,4H), 1.50–1.20(m,4H)

EXAMPLE 49

(1) Ethyl 3-(4-aminopiperidino) propionate 4-Piperidinone (10.0 g, 73.7 mmol) sad potassium carbonate (30.6 g, 221 mmol) were added to N,N-dimethylformamide (100 ml), sad ethyl 3-bromopropionate (10.0 ml, 78.0 mmol) was added. The mixture was stirred at 60° C. for 4.5 hours. The reaction mixture was filtrated sad the filtrate was added with a saturated aqueous sodium hydrogencarbonate solution (150 ml). The mixture was extracted with ethyl acetate. The extract was washed with saturated brine sad dried over anhydrous magnesium sulfate. After filtration, low boiling matters were distilled away from the filtrate under reduced pressure sad the residue was purified by silica gel column chromatography (chloroform/methanol=19/1) to give 9.70 g of ethyl oxopiperidino)propionate as a pale-yellow oil (66%).

Then, ethyl 3-(4-oxopiperidino)propionate (1.29 g, 6.47 mmol) sad benzylamine (0.85 ml, 7.78 mmol) were dissolved in ethanol (40 ml). A solution of sodium cyanoborohydride (256 mg, 4.22 mmol) dissolved in ethanol (20 ml) was added at room temperature sad acetic acid (1 ml) was further added to adjust its pH to 6–7. The mixture was stirred at room temperature for 18 hours sad added with concentrated hydrochloric acid (3 ml) to adjust the pH to 1–2. The resulting precipitate was collected by filtration and a saturated aqueous sodium hydrogencarbonate solution (150 ml) was added to adjust the mixture to pH 8–9. The mixture was extracted with ethyl acetate, and the extract was washed with saturated brine and dried over anhydrous magnesium sulfate. After filtration, low boiling matters were distilled away from the filtrate under reduced pressure to give 1.39 g of ethyl 3-(4-benzylaminopiperidino)propionate as a colorless oil (74%). This oil (1.11 g, 3.82 mmol) was dissolved in ethanol (120 ml) and 10% palladium-carbon (320 mg) was added. The mixture was refluxed under heating for 5 hours under a hydrogen atmosphere. The reaction mixture was filtrated and low boiling matters were distilled away from the filtrate under reduced pressure to give 617 mg of ethyl 3-(4-aminopiperidino)propionate as a colorless oil (81%).

IR (neat): 3300, 2900, 1720, 1600 cm$^{-1}$ $^1$H-NMR (CDCl$_3$) $\delta_{TMS}$: 4.14(q,J=7.1 Hz,2H), 2.87–2.79 (m,2H), 2.72–2.63(m,3H), 2.52–2.44(m,2H), 2.05(td,J=11.6,2.4 Hz,2H), 1.83–1.77(m,2H), 1.45–1.29(m,2H), 1.25 (t,J=7.1 Hz,3H)

(2) Ethyl 3-[4-[[5-(benzyloxycarbonylamidino)-2-benzofuranyl]-carbonylamino]piperidino]propionate (compound (186))

In the same manner as in Example 15 (3), 5-(benzyloxycarbonyl-amidino)-2-benzofurancarboxylic acid (1.08 g, 3.19 mmol) and ethyl 3-(4-aminopiperidino) propionate (610 mg, 3.05 mmol) were condensed to give 1.10 g of compound (186) as a colorless solid (69%).

IR(KBr): 3300, 2930, 1725, 1660, 1635, 1520, 1250 cm$^{-1}$ $^1$H-NMR (CDCl$_3$) $\delta_{TMS}$: 8.24(d,J=1.9 Hz,1H), 7.96(dd, J=8.8,1.9 Hz,1H), 7.55(d,J=8.8 Hz,1H), 7.48–7.30(m,6H), 6.48(d,J=8.3 Hz,1H), 5.23(s,2H), 4.15(q,J=7.2 Hz,2H), 4.03–3.99(m,1H), 2.93–2.87(m,2H), 2.73(t,J=7.0 Hz,2H), 2.51(t,J=7.0 Hz,2H), 2.23(td,J=11.5,2.1 Hz,2H), 2.07–2.02 (m,2H), 1.72–1.53(m,2H), 1.27(t,J=7.2 Hz,3H)

EXAMPLE 50

Ethyl 3-[4-[(5-amidino-2-benzofuranyl)carbonylamino]-piperidino]propionate (compound (191))

The compound (186) (400 mg, 0.768 mmol) was dissolved in ethanol (100 ml) and 10% palladium-carbon (80 mg) was added. The mixture was stirred at room temperature for 4 hours under a hydrogen atmosphere. The reaction mixture was filtrated and low boiling matters were distilled away from the filtrate under reduced pressure. The residue was purified by silica gel (Chromatorex, NH type, Fuji Silysia Chemical) column chromatography (chloroform/methanol=9/1) to give 246 mg of compound (191) as a colorless solid (83%).

IR(KBr): 3240, 2920, 1725, 1635, 1180 cm$^{-1}$ $^1$H-NMR (CDCl$_3$) $\delta_{TMS}$: 7.93(d,J=1.7 Hz, 1H), 7.70(dd, J=8.7,1.7 Hz, 1H), 7.53(d,J=8.7 Hz,1H), 7.47(d,J=0.6 Hz,1H), 6.52(bs,1H), 4.31(bs,3H), 4.15(q,J=7.2 Hz,2H) 4.06–3.94(m,1H), 2.92–2.86(m,2H), 2.73(t,J=6.7 Hz,2H), 2.50(t,J=6.7 Hz, 2H ), 2.28–2.16(ddd, J=12.0,11.4,2.2 Hz, 2H), 2.07–2.02(m,2H), 1.70–1.51(m,2H), 1.27(t,J=7.2 Hz,3H)

EXAMPLE 51

3-[4-[(5-(Amidino-2-benzofuranyl)carbonylamino]piperidino]propionic acid (compound (192))

In the same manner as in Example 10, compound (191) (142 mg, 0.367 mmol) was hydrolyzed to give 150 mg of dihydrochloride of compound (192) as a colorless solid (95%).

Melting point: >250° C.

IR(KBr) :3250, 1715, 1660, 1195 cm$^{-1}$ $^1$H-NMR (DMSO-d$_6$, 500 MHz) $\delta_{TMS}$: 11.10(bs, 1H), 9.47(bs,2H), 9.25(bs,2H), 9.06(d,J=7.5 Hz, 1H), 8.33(s,1H), 7.92(d,J=8.8 Hz, 1H), 7.89(d,J=8.8 Hz, 1H), 7.85(s,1H), 4.10–4.07(m1H), 3.48–3.23(m,4H), 3.13–3.06(m,2H), 2.86 (t,J=7.5 Hz,2H), 2.06–2.01(m,4H)

EXAMPLE 52

3-[4-[[5-(Benzyloxycarbonylamidino)-2-benzofuranyl] carbonylamino]piperidino]propionic acid (compound (189))

In the same manner as in Example 10, compound (186) (150 mg, 0.288 mmol) was hydrolyzed and the residue was purified by column chromatography (chloroform/methanol=1/1) to give 110 mg of hydrochloride of compound (189) as a yellow solid (78%).

IR(KBr) :3600–2500, 1750, 1570, 1520 cm$^{-1}$ $^1$H-NMR (DMSO-d$_6$, 500 MHz) $\delta_{TMS}$: 9.23(bs,2H), 8.84 (d,J=7.7 Hz,1H), 8.45(d,J=1.8 Hz,1H), 8.09(dd,J=8.9,1.8 Hz, 1H), 7.73(d,J=8.9 Hz, 1H), 7.71(s, 1H), 7.45–7.30 (m,5H), 5.12(s,2H), 4.10–3.90(bs,1H), 3.60–3.40(m,2H), 3.10–2.95(m,2H), 2.90–2.70(m,2H), 2.00–1.80(m,4H)

EXAMPLE 53

(1) 5-(Methoxycarbonylamidino)-2-benzofurancarboxylic acid

Methylene chloride (2 ml) was added to ethyl 5-amidino-2-benzofurancarboxylate hydrochloride (100 mg, 0.372 mmol), and methyl chlorocarbonate (30 μl, 0.391 mmol) and then, a 0.2N aqueous sodium hydroxide solution (0.391 ml, 0.782 mmol) was added at room temperature, which was followed by vigorous stirring for 10 minutes. Methylene chloride (15 ml) was added to the reaction mixture. The mixture was washed with water and dried over anhydrous magnesium sulfate. After filtration, low boiling matters were distilled away from the filtrate under reduced pressure to give 88.0 mg of ethyl 5-(methoxycarbonylamidino)-2-benzofurancarboxylic as a colorless solid (82%). Tetrahydrofuran (2 ml), water (2 ml) and a 1N aqueous sodium hydroxide solution (2 ml, 2 mmol) were added to the compound (73.0 mg, 0.252 mmol), and the mixture was stirred at room temperature for one hour. 1N Hydrochloric acid was added to the reaction mixture to adjust its pH to 2–3, and low boiling matters were distilled away under reduced pressure to give 183 mg of 5-(methoxycarbonylamidino)-2-benzofurancarboxylic acid as a yellow solid (inclusive of sodium chloride).

IR (KBr): 1730, 1680, 1550, 1240 cm$^{-1}$ $^1$H-NMR (DMSO-d$_6$, 500 MHz) $\delta_{TMS}$: 10.40(s,1H), 9.59 (bs,1H), 9.46(bs,1H), 8.38–8.35(m,1H), 7.98–7.93(m,2H), 7.89–7.85(m,1H), 3.86(s,3H) (2) Ethyl 3-[4-[[5-(methoxycarbonylamidino)-2-benzofuranyl] carbonylamino]piperidino]propionate (compound (187))

N,N-Dimethylformamide (14 ml) and N-methylmorpholine (0.57 ml, 5.20 mmol) were added to ethyl 3-(4-aminopiperidino)propionate dihydrochloride (567 mg, 2.08 mmol) and the mixture was stirred at 60° C. for 20 minutes under a nitrogen atmosphere. This solution was added to a mixture of 5-(methoxycarbonylamidino)-2-benzofurancarboxylate acid (364 mg, 1.39 mmol), 1-hydroxy-1H-benzotriazole (207 mg, 1.54 mmol) and 1-(3-dimethylaminopropyl)-3-ethylcarbodiimide (294 mg, 1.54 mmol) added to N,N-dimethylformamide (15 ml). The mixture was stirred at room temperature for 18 hours. Water (100 ml) was added to the reaction mixture, and the mixture was extracted with ethyl acetate. The extract was washed with water and saturated brine, and dried over anhydrous magnesium sulfate. After filtration, low boiling matters were distilled away from the filtrate under reduced pressure. The residue was purified by column chromatography (chloroform/methanol=10/1) to give 338 mg of compound (187) as a yellow solid (55%).

IR(KBr): 1700, 1620, 1490 cm$^{-1}$ $^1$H-NMR (DMSO-d$_6$, 500 MHz) $\delta_{TMS}$: 9.15(bs,2H), 8.60 (d,J=8.0 Hz,1H), 8.41 (d,J=1.7 Hz, 1H), 8.06(dd, J=8.5,1.7 Hz,1H), 7.73(d,J=8.5 Hz,1H), 7.65(s,1H), 4.07(q,J=7.1

Hz,2H), 3.82–3.72(m,1H), 2.93–2.75(m,2H), 2.60–2.40(m, 4H), 2.10–1.93(m,2H), 1.80–1.70(m,2H), 1.65–1.50(m,2H), 1.19(t,J=7.1 Hz,3H)

EXAMPLE 54

(1) 5-Benzylamidino-2-benzofurancarboxylic acid

Ethanol (30 ml) was added to 5-cyano-2-benzofurancarboxylic acid (689 mg, 3.68 mmol) and a hydrogen chloride gas was blown in under ice-cooling for 15 minutes and the mixture was stirred at room temperature for 16 hours. Low boiling matters were distilled away from the reaction mixture under reduced pressure and the residue was dissolved in ethanol (25 ml). Benzylamine (1.58 g, 14.7 mmol) was added under ice-cooling and the mixture was stirred for one hour and at room temperature for 2 hours. Low boiling matters were distilled away from the reaction mixture under reduced pressure and the residue was purified by silica gel column chromatography (chloroform/methanol=100/3-4/1) to give 361 mg of ethyl 5-benzylamidino-2-benzofurancarboxylate hydrochloride as a colorless solid (30%).

$^1$H-NMR (DMSO-d$_6$, 500 MHz) $\delta_{TMS}$: 9.75(s,1H), 9.45 (s,1H), 8.37(s,1H), 8.04–7.99(m1H), 7.98–7.90(m,2H), 7.55–7.45(m,5H), 4.75(d,J=5.8 Hz,2H), 4.40(q,J=7.2 Hz,2H), 1.36(t,J=7.2 Hz,3H)

Tetrahydrofuran (5 ml) was added to ethyl 5-benzylamidino-2-benzofurancarboxylate (325 mg, 1.21mmol) and a 0.5N aqueous sodium hydroxide solution (10 ml, 5 mmol) was added. The mixture was stirred at room temperature for 45 minutes. 1N Hydrochloric acid was added to the reaction mixture to adjust its pH to 2–3 and low boiling matters were distilled away under reduced pressure. The resulting precipitate was collected by filtration, and washed with water to give 213 mg of 5-benzylamidino-2-benzofurancarboxylic acid hydrochloride as a colorless solid (53%).

IR(KBr): 1680, 1635, 1580, 1400 cm$^{-1}$ $^1$H-NMR (DMSO-d$_6$, 500 MHz) $\delta_{TMS}$: 10.40(s,1H), 9.69 (s,1H), 9.37(s,1H), 8.28(d,J=1.6 Hz,1H), 7.97(d,J=8.8 Hz,1H), 7.89(dd,J=8.8,1.6 Hz,1H), 7.85(s,1H), 7.50–7.30 (m,5H), 4.73(d,J=5.7 Hz,2H)

(2) Ethyl 3-[4-[(5-benzylamidino-2-benzofuranyl)carbonylamino]piperidino]propionate (compound (188))

In the same manner as in Example 53 (2), 5-benzylamidino-2-benzofurancarboxylic acid (210 mg, 0.635 mmol) and ethyl 3-(4-aminopiperidino)propionate dihydrochloride (173 mg, 0.635 mmol) were condensed to give 160 mg of compound (188) as a yellow solid (53%).

IR(KBr): 1695, 1625, 1580, 1500, 1430 cm$^{-1}$ $^1$H-NMR (DMSO-d$_6$, 500 MHz) $\delta_{TMS}$: 8.54(d,J=8.0 Hz, 1H), 8.20(s,1H), 8.00–7.90(m,1H), 7.64(d,J=8.7 Hz,1H), 7.58(s,1H), 7.43(d,J=7.4 Hz, 1H), 7.33(dd,J=7.4 Hz, 1H), 7.21 (t,J=7.4 Hz, 1H), 4.37(s,2H), 4.06(q,J=7.1 Hz,2H), 3.80–3.70(m,1H), 3.00–2.80(m,2H), 2.60–2.45(m,4H), 2.08–1.97(t,J=8.5 Hz,2H), 1.80–1.70(m,2H), 1.68–1.57(m, 2H), 1.19(t,J=7.1 Hz,3H)

EXAMPLE 55

3-[4-[(5-Benzylamidino)-2-benzofuranyl)carbonylamino] piperidino]propionic acid (compound (190))

In the same manner as in Example 10, compound (188) (140 mg, 0.294 mmol) was hydrolyzed to give 150 mg of dihydrochloride of compound (190) as a yellow solid (98%).

Melting point: 181°–184° C.

IR(KBr): 1710, 1620, 1520 cm$^{-1}$ $^1$H-NMR (DMSO-d$_6$, 500 MHz) $\delta_{TMS}$: 10.46(s,1H), 9.73 (s,1H), 9.42(s,1H), 9.09(d,J=7.5 Hz,1H), 8.31(s,1H), 7.90 (d,J=8.8 Hz,1H), 7.87(d,J=8.7 Hz,1H), 7.83(s,1H), 7.49(d, J=7.4 Hz,2H), 7.43(t,J=7.4 Hz,2H), 7.35(t,J=7.4 Hz,1H), 4.75(d,J=5.8 Hz,2H), 4.14–4.00 (m,1H), 3.55–3.40(m,2H), 3.30–3.18(m,2H), 3.15–3.05(m,2H), 2.89(t,J=8.1 Hz,2H), 2.13–1.95(m,1H)

EXAMPLE 56

(1) Di-t-butyl cis- or trans-(4-aminocyclohexylamino) diacetate 1,4-Diaminocyclohexane (cis, trans mixture) (24.0 g, 210 mmol) and triethylamine (16.3 ml, 117 mmol) were dissolved in methylene chloride (400 ml). A solution of triphenylmethyl chloride (32.5 g, 117 mmol) dissolved in methylene chloride (100 ml) was dropwise added under ice-cooling and the mixture was stirred for 15 minutes and at room temperature for 45 minutes. The reaction mixture was filtrated and low boiling matters were distilled away from the filtrate under reduced pressure. Water (100 ml) was added to the residue and extracted with chloroform. The extract was dried over anhydrous sodium sulfate. After filtration, low boiling matters were distilled away from the filtrate under reduced pressure. The residue was purified by silica gel (Chromatorex, NH type, Fuji Silysia Chemical) column chromatography (chloroform/n-hexane=5/1-10/1) to give 18.4 g of 1-amino-4-(triphenylmethylamino) cyclohexane as a pale-yellow oil (25%).

1-Amino-4-(triphenylmethylamino)cyclohexane (18.4 g, 51.7 mmol) and potassium carbonate (15.0 g, 108.6 mmol) were added to N,N-dimethylformamide (250 ml), and t-butyl bromoacetate (20.7 g, 106.0 mmol) was dropwise added under ice-cooling, which was followed by stirring for 10 minutes and at room temperature for 2.5 hours. Thereafter, triethylamine (14.8 ml, 106 mmol) was added and the mixture was stirred for 1.5 hours. The reaction mixture was filtrated and water (500 ml) was added to the filtrate. The mixture was extracted with ethyl acetate. The extract was washed with water and saturated brine, and dried over anhydrous magnesium sulfate. After filtration, low boiling matters were distilled away from the filtrate under reduced pressure, and the residue was purified by silica gel column chromatography (n-hexane/ethyl acetate=50/1-5/1) to give 3.56 g of di-t-butyl trans-[4-(triphenylmethylamino) cyclohexylamino]diacetate as a colorless solid (12%) and 16.23 g of di-t-butyl cis-[4-(triphenylmethylamino) cyclohexylamino]diacetate as a viscous pale-yellow oil (54%).

Di-t-butyl trans-[4-(triphenylmethylamino) cyclohexylamino]diacetate (3.46 g, 5.92 mmol) was dissolved in methanol (100 ml) and added with 10% palladium-carbon (0.75 g). The mixture was refluxed under heating for 7 hours under a hydrogen atmosphere. The reaction mixture was filtered through Celite and low boiling matters were distilled away from the filtrate under reduced pressure. 1N Hydrochloric acid (30 ml) and water (50 ml) were added to the residue and the mixture was washed with diethyl ether. Sodium hydrogen-carbonate was added to the aqueous layer to make the same alkaline to saturate sodium chloride. The mixture was extracted with chloroform and the extract was dried over anhydrous sodium sulfate. After filtration, low boiling matters were distilled away from the filtrate under reduced pressure to quantitatively give 2.13 g of di-t-butyl trans-(4-aminocyclohexylamino)diacetate as a pale-yellow oil.

In the same manner, 89 mg of di-t-butyl cis-(4-aminocyclohexyl-amino)diacetate was quantitatively obtained as a colorless oil from di-t-butyl cis-[4-(triphenylmethylamino) cyclohexylamino]diacetate (135 mg, 0.165 mmol). trans compound IR (CHCl$_3$): 2910, 1725, 1590, 1480, 1442 cm$^{-1}$ $^1$H-NMR (CDCl$_3$) $\delta_{TMS}$: 3.45(s,4H), 2.78–2.50(m,2H), 2.00–1.80(m,4H), 1.45(s,18H), 1.65–0.95 (m,4H) cis compound IR (neat): 2975, 2925, 2850, 1730, 1670, 1450, 1390, 1365, 1250, 1215, 1150 cm$^{-1}$ $^1$H-NMR (CDCl$_3$) $\delta_{TMS}$: 3.46(s,1H), 2.98–2.68(m,2H), 1.85–1.18(m,8H), 1.45(s,18H) (2) Di-t-butyl trans-[4-[[5-(benzyloxycarbonylamidino)-2-benzofuranyl] carbonylamino]cyclohexylamino]diacetate (compound (201))

In the same manner as in Example 15 (3), 5-(benzyloxycarbonylamidino)-2-benzofurancarboxylic acid (2.04 g, 6.04 mmol) and di-t-butyl trans-(4-aminocyclohexylamino)diacetate (2.07 g, 6.04 mmol) were condensed and purified by silica gel column chromatography (ethyl acetate/n-hexane=1/2-2/1) to give 2.04 g of compound (201) as a colorless solid (51%).

IR(KBr): 3700–3000, 2910, 1722, 1657, 1618, 1587, 1510 cm$^{-1}$ $^1$H-NMR (CDCl$_3$) $\delta_{TMS}$: 8.23(d,J=1.5 Hz,1H), 7.95(dd, J=8.8,1.9 Hz,1H), 7.60–7.25(m,7H), 6.41 (d,J=8.3 Hz,1H), 5.23(s,2H), 4.05–3.80(m,1H), 3.47(s,4H), 2.95–2.60(m,1H), 2.25–1.90(m,4H), 1.46(s,18H), 1.60–1.15(m,4H)

EXAMPLE 57

Di-t-butyl trans-[4-[[5-amidino-2-benzofuranyl)carbonylamino]cyclohexylamino]diacetate (compound (203))

Compound (201) (1.60 g, 2.41 mmol) was dissolved in t-butanol (100 ml) and 10% palladium-carbon (0.56 g) was added, which was followed by refluxing under heating for 14 hours under a hydrogen atmosphere. The reaction mixture was filtered through Celite and low boiling matters were distilled away from the filtrate under reduced pressure. The residue was purified by silica gel (Chromatorex, NH type, Fuji Silysia Chemical) column chromatography (chloroform/methanol=5/1-3/1) to give 1.20 g of compound (203) as a pale-brown solid (94%).

Melting point: 78°–81° C.

IR(KBr): 3700–3000, 2960, 2910, 1725, 1638, 1590, 1570, 1520 cm$^{-1}$ $^1$H-NMR (CDCl$_3$) $\delta_{TMS}$: 7.93(s,1H), 7.69(d,J=8.3 Hz,1H), 7.52(d,J=8.8 Hz,1H), 7. 47(s,1H), 6.44(d,J=6.2 Hz,1H), 4.07–3.85(m,1H), 3.47(s,4H), 2.88–2.65(m,1H), 2.28–1.95(m,1H), 1.46(s,18H), 1.60–1.15(m,4H)

EXAMPLE 58 trans-[4-[(5-Amidino-2-benzofuranyl)carbonylamino] cyclohexylamino]diacetic acid (compound (204))

In the same manner as in Example 2, compound (203) (1.17 g, 2.22 mmol) was treated with trifluoroacetic acid (14 ml) to give 1.11 g of ditrifluoroacetate of compound (204) as a colorless solid (77%).

IR(KBr): 3700–2500, 1658, 1592, 1528, 1450 cm$^{-1}$ $^1$H-NMR (DMSO-d$_6$) $\delta_{TMS}$: 9.37(bs,2H), 9.17(bs,2H), 8.69(d,J=8.1 Hz,1H), 8.28(s,1H), 7.92(d,J=8.7 Hz,1H), 7.85 (dd,J=8.8,1.7 Hz,1H), 7.71 (s,1H), 3.81 (s,4H), 3.10–2.90 (m,1H), 2.10–1.72(m,4H), 1.65–1.30(m,1H)

Acetic acid (10 ml) was added to ditrifluoroacetate (200 mg, 0.310 mmol) of compound (204) and methanesulfonic acid (1.63 g, 16.95 mmol) was added while heating the mixture at 70° C. When the reaction mixture was dissolved to transparency, it was cooled to room temperature and diethyl ether (50 ml) was added. The precipitated sediment was washed with diethyl ether and tetrahydrofuran in order and collected by filtration to quantitatively give 214 mg of dimethanesulfonate of compound (204) as a pale-gray solid.

Melting point: >250° C.

IR(KBr): 3700–2100, 1720, 1680, 1635, 1600, 1585, 1530 cm$^{-1}$ $^1$H-NMR (DMSO-d$_6$, 500 MHZ) $\delta_{TMS}$: 9.36(s,2H), 8.98 (s,2H), 8.74(d,J=8.1 Hz,1H), 8.29(d,J=1.5 Hz,1H), 7.91 (d,J=8.8 Hz,1H), 7.86(dd,J=8.8,1.8 Hz,1H), 7.72(s,1H), 4.18(s,4H), 3.97–3.85(m,1H), 3.48–3.35(m,1H), 2.36(s,6H), 2.10–1.90(m,1H), 1.80–1.45(m,4H)

EXAMPLE 59

Diethyl trans-[4-[(5-amidino-2-benzofuranyl) carbonylamino]cyclohexylamino]diacetate (compound (202))

Ethanol (8 ml) and methanesulfonic acid (654 mg, 6.80 mmol) were added to dimethanesulfonate (131 mg, 0.216 mmol) of compound (204) and the mixture was refluxed under heating for 6 hours. The reaction mixture was cooled to room temperature and added with diethyl ether (40 ml). The precipitated sediment was washed with diethyl ether and tetrahydrofuran in order and collected by filtration to give 75 mg of dimethanesulfonate of compound (202) as a colorless solid (52%).

Melting point: 100°–102° C.

IR(KBr): 3700–2500, 1738, 1640, 1592, 1570, 1525, 1450 cm$^{-1}$ $^1$H-NMR (DMSO-d$_6$) $\delta_{TMS}$: 9.37(bs,2H), 9.10(bs,1H), 8.76(d,J=8.2 Hz,1H), 8.30(s,1H), 8.00–7.80(m,2H), 7.73(s, 1H), 4.26(s,4H), 4.24(q,J=7.1 Hz,4H), 3.55–3.40(m,1H), 2.37(s,6H), 2.12–1.83(m,4H), 1.80–1.35(m,4H), 1.26(t,J= 7.1 Hz,6H)

EXAMPLE 60 cis-[4-[(5-Amidino-2-benzofuranyl)carbonylamino] cyclohexylamino]diacetic acid (compound (205))

In the same manner as in Example 15 (3), 5-(benzyloxycarbonylamidino)-2-benzofurancarboxylic acid (27.8mg, 0.0822 mmol) and di-t-butyl cis-(4-aminocyclohexylamino) diacetate (27.6 mg, 0.0806 mmol) were condensed to give 34.0 mg of di-t-butyl cis-[4-[[5-(benzyloxycarbonylamidino)-2-benzofuranyl] carbonylamino]cyclohexylamino]diacetate as a colorless oil (64%). This oil (34.0 mg, 0.0513 mmol) was subjected to hydrogen reduction in the same manner as in Example 57 to quantitatively give 28.4 mg of di-t-butyl cis-[4-[(5-amidino-2-benzofuranyl)carbonylamino]cyclohexylamino]diacetate as a pale-brown oil. Methylene chloride (0.8 ml) and trifluoroacetic acid (0.8 ml) were added to this oil (28.4 mg, 0.0513 mmol) and the mixture was stirred at room temperature for 3 hours. Low boiling matters were distilled away from the reaction mixture under reduced pressure and the residue was dissolved in water (4 ml). The solution was lyophilized to give 29.3 mg of ditrifluoroacetate of compound (205) as a colorless solid (89%).

IR(KBr): 3350, 1665, 1520, 1450, 1320, 1265, 1195, 1130 cm$^{-1}$ $^1$-H-NMR (DMSO–d$_6$, 500 MHz) $\delta_{TMS}$; 9.37(s,2H), 9.19 (s,2H), 8.55(d,J=7.6 Hz,1H), 8.29(s,1H), 7.94(d,J=8.8

Hz,1H), 7.86(dd,J=8.8,1.8 Hz,1H), 7.78(s,1H), 4.09(s,1H), 3.84(s,4H), 3.13(s,1H), 1.86(m,2H), 1.76(m,2H), 70(bs,2H), 1.61(m,2H)

EXAMPLE 61

(1) t-Butyl trans-[4-aminocyclohexyl-N-(t-butoxycarbonyl)amino]acetate trans-4-(Triphenylmethylamino)cyclohexylamine (2.73 g, 7.66 mmol) and potassium carbonate (2.22 g, 16.08 mmol) were added to N,N-dimethylformamide (100 ml) and t-butyl bromoacetate (1.57 g, 8.04 mmol) was dropwise added under ice-cooling. The mixture was stirred for 30 minutes and at room temperature for 30 minutes. The reaction mixture was filtrated and water (200 ml) was added to the filtrate. The mixture was extracted with ethyl acetate. The extract was washed with water and saturated brine, and dried over anhydrous magnesium sulfate. After filtration, low boiling matters were distilled away from the filtrate under reduced pressure, and the residue was purified by silica gel column chromatography (n-hexane/ethyl acetate= 20/1-1/1) to give 2.98 g of t-butyl trans-[4-(triphenylmethylamino)cyclohexylamino]acetate as a colorless solid (83%). This solid (2.40 g, 5.10 mmol), 4-dimethylaminopyridine (0.31 g, 2.55 mmol) and pyridine (0.81 g, 10.20 mmol) were dissolved in methylene chloride (40 ml) and a solution of di-t-butyl dicarbonate (1.17 g, 5.35 mmol) dissolved in methylene chloride (10 ml) was dropwise added under ice-cooling, which was followed by stirring for 2 hours. Water (100 ml) and 1N hydrochloric acid (20 ml) were added and the mixture was extracted with chloroform. The extract was dried over anhydrous magnesium sulfate. After filtration, low boiling matters were distilled away from the filtrate under reduced pressure, and the residue was purified by silica gel column chromatography (n-hexane/ethyl acetate=10/1-5/1) to give 1.82 g of t-butyl trans-[4-(triphenylmethylamino)cyclohexyl-N-(t-butoxycarbonyl)amino]acetate as a colorless solid (63%). This solid (1.82 g, 3.19 mmol) was dissolved in ethanol (60 ml) and 10% palladium-carbon (0.40 g) was added. The mixture was refluxed under heating for 16 hours under a hydrogen atmosphere. The reaction mixture was filtered through Celite and low boiling matters were distilled away from the filtrate under reduced pressure. Water (20 ml) and 1N hydrochloric acid (10 ml) were added to the residue and the mixture was extracted with diethyl ether. A saturated aqueous sodium hydrogencarbonate solution was added to the aqueous layer to make the same alkaline, and the mixture was extracted with chloroform. The extract was dried over anhydrous magnesium sulfate. After filtration, low boiling matters were distilled away from the filtrate under reduced pressure to give 0.67 g of t-butyl trans-[4-aminocyclohexyl-N-(t-butoxycarbonyl)amino]acetate as a pale-yellow solid (64%).

IR(KBr): 3400, 2900, 1738, 1690, 1435 cm$^{-1}$ $^1$H-NMR (CDCl$_3$) $\delta_{TMS}$: 4.15–3.90(m1H), 3.65(s,2H), 2.70–2.45(m,1H), 2.00–1.70(m,4H), 1.46(s,9H), 1.44(s,9H), 1.55–0.80(m,4H)

(2) t-Butyl trans-[4-[(5-amidino-2-benzofuranyl)carbonylamino]-cyclohexyl-N-(t-butoxycarbonyl)amino]acetate (compound (194))

In the same manner as in Example 15 (3), 5-(benzyloxycarbonylamidino)-2-benzofurancarboxylic acid (690 mg, 2.04 mmol) and t-butyl trans -[4-aminocyclohexyl-N-(t-butoxycarbonyl)amino]acetate (670 mg, 2.04 mmol) were condensed and purified by silica gel column chromatography (n-hexane/ethyl acetate=2/3) to give 493 mg of t-butyl trans-[4-[[5-(benzyloxycarbonylamidino)-2-benzofuranyl]carbonylamino]cyclohexyl-N-(t-butoxycarbonyl)amino]acetate as a colorless solid (37%).

IR(KBr): 3600–3100, 2910, 1740, 1650, 1620, 1585, 1510, 1438 cm$^{-1}$ $^1$H-NMR (CDCl$_3$) $\delta_{TMS}$: 10.2–9.70(br,2H), 8.21 (d,J=1.6 Hz,1H), 7.95(dd,J=8.8,1.6 Hz,1H), 7.55–7.25(m,7H), 6.54 (d,J-8.3 Hz,1H), 5.22(s,2H), 4.25–4.02(m1H), 4.02–3.75(m, 1H), 3.68(s,2H), 2.25–1.75(m,4H), 1.48(s,9H), 1.45(s,9H), 1.60–0.80(m,4H)

t-Butyl trans-[4-[[5-(benzyloxycarbonylamidino)-2-benzofuranyl]carbonylamino]cyclohexyl-N-(t-butoxycarbonyl)amino]acetate (482 mg, 0.743 mmol) was dissolved in ethanol (20 ml) and 10% palladium-carbon (150 mg) was added, which was followed by refluxing under heating for 16 hours under a hydrogen atmosphere. The reaction mixture was filtered through Celite and low boiling matters were distilled away from the filtrate under reduced pressure. The residue was purified by silica gel (Chromatorex, NH type, Fuji Silysia Chemical) column chromatography (chloroform/methanol=5/1) to give 328 mg of compound (194) as a pale-yellow solid (86%).

IR(KBr): 3600–3000, 2920, 1735, 1635, 1590, 1520, 1432 cm$^{-1}$ $^1$H-NMR (CDCl$_3$) $\delta_{TMS}$: 7.94(s,1H), 7.70(d,J=8.9 Hz,1H), 7.52(m,1H), 7.45(s,1H), 6.75–6.30(m,1H), 5.20–4.30(m,3H), 4.30–4.03(m,1H), 4.03–3.80(m,1H), 3.68 (s,2H), 2.30–1.70(m,4H), 1.48(s,9H), 1.45(s,9H), 1.70–0.80 (m,4H)

EXAMPLE 62 trans-[4-[(5-Amidino-2-benzofuranyl)carbonylamino]cyclohexylamino]acetic acid (compound (195))

Compound (194) (216mg, 0.420 mmol) was dissolved in methylene chloride (8 ml) and trifluoroacetic acid (4 ml) was added. The mixture was stirred at room temperature for 23 hours. The reaction mixture was concentrated to about ⅓ under reduced pressure and diethyl ether (50 ml) was added. The precipitated sediment was washed with diethyl ether and collected by filtration to give 219 mg of ditrifluoroacetate of compound (195) as a colorless solid (89%).

IR(KBr): 3600–2600, 1665, 1530, 1450 cm$^{-1}$ $^1$H-NMR (DMSO-d$_6$, 500 MHz) $\delta_{TMS}$: 9.37(bs,2H), 9.21 (bs,2H), 8.96(bs,2H), 8.74(d,J=8.0 Hz,1H), 8.29(d,J=1.8 Hz,1H), 7.91(d,J=8.8 Hz,1H), 7.86(dd,J=8.8,1.8 Hz,1H), 7.72(s,1H), 3.94(s,2H), 3.83–3.70(m,1H), 3.12–3.00(m,1H), 2.20–2.00(m,2H), 2.00–1.88(m,2H), 1.56–1.37(m,4H)

Acetic acid (10 ml) and methanesulfonic acid (148 mg, 1.54 mmol) were added to ditrifluoroacetate (200 mg, 0.341 mmol) of compound (195) and the reaction mixture was stirred at 50° C. until it was dissolved to transparency. The reaction mixture was cooled to room temperature and added with diethyl ether (50 ml). The precipitated sediment was washed with diethyl ether, collected by filtration, dissolved in water (20 ml) and lyophilized to give 140 mg of dimethanesulfonate of compound (195) as a colorless solid (75%).

$^1$H-NMR (DMSO-d$_6$) $\delta_{TMS}$: 9.36(bs,2H), 9.08(bs,2H), 8.91(bs,2H), 8.75(d,J=8.1 Hz,1H), 8.30(s,1H), 7.92(d,J=8.8 Hz,1H), 7.85(dd,J=8.8,1.7 Hz,1H), 7.73(s,1H), 3.94(bs,2H), 3.90–3.65(m,1H), 3.20–2.95(m,1H), 2.36(s,6H), 2.27–1.80 (m,24H), 1.70–1.30(m,24H)

EXAMPLE 63

Ethyl (S)-3-[4-[(5-amidino-2-benzofuranyl)carbonylamino]phenyl]-2-(n-butylsulfonylamino)propionate (compound (41))

In the same manner as in Example 15 (3), 5-(benzyloxycarbonyl)-2-benzofurancarboxylic acid (462 mg, 1.36 mmol) and ethyl (S)-3-(4-aminophenyl)-2-(n-butylsulfonylamino) propionate (448 mg, 1.35 mmol) were condensed to quantitatively give 886 mg of ethyl (benzyloxycarbonylamidino)-2-benzofuranyl]carbonylamino]phenyl[-2-(n-butylsulfonylamino) propionate as a colorless solid. Ethanol (20 ml), chloroform (100 ml), 10% palladium-carbon (260 mg) and 1N hydrochloric acid (2 ml) were added to this solid (830 mg, 1.28 mmol) and the mixture was stirred at room temperature for 30 hours under a hydrogen atmosphere. The reaction mixture was filtrated and low boiling matters were distilled away from the filtrate under reduced pressure. The residue was purified by silica gel column chromatography (chloroform/methanol=9/1-1/1) to give 524 mg of hydrochloride of compound (41) as a colorless solid $^1$H-NMR (DMSO-d$_6$) $\delta_{TMS}$: 10.72(bs,1H), 9.33(bs,4H), 8.38(d,J=1.5 Hz,1H), 8.03(s,1H), 7.97(d,J=10.0 Hz,1H), 7.93(dd,J=10,1.5 Hz,1H), 7.78(d,J=8.4 Hz,2H), 7.29(d,J=8.4 Hz,2H), 4.16–4.05(m,3H), 2.97 (dd,J=13.6,5.9 Hz,1H), 2.85(dd,J=13.6,9.3 Hz,1H), 2.68(t,J=6.8 Hz,2H), 1.41–1.13 (m,7H), 0.76 (t,J=7.0 Hz,3H)

EXAMPLE 64

(1) Ethyl (S)-3-(4-aminophenyl)-2-(benzyloxycarbonylamino)propionate

Hydrochloride (1.00 g, 3.64 mmol) of ethyl (S)-2-amino-3-(4-nitrophenyl)propionate was dissolved in a mixed solution of tetrahydrofuran (10 ml), water (10 ml) and a 1N aqueous sodium hydroxide solution (3.64 ml) and a solution of benzyloxycarbonyl chloride (0.57 ml, 3.99 mmol) dissolved in tetrahydrofuran (3.5 ml) and a 1N aqueous sodium hydroxide solution (3.64 ml, 3.64 mmol) were simultaneously added dropwise under ice-cooling, which was followed by stirring at room temperature for 4 hours. A saturated aqueous sodium hydrogen carbonate solution (30 ml) was added, and the mixture was extracted with ethyl acetate. The extract was washed with saturated brine, and dried over anhydrous magnesium sulfate. After filtration, low boiling matters were distilled away from the filtrate under reduced pressure and the residue was purified by silica gel column chromatography (n-hexane/ethyl acetate=1/1) to give 743 mg of ethyl (S)-2-(benzyloxycarbonylamino)-3-(4-nitrophenyl)propionate as a colorless solid (55%). This solid (724 mg, 1.94 mmol) was dissolved in a mixture of ethanol (120 ml) and water (30 ml), and zinc (6.40 g, 97.9 mmol) and calcium chloride (2.00 g, 18.0 mmol) were added. The mixture was refluxed under heating for 3.5 hours. The reaction mixture was cooled to room temperature and filtrated. The filtrate was concentrated and water (100 ml) was added to the filtrate. The mixture was extracted with ethyl acetate, and the extract was washed with saturated brine and dried over anhydrous magnesium sulfate. After filtration, low boiling matters were distilled away from the filtrate under reduced pressure to give 572 mg of ethyl (S)-3-(4-aminophenyl)-2-(benzyloxycarbonylamino)propionate as a pale-yellow oil (86%).

IR (neat) :3320, 1710, 1620, 1510 cm$^{-1}$ $^1$H-NMR (CDCl$_3$) $\delta_{TMS}$: 7.34–7.29(m,5H), 6.88(d,J=8.4 Hz,2H), 6.58(d,J=8.4 Hz,2H), 5.21(d,J=8.0 Hz,1H), 5.09(s, 2H), 4.62–4.52(m,1H), 4.16(q,J=7.1 Hz,2H), 2.99(d,J=5.7 Hz,2H), 1.24(t,J=7.1 Hz,3H)

(2) Ethyl (S)-3-[4-[(5-amidino-2-benzofuranyl)carbonylamino]phenyl]-2-(benzyloxycarbonylamino) propionate (compound (42))

Hydrochloride (387 mg, 1.61 mmol) of 5-amidino-2-benzofurancarboxylic acid and ethyl (S)-3-(4-aminophenyl)-2-(benzyloxycarbonylamino)propionate (550 mg, 1.61 mmol) were added to N,N-dimethylformamide (20 ml), and diisopropylcarbodiimide (0.30 ml, 1.94 mmol) and 1-hydroxy-1H-benzotriazole (260 mg, 1.92 mmol) were added. The mixture was stirred at room temperature for 12 hours and at 60° C. for 4 hours. N,N-Dimethylformamide was distilled away from the reaction mixture under reduced pressure. The residue was purified by silica gel (Chromatorex, NH type, Fuji Silysia Chemical) column chromatography (chloroform/methanol=9/1). A solution (10 ml) of hydrochloric acid dissolved in ethanol was added to convert the purified residue to hydrochloride. Low boiling matters were distilled away from this solution under reduced pressure and the residue was purified by silica gel column chromatography (chloroform/methanol=5/2) to give 343 mg of hydrochloride of compound (42) as a pale-yellow solid (38%).

IR(KBr): 3200, 1710, 1660, 1600, 1520 cm$^{-1}$ $^1$H-NMR (DMSO-d$_6$) $\delta_{TMS}$: 10.72(bs,1H), 9.40(bs,4H), 8.39(s,1H), 8.06–7.78(m,4H), 7.75(d,J=8.3 Hz,2H), 7.35–7.24(m,7H), 5.00(s,2H), 4.31–4.19(m,1H), 4.09(q,J=7.1 Hz,2H), 3.09–2.81 (m,2H), 1.14(t,J=7.1 Hz,3H)

EXAMPLE 65

Ethyl (S)-3-[4-[(5-amidino-2-benzofuranyl)carbonylamino]phenyl]-2-aminopropionate (compound (45))

Hydrochloride (335 mg, 0.593 mmol) of compound (42) was dissolved in an equivalent mixture (40 ml) of ethanol and methanol and 10% palladium-carbon (100 mg) was added. The mixture was stirred at room temperature for 15 hours under a hydrogen atmosphere. The reaction mixture was filtrated and low boiling matters were distilled away from the filtrate under reduced pressure to give 239 mg of monohydrochloride of compound (45) as a pale-green solid (94%).

IR(KBr): 3150, 1720, 1660, 1600, 1520 cm$^{-1}$ $^1$H-NMR (DMSO-d$_6$) $\delta_{TMS}$: 10.70(bs,1H), 9.33(bs,4H), 8.38(d,J=1.7 Hz, 1H), 8.03(s,1H), 7.98(d,J=9.0 Hz,1H), 7.92(dd,J=9.0,1.7 Hz,1H), 7.73(d,J=8.5 Hz,2H), 7.19(d,J=8.5Hz,2H), 4.04(q,J=7.1 Hz,2H), 3.60–3.53(m,1H), 2.85–2.76(m,2H), 1.14(t,J=7.1 Hz,3H)

EXAMPLE 66

(S)-3-[4 [(5-Amidino-2-benzofuranyl)carbonylamino]phenyl]-2-aminopropionic acid (compound 46))

In the same manner as in Example 10, monohydrochloride (224 mg, 0.520 mmol) of compound (45) was hydrolyzed to give 103 mg of dihydrochloride of compound (46) as a colorless solid (45%).

Melting point: >250° C.

IR(KBr): 3200, 1680, 1650, 1600, 1520

$^1$H-NMR (DMSO-d$_6$, 500 MHz) $\delta_{TMS}$: 10.76(s,1H), 9.37 (bs,4H), 8.38(s,1H), 8.05(s,1H), 7.97–7.9 1(m,2H), 7.76(d, J=8.6Hz,2H), 7.29(d,J=8.6 Hz,2H), 3.58–3.56(m,1H), 3.14 (dd,J=14.4,4.8 Hz,2H), 2.97(dd,J=14.4,2.9 Hz,2H)

EXAMPLE 67

(1) Ethyl (S)-3-(4-aminophenyl)-2-[3-(4-methoxyphenyl) propionylamino]propionate 3-(4-Hydroxyphenyl)propionic acid (1.36 g, 8.18 mmol) and methyl iodide (1.20 ml, 19.3 mmol) were dissolved in N,N-dimethylformamide (20 ml) and potassium carbonate (3.40 g, 24.6 mmol) was added. The mixture was stirred at 50°–60° C. for 4 hours and at room temperature for 14 hours. The reaction mixture was filtrated and the filtrate was added to saturated brine (1 00 ml) and extracted with ethyl acetate. The extract was dried over anhydrous magnesium sulfate. After filtration, low boiling matters were distilled away from the filtrate under reduced pressure and the residue was purified by silica gel column chromatography (n-hexane/ethyl acetate=4/1) to give 1.35 g of methyl 3-(4-methoxyphenyl)propionate as a colorless solid (85%). This solid (1.30 g, 6.69 mmol) was dissolved in tetrahydrofuran (10 ml) and a 1N aqueous sodium hydroxide solution (7.0 ml, 7.0 mmol) was added. The mixture was stirred at room temperature for 2 hours. 1N Hydrochloric acid was added to the reaction mixture to adjust its pH to 2–3, and the resulting precipitate was collected by filtration and washed with water to give 1.11 g of 3-(4-methoxyphenyl)propionic acid as a colorless solid (92%).

Then, 3-(4-methoxyphenyl)propionic acid (330 mg, 1.83 mmol) and ethyl (S)-2-amino-3-(4-nitrophenyl)propionate hydrochloride (500 mg, 1.82 mmol) were dissolved in N,N-dimethylformamide (30 ml). 1-(3-Dimethylaminopropyl)-3-ethylcarbodiimide (384 mg, 2.00 mmol), 1-hydroxy-1H-benzotriazole (270 mg, 2.00 mmol) and N-methylmorpholine (0.25 ml, 2.27 mmol) were added, and the mixture was stirred at room temperature for 21hours. Water (500 ml) was added to the reaction mixture and the mixture was extracted with ethyl acetate. The extract was washed with saturated brine and dried over anhydrous magnesium sulfate. After filtration, low boiling matters were distilled away, from the filtrate under reduced pressure, and the residue was purified by silica gel column chromatography (n-hexane/ethyl acetate=2/1) to give 292 mg of ethyl (S)-2-[3-(4-methoxyphenyl)propionylamino]-3-(4-nitrophenyl)propionate as a colorless solid (40%). This solid (280 mg, 0.699 mmol) was dissolved in ethanol (30 ml) and 10% palladium-carbon (100 mg) was added. The mixture was refluxed under heating for 14 hours under a hydrogen atmosphere. The reaction mixture was cooled to room temperature and filtrated. Low boiling matters were distilled away from the filtrate under reduced pressure and the residue was purified by silica gel column chromatography (n-hexane/ethyl acetate=1/1-3/7) to give 171 mg of ethyl (S)-3-(4-aminophenyl)-2-[3-(4-methoxyphenyl) propionylamino]propionate as a colorless solid (66%).

IR(KBr): 3350, 3300, 3200, 1740, 1640, 1510, 1250 cm$^{-1}$ $^1$H-NMR (CDCl$_3$) $\delta_{TMS}$: 7.11(d,J=8.6 Hz,2H), 6.82(d,J=8.6 Hz,2H), 6.73(d,J=8.4 Hz,2H), 6.55(d,J=8.4 Hz,2H), 5.80 (d,J=7.7 Hz,1H), 4.15(q,J=7.1 Hz,2H), 3.78(s,3H), 3.59(bs, 2H), 2.97–2.85(m,4H), 2.49–2.39(m,2H), 1.25(t,J=7.1 Hz,3H)

(2) Ethyl (S)-3-[4-[(5-amidino-2-benzofuranyl) carbonylamino]phenyl]-2-[3-(4-methoxyphenyl) propionylamino]propionate (compound (43))

5-(Benzyloxycarbonylamidino)-2-benzofurancarboxylic acid (151mg, 0.447 mmol) and ethyl (S)-3-(4-aminophenyl) -2-[3-(4-methoxyphenyl)-propionylamino]propionate (165 mg, 0.445 mmol) were dissolved in N,N-dimethylformamide (10 ml), and PyBOP (benzotriazol-1-yl-oxy-tris(pyrrolidino) phosphonium hexafluorophosphate) (225 mg, 0.490 mmol) and N-methylmorpholine (0.05 ml, 0.455 mmol) were added. The mixture was stirred at room temperature for 15 hours. Water (20 ml) was added to the reaction mixture, and the resulting precipitate was collected by filtration and washed with water to give 271mg of ethyl (S)-3-[4-[[5-(benzyloxycarbonylamidino)-2-benzofuranyl] carbonylamino]phenyl]-2-[3-(4-methoxyphenyl) propionylamino]propionate as a colorless solid (88%).

IR(KBr): 3300, 1730, 1650, 1620, 1580, 1510, 1250 cm$^{-1}$ $^1$H-NMR (DMSO-d$_6$) $\delta_{TMS}$: 10.56(s,1H), 9.26(bs,2H), 8.30(d,J=7.7 Hz,1H), 8.11 (dd,J=8.9,1.8 Hz,1H), 7.86(s,1H), 7.81 (d,J=8.9 Hz,1H), 7.71 (d,J=8.5 Hz,2H), 7.44–7.32(m, 5H), 7.19(d,J=8.5 Hz,2H), 7.06(d,J=8.6 Hz,2H), 6.79(d,J= 8.6 Hz,2H), 5.14(s,2H), 4.48–4.40(m,1H ), 4.06(q,J=7.1Hz, 2H), 3.69(s,3H), 3.00–2.87(m,2H), 2.69(t,J=7.0 Hz,2H), 2.35(t,J=7.0 Hz,2H), 1.13(t,J=7.1 Hz,3H)

In the same manner as in Example 17, ethyl (S)-3-[4-[[5-(benzyloxycarbonylamidino)-2-benzofuranyl] carbonylamino]phenyl]-2-[3-(4-methoxyphenyl) propionylamino]propionate (267 mg, 0.387 mmol) was subjected to hydrogen reduction to quantitatively give 230 mg of hydrochloride of compound (43).

$^1$H-NMR (DMSO-d$_6$) $\delta_{TMS}$: 10.84(s,1H), 9.60(bs,2H), 9.44(bs,2H), 8.42(s,1H), 8.38(d,J=6.9 Hz,1H), 8.15(s,1H), 7.97(s,2H), 7.78(d,J=8.5 Hz,2H), 7.20(d,J=8.5 Hz,2H), 7.06 (d,J=8.5 Hz,2H), 6.80(d,J=a.5 Hz,2H), 4.48–4.40(m,1H), 4.06(q,J=7.1 Hz,2H), 3.69(s,3H), 3.11–2.89(m,2H), 2.69(t, J=7.2 Hz,2H), 2.36(t,J=7.2 Hz,2H), 1.13(t,J=7.1 Hz,3H)

EXAMPLE 68

(S)-3-[4-[(5-Amidino-2-benzofuranyl)carbonylamino] phenyl]-2-[3-(4-methoxyphenyl)propionylamino]propionic acid (compound (61))

In the same manner as in Example 10, hydrochloride (230 mg, 0.387 mmol) of compound (43) was hydrolyzed to give 96 mg of hydrochloride of compound (61) as a colorless solid (44%).

Melting point: 187°–191 ° C. (dec.)

IR(KBr): 3200, 1710, 1640, 1560, 1510 cm$^{-1}$ $^1$H-NMR (DMSO-d$_6$) $\delta_{TMS}$: 10.70(s,1H), 9.74(bs,2H), 9.37(bs,2H), 8.37(s,1H), 8.10(d,J-7.0 Hz,1H), 8.00–7.87(m, 3H), 7.72(d,J=8.5 Hz,2H), 7.20(d,J=8.5 Hz,2H), 7.06(d,J= 8.5 Hz,2H), 6.80(d,J=8.5 Hz,2H), 4.45–4.36(m,1H), 3.69(s, 3H), 3.06(dd,J=12,4.0 Hz,1H), 2.84(dd,J=12,8.0 Hz,1H), 2.69(t,J=7.2 Hz,2H), 2.35(t,J=7.2 Hz,2H)

EXAMPLE 69

(1) Ethyl (S) 73-(4-aminophenyl)-2-[(N-benzyloxycarbonyl-4-piperidinyloxy)acetylamino] propionate t-Butyl 4-piperidinyloxyacetate (521 mg, 2.42 mmol) and triethylamine (0.40 ml, 2.9 mmol) were dissolved in methylene chloride (20 ml) and benzyloxycarbonyl chloride (0.41 mmol, 2.9 mmol) was added. The mixture was stirred at room temperature for 74 hours. A saturated aqueous sodium hydrogencarbonate solution (50 ml) was added to the reaction mixture and the mixture was extracted with ethyl acetate. The extract was washed with saturated brine and dried over anhydrous magnesium sulfate. After filtration, low boiling matters were distilled away from the filtrate under reduced pressure. The residue was purified by silica gel column chromatography (n-hexane/ethyl acetate= 2/1) to give 710 mg of t-butyl [N-benzyloxycarbonyl-4-piperidinyloxy]acetate as a colorless oil (84%). Methylene chloride (30 ml) and trifluoroacetic acid (10 ml) were added to this oil (692 mg, 1.99 mmol) and the mixture was stirred at room temperature for 17 hours. Low boiling matters were distilled away from the reaction mixture under reduced pressure to give 555 mg of [N-benzyloxycarbonyl-4-piperidinyloxy]acetate as a colorless solid (96%).

In the same manner as in Example 67 (1), [N-benzyloxycarbonyl-4-piperidinyloxy]acetic acid (530 mg, 1.81 mmol) and ethyl (S)-2-amino-3-(4-nitrophenyl)

propionate hydrochloride (500 mg, 1.82 mmol) were condensed to give 707 mg of ethyl (S)-2-[(N-benzyloxycarbonyl-4-piperidinyloxy)acetylamino]-3-(4-nitrophenyl)propionate as a yellow oil (76%).

In the same manner as in Example 64 (1), the nitro group of ethyl (S)-2-[(N-benzyloxycarbonyl-4-piperidinyloxy) acetylamino]-3-(4-nitrophenyl)propionate (685 mg, 1.33 mmol) was converted to an amino group to give 558 mg of ethyl (S)-3-(4-aminophenyl)-2-[(N-benzyloxycarbonyl-4-piperidinyloxy)acetylamino]propionate as a pale-yellow oil (87%).

IR (neat): 3350, 2920, 1735, 1680–1660, 1100 cm$^{-1}$ $^1$H-NMR (CDCl$_3$) $\delta_{TMS}$: 7.37–7.29(m,5H), 6.95(d,J=8.0 Hz,1H), 6.86(d,J=8.4 Hz,2H), 6.53(d,J=8.4 Hz,2H), 5.12(s, 2H), 4.82–4.73(m,1H), 4.17(q,J=7.2Hz,2H), 3.93(s,2H), 3.68–3.58(m,4H), 3.49–3.42(m,1H), 3.29–3.16(m,2H), 3.02 (d,J=5.8 Hz,2H), 1.78–1.67(m,2H), 1.55–1.43(m,2H), 1.25 (t, J=7.2 Hz,3H)

(2) Ethyl (S)-3-[4-[(5-amidino-2-benzofuranyl) carbonylamino]phenyl]-2-[(4-piperidinyloxy) acetylamino] propionate (compound (44))

In the same manner as in Example 15 (3), 5-(benzyloxycarbonyl-amidino)-2-benzofurancarboxylic acid (187 mg, 0.553 mmol) and ethyl (S)-3-(4-aminophenyl)-2-[(N-benzyloxycarbonyl-4-piperidinyloxy)-acetylamino] propionate (258 mg, 0.533 mmol) were condensed and purified by silica gel column chromatography (chloroform/methanol=99/1) to give 238 mg of ethyl (s)-3-[4-[[(5-(benzyloxycarbonyl-amidino)-2-benzofuranyl] carbonylamino]phenyl]-2-[(N-benzyloxycarbonyl-4-piperidinyloxy)acetylamino]propionate as a colorless solid (56%).

IR(KBr): 3380, 1730, 1680–1660, 1620, 1100 cm$^{-1}$ $^1$H-NMR (CDCl$_3$) $\delta_{TMS}$: 9.07(bs,2H), 8.45(bs,1H), 8.27 (d,J=1.9 Hz,1H), 7.99(dd,J=9.1,1.9 Hz,1H), 7.62–7.56(m, 4H), 7.48–7.30(m,10H), 7.14(d,J=8.5 Hz,2H), 7.00(d,J=8.1 Hz,1H), 5.24(s,2H), 5.11(s,2H), 4.92–4.83(m,1H), 4.20(q, J=5.2 Hz,2H), 3.96(s,2H), 3.78–3.63(m,2H), 3.53–3.49 (m1H), 3.30–3.13(m,4H), 1.78–1.71(m,2H), 1.57–1.51(m, 2H), 1.27(t,J=5.2 Hz,3H)

Ethyl (S)-3-[4-[[5-(benzyloxycarbonylamidino)-2-benzofuranyl]carbonylamino]phenyl]-2-[(N-benzyloxycarbonyl-4-piperidinyloxy)acetylamino] propionate (230 mg, 0.286 mmol) was dissolved in ethanol (50 ml) and 10% palladium-carbon (40 mg) was added. The mixture was stirred at room temperature for 22 hours under a hydrogen atmosphere. The reaction mixture was filtrated and low boiling matters were distilled away from the filtrate under reduced pressure. The residue was purified by silica gel (Chromatorex, NH type, Fuji Silysia Chemical) column chromatography (chloroform/methanol=85/15) to give 85 mg of compound (44) as a colorless solid (55%).

IR(KBr) :3350, 1725, 1650, 1520, 1090 cm$^{-1}$

1H-NMR (CDCl$_3$) $\delta_{TMS}$: 7.97(s,1H), 7.76–7.55(m,8H), 7.16(d,J=8.5 Hz,2H), 7.19–7.08(m,1H), 4.95–4.85(m,1H), 4.20(q,J=7.2 Hz,2H), 3.96(s,2H), 3.43–3.34(m,1H), 3.16–3.14(m,2H), 3.08–2.97(m,2H), 2.64–2.52(m,2H), 1.87–1.81 (m,2H), 1.45–1.32 (m,2H), 1.27(t,J=7.2 Hz,3H)

EXAMPLE 70

(S)-3-[4-[(5-Amidino-2-benzofuranyl)carbonylamino] phenyl]2-[(4-piperidinyloxy)acetylamino]propionic acid (compound (56))

In the same manner as in Example 10, compound (44) (83 mg, 0.155 mmol) was hydrolyzed to quantitatively give 90 mg of dihydrochloride of compound (56) as a colorless solid.

Melting point: >250° C.

IR(KBr): 3350, 1720, 1655, 1530, 1100 cm$^{-1}$ $^1$H-NMR (DMSO-d$_6$, 500 MHz) $\delta_{TMS}$: 12.90(bs,1H), 10.82 (s,1 H), 9.54 (bs,2H), 9.34 (bs,2H), 9.06–8.98(m,2H), 8.40(d,J=1.7 Hz,1H), 8.15(s,1H), 7.97(d,J=8.9 Hz,1H), 7.94 (dd,J=8.9,1.7 Hz,1H), 7.80(d,J=8.3 Hz,1H), 7.76(d,J=8.5 Hz,2H), 7.24(d,J=8.5 Hz,2H), 4.55–4.51 (m,1H), 3.91 (d,J= 15.2 Hz,1H), 3.88 (d,J=15.2 Hz,1 H), 3.55–3.53 (m,1 H), 3.14–3.10 (m,2H), 3.12(dd,J=13.7,4.8 Hz,1H), 3.01 (dd,J= 13.7,9.0 Hz,1H), 2.96–2.91 (m,2H), 1.95–1.89(m,2H), 1.76–1.73(m,2H)

EXAMPLE 71

(1) Ethyl [4-amino-N-(n-valeryl)anilino]acetate

A mixture of 4-nitroaniline (25.0 g, 181 mmol) and ethyl bromoacetate (10.0 ml, 90.5 mmol) was stirred at 80°–90° C. for 20 hours under a nitrogen atmosphere. Ethyl acetate (30 ml) was added to the reaction mixture and the mixture was refluxed under heating for 10 minutes, after which solid was collected by filtration and recrystallized from ethanol to give 13.1 g of ethyl (4-nitroanilino)acetate as a yellow solid (64%). A mixture of this solid (1.00 g, 4.46 mmol) and n-valeryl chloride (1.12 g, 9.36 mmol) was stirred at 80°–90° C. for 2 hours under a nitrogen atmosphere. The reaction mixture was purified by silica gel column chromatography (n-hexane/ethyl acetate=1/1) to give 948 mg of ethyl [4-nitro-N-(n-valeryl)anilino]acetate as a pale-yellow solid (69%). The solid (851 mg, 2.76 mmol) was dissolved in a mixture of chloroform (20 ml) and ethanol (30 ml) and 10% palladium carbon (80 mg) was added. The mixture was stirred at room temperature for 60 hours under a hydrogen atmosphere. After filtration, low boiling matters were distilled away from the filtrate under reduced pressure to give 759 mg of ethyl [4-amino-N-(n-valeryl)anilino]acetate as a colorless oil (99%).

IR (neat): 3600–2300, 1730 cm$^{-1}$ $^1$H-NMR (DMSO-d$_6$) $\delta_{TMS}$: 7.45–7.25(m,4H), 4.30(s, 2H), 4.10 (q,J=7.1 Hz,2H), 2.08(t,J=7.1 Hz,2H), 1.38 (quint, J=7.4 Hz,2H), 1.30–1.03 (m,5H), 0.76 (t,J=7.1 Hz,3H)

(2) Ethyl [4-[(5-amidino-2-benzofuranyl)carbonylamino]-N-(n-valeryl)anilino]acetate (compound (68))

In the same manner as in Example 15 (3), 5-(benzyloxycarbonylamidino)-2-benzofurancarboxylic acid (421mg, 1.24 mmol) and ethyl [4-amino-N-(n-valeryl) anilino]acetate (346 mg, 1.24 mmol) were condensed and purified by silica gel column chromatography (n-hexane/ethyl acetate=3/1-1/1) to give 308 mg of ethyl [4-[[5-(benzyloxycarbonylamidino)- 2-benzofuranyl] carbonylamino]-N-(n-valeryl)anilino]acetate as a pale-yellow solid (42%).

IR(KBr) :3600–2700, 1740, 1610 cm$^{-1}$ $^1$H-NMR (CDCl$_3$) $\delta_{TMS}$: 8.80(s,1H), 8.21(s,1H), 7.96(d, J=9.0 Hz,1H), 7.85–7.75(m,2H), 7.60–7.18(m,4H+5H), 5.22(s,2H), 4.35 (s,2H), 4.17(q,J=7.0Hz,2H), 2.14(t,J=7.2 Hz,2H), 1.54(quint,J=7.2 Hz,2H), 1.40–1.10(m,8H), 0.78 (t,J=7.2 Hz,3H)

Chloroform (25 ml) and methanol (25 ml) were added to ethyl [4-[[5-(benzyloxycarbonylamidino)-2-benzofuranyl] carbonylamino]-N-(n-valeryl)anilino]acetate (351 g, 0.587 mmol), and 10% palladium carbon (30 mg) and 1N hydrochloric acid (1.2 ml, 1.2 mmol) were added. The mixture was stirred at room temperature for one hour under a hydrogen atmosphere. The reaction mixture was filtrated and low boiling matters were distilled away from the filtrate under reduced pressure. The residue was purified by silica gel column chromatography (chloroform/methanol=4/1) to give 281mg of hydrochloride of compound (68) as a yellow solid (95%).

IR(KBr): 3600–2800, 1730, 1640, 1505 cm$^{-1}$ $^1$H-NMR (DMSO-d$_6$, 500 MHz) δ$_{TMS}$: 8.38(s,1H), 8.08 (s,1H), 8.00(d,J=5 Hz,1H), 7.95–7.88(m,3H), 7.40–7.35(m, 2H), 4.32(s,2H), 4.11(q,J=7.3 Hz,2H), 2.10(t,J=7.3 Hz,2H), 1.43(quint,J=7.3 Hz,2H), 1.25–1.12(m,5H), 0.77(t,J=7.3 Hz,3H)

EXAMPLE 72

[4-[(5-Amidino-2-benzofuranyl)carbonylamino]-N-(n-valeryl)anilino]acetic acid (compound (74))

In the same manner as in Example 10, hydrochloride (202 mg, 0.404 mmol) of compound (68) was hydrolyzed and purified by reversed-phase column (Chromatorex-ODS DM1020T, Fuji Silysia Chemical) chromatography (water-acetonitrile) to give 60 mg of hydrochloride of compound (74) as a yellow solid (28%).

Melting point: 216°–230° C. (dec.)

IR(KBr): 3600–2500, 1650, 1600 cm$^{-1}$ $^1$H-NMR (DMSO-d$_6$, 500 MHz) δ$_{TMS}$: 9.41(bs,2H), 9.13 (bs,2H), 8.35(s,1H), 8.05–7.85(m,5H), 7.45–7.36(m,2H), 4.20(s,2H), 2.09(t,J=7.5 Hz,2H), 1.50–1.40(m,2H), 1.26–1.13(m,2H), 0.83–0.73(m,3H)

EXAMPLE 73

(1) Ethyl [4-amino-N-(benzyloxycarbonyl)anilino]acetate

4-Nitroaniline (25.0 g, 181mmol) and ethyl bromoacetate (10.0 ml, 90.5 mmol) were stirred at 80°–90° C. for 20 hours under a nitrogen atmosphere. Ethyl acetate (30 ml) was added to the reaction mixture and the mixture was refluxed under heating for 10 minutes. The obtained solid was collected by filtration and recrystallized from ethanol to give 13.1 g of ethyl (4-nitroanilino)acetate as a yellow solid (64%). This solid (1.00 g, 4.46 mmol) and benzyloxycarbonyl chloride (8 ml) were stirred at 80°–90° C. for 1.5 hours under a nitrogen atmosphere. Toluene (20 ml) was added to the reaction mixture and low boiling matters were distilled away under reduced pressure, which was followed by purification by silica gel column chromatography (n-hexane/ethyl acetate=5/2) to quantitatively give 962 mg of ethyl [4-nitro-N-(benzyloxycarbonyl)anilino]acetate as a yellow oil. Ethanol (100 ml) and water (30 ml) were added to the oil (716 mg, 2.00 mmol) and activated zinc (6.55 g, 100 mmol) and calcium chloride (2.22 g, 20.0 mmol) were added, which was followed by refluxing under heating for 2 hours. The reaction mixture was filtrated and low boiling matters were distilled away from the filtrate under reduced pressure. Water (100 ml) was added to the residue and the mixture was extracted with ethyl acetate. The extract was washed with water and saturated brine, and dried over anhydrous magnesium sulfate. After filtration, low boiling matters were distilled away from the filtrate under reduced pressure to give 576 mg of ethyl [4-amino-N-(benzyloxycarbonyl)anilino]acetate as a yellow oil (88%).

$^1$H-NMR (DMSO-d$_6$, 500 MHz) δ$_{TMS}$: 7.35–7.20(m,5H), 6.97–6.91 (m,2H), 6.53–6.47(m,2H), 5.06(s,2H), 4.23(s,2 H), 4.11(q,J=7.1 Hz,2H), 1.17(t,J=7.1 Hz,3H)

(2) Ethyl [4-[[5-(benzyloxycarbonylamidino)-2-benzofuranyl]carbonylamino]-N-(benzyloxycarbonyl) anilino]acetate (compound (69))

In the same manner as in Example 15(3), 5-(benzyloxycarbonylamidino)-2-benzofurancarboxylic acid (567 mg, 1.68 mmol) and ethyl [4-amino-N-(benzyloxycarbonyl)anilino]acetate (550 mg, 1.68 mmol) were condensed and purified by silica gel column chromatography (n-hexane/ethyl acetate=2/1-1/1) to give 857 mg of compound (69) as a yellow solid (82%).

$^1$H-NMR (DMSO-d$_6$, 500 MHz) δ$_{TMS}$: 8.50(s,1H), 8.13–8.11(m,1H), 7.88–7.78(m,4H), 7.45–7.30(m,12H), 5.13(s,2H×2), 4.39(s,2H), 4.03(q,J=7.1 Hz,2H), 1.19(t,J=7.1 Hz,3H)

EXAMPLE 74

[4-[(5-Amidino-2-benzofuranyl)carbonylamino]anilino] acetic acid (compound (70))

In the same manner as in Example 17, compound (69) (857 mg, 1.32 mmol) was subjected to hydrogen reduction to convert the compound to ethyl [4-[(5-amidino-2-benzofuranyl)carbonylamino]anilino]acetate. Then, in the same manner as in Example 10, the compound was hydrolyzed to give 125 mg of dihydrochloride of compound (70) as a yellow solid (22%).

Melting point: >235° C. (dec.)

IR(KBr): 1730, 1650, 1610, 1580 cm$^{-1}$ $^1$H-NMR (DMSO-d$_6$, 500 MHz) δ$_{TMS}$: 10.44(s,1H), 9.45 (bs,2H), 9.20(bs,2H), 8.34(s,1H), 8.10–7.87(m 7.55–7.53 (m,2H), 6.66–6.63(m,2H), 3.8 4(s,2H)

EXAMPLE 75

(1) t-Butyl (4-hydroxycyclohexyloxy)acetate

Sodium hydroxide (5.7 g, 0.14 mol) was dissolved in water (6 ml) and 1,4-cyclohexanediol (cis/trans=6/4) (15.0 g, 0.13 mol) was added, which was followed by stirring at room temperature for 30 minutes. Then, tetrabutylammonium bromide (20.8 g, 0.065 mol) and t-butyl bromoacetate (24.5 ml, 0.13 mol) were added, and the mixture was stirred at room temperature for one hour. The reaction mixture was extracted with ethyl acetate. The extract was dried over anhydrous magnesium sulfate. After filtration, low boiling matters were distilled away from the filtrate under reduced pressure and the residue was purified by silica gel column Chromatography (n-hexane/ethyl acetate=5/1-2/1) to give 2.13 g of t-butyl (4-hydroxycyclohexyl)acetate as a transparent oil (7%).

IR(KBr): 3400, 2910, 2850, 1740 cm$^{-1}$ $^1$H-NMR (CDCl$_3$) δ$_{TMS}$: 3.98, 3.97(each s,2H), 3.85–3.61 (m,1H), 3.58–3.27(m,1H), 2.18–1.10(m,17H)

(2) t-Butyl [4-[(5-amidino-2-benzofuranyl)carbonyloxy] cyclohexyloxy]acetate (compound (151))

Thionyl chloride (8 ml, 110 mmol) was added to 5-cyano-2-benzofurancarboxylic acid (1.00 g, 5.34 mmol) and the mixture was refluxed under heating for 30 minutes. Thionyl chloride was distilled away under reduced pressure and toluene (3 ml) was added which was again distilled away under reduced pressure to give 5-cyano-2-benzofurancarbonyl chloride. This was dissolved in toluene (20 ml) and pyridine (0.86 ml, 10.7 mmol), 4-dimethylaminopyridine (131 mg, 1.07 mmol) and t-butyl 4-hydroxycyclohexylacetate (1.35 g, 5.88 mmol) were added. The mixture was refluxed under heating for one hour. Water was added to the reaction mixture and the mixture was extracted with ethyl acetate. The extract was dried over anhydrous magnesium sulfate. After filtration, low boiling matters were distilled away from the filtrate under reduced pressure and the residue was purified by silica gel column chromatography (n-hexane/ethyl acetate=10/1-5/1) to give 1.12 g of t-butyl [4-[(5-cyano-2-benzofuranyl)carbonyloxy] cyclohexyloxy]acetate as a colorless solid (52%).

IR(KBr): 3400, 2950, 2200, 1740, 1719, 1620, 1580 cm$^{-1}$ $^1$H-NMR (CDCl$_3$) δ$_{TMS}$: 8.10–8.02(m,1H), 7.78–7.63(m, 2H), 7.55(d,J=2.0 Hz,1H), 5.23–5.00(m,1H), 4.02, 4.01 (each s,2H), 3.53–3.40(m,1H), 2.27–1.52(m,8H), 1.49(s, 9H)

In the same manner as in Example 1 (3), the cyano group of t-butyl [4-[(5-cyano-2-benzofuranyl)carbonyloxy] cyclohexyloxy]acetate (1.00 g, 2.50 mmol) was converted to an amidino group to give 1.00 g of hydriodide of compound (151) as a pale-brown solid (73%).

IR(KBr): 3200, 2950, 1720, 1670 cm$^{-1}$ $^1$H-NMR (CDCl$_3$) $\delta_{TMS}$: 12.0–8.40(bs,4H), 8.30 (s,1H), 8.08–7.79 (m,3H), 5.19–4.90 (m,1H), 4.02(s,2H), 3.65–3.35 (m,1H), 2.15–1.25(m,17H)

EXAMPLE 76

[4-[(5-Amidino-2-benzofuranyl)carbonyloxy] cyclohexyloxy]acetic acid (compound (.152))

In the same manner as in Example 2, hydriodide (1.00 g, 1.84 mmol) of compound (151) was treated with trifluoroacetic acid (10 ml) to give 520 mg of hydriodide of compound (152) as a pale-brown solid (58%).

$^1$H-NMR (DMSO-d$_6$) $\delta_{TMS}$: 9.39(s,2H), 9.10(s,2H), 8.30 (s,1H), 8.09–7.81(m,3H), 5.15–4.88(m,1H), 4.05(s,2H), 3.65–3.35(m,1H), 2.17–1.31 (m,8H) MS (SIMS, m/z): 361 (M+H)

Acetic acid (10 ml) and concentrated sulfuric acid (12 µl, 0.23 mmol) were added to hydriodide (300 mg, 0.61 mmol) of compound (152) and the mixture was stirred at 90° C. for 10 minutes. The reaction mixture was cooled to room temperature and added with diethyl ether (50 ml). The precipitated sediment was washed with diethyl ether and collected by filtration to give 220 mg of sulfate of compound (152) as a colorless solid (78%).

Melting point: 186°–188° C.

IR(KBr): 3300, 3120, 2920, 1720, 1670, 1618 cm$^{-1}$ $^1$H-NMR (DMSO-d$_6$) $\delta_{TMS}$: 9.39(s,2H), 9.06(s,2H), 8.31 (s,1H), 8.09–7.81 (m,3H), 5.15–4.88(m,1H), 4.05(s,2H), 3.35–3.65(s,1H), 2.17–1.12(m,8H) (cis/trans were about equivalent amounts)

EXAMPLE 77

Ethyl 3-[4-[(5-amidino-2-benzofuranyl)carbonyloxy] piperidino]propionate (compound (193))

In the same manner as in Example 75 (2), 5-cyano-2-benzofurancarboxylic acid (1.00 g, 5.34 mmol) was converted a corresponding acid chloride and reacted with ethyl 3-(4-hydroxypiperidino)propionate (1.08 g, 5.77 mmol). The reaction mixture Was purified by silica gel column chromatography (chloroform) to give 733 mg of ethyl 3-[4-[(5-cyano-2-benzofuranyl)carbonyloxy]piperidino] propionate as a colorless solid (33%).

$^1$H-NMR (DMSO-d$_6$) $\delta_{TMS}$: 8.37(s,1H), 8.00(d,J=14.4 Hz,1H), 7.92(d,J=14.4 Hz,1H), 7.84(s,1H) 5.06–4.92(m,] H), 4.07(q,J=7.1 Hz,2H), 2.73–2.58(m,6H), 2.52–2.43(m, 2H), 2.02–1.92(m,2H), 1.91(t,J=7.1 Hz,3H), 1.75–1.63(m, 2H), In the same manner as in Example 1 (3), the cyano group of ethyl 3-[4-[(5-cyano-2-benzofuranyl)carbonyloxy] piperidino]propionate (723 mg, 1.78 mmol) was converted to an amidino group and purified by silica gel (Chromatorex, NH type, Fuji Silysia Chemical) column chromatography (chloroform/methanol=85/15) to give 140 mg of compound (193) as a colorless solid (20%).

$^1$H-NMR (CDCl$_3$) $\delta_{TMS}$: 7.96(s,1H), 7.72(d,J=8.6 Hz,1H), 7.60(d,J=8.6 Hz,1H), 7.53(s,1H), 5.14–5.04(m,1H), 4.62(bs,3H), 4.15(q,J=7.1 Hz,2H), 2.82–2.63(m,4H), 2.54–2.33(m,4H), 2.11–1.80(m,4H), 1.27(t,J=7.1 Hz,3H)

EXAMPLE 78 t-Butyl trans-[4-[(6-amidino-2-indolyl)carbonylamino] cyclohexyloxy]acetate (compound (2 10))

In the same manner as in Example 1 (2), 6-cyano-2-indolecarboxylic acid (244 mg, 1.31mmol) and t-butyl trans-(4-aminocyclohexyloxy)acetate (300 mg, 1.3 mmol ) were condensed. The reaction mixture was purified by silica gel column chromatography (chloroform/methanol=50/1-1/1) to give 465 mg of t-butyl trans-[4-[(6-cyano-2-indolyl) carbonylamino]cyclohexyloxy]acetate as a brown solid (89%).

IR(KBr): 3600–3000, 2900, 2200, 1730, 1630, cm$^{-1}$ $^1$H-NMR (CDCl$_3$) $\delta_{TMS}$: 9.96(bs,1H), 7.79(s,1H), 7.71(d, J=8.3 Hz,1H), 7.35(dd,J=8.3,1.4 Hz,1H), 6.86(d,J=1.3 Hz,1H), 6.09(d,J=7.9 Hz,1H), 4.02(s,2H), 4.12–3.90(m,1H), 3.50–3.30(m,1H), 2.27–2.05(m,4H), 1.49(s,9H), 1.75–1.15 (m,4H)

In the same manner as in Example 1 (3), the cyano group of t-butyl trans-[4-[(6-cyano-2-indolyl)carbonylamino] cyclohexyloxy]acetate (465 mg, 1.17 mmol) was converted to an amidino group to give 343 mg of hydriodide of compound (210) as a brown solid IR (KBr): 3600–2800, 1725, 1660, 1630, 1530 cm$^{-1}$ $^1$H-NMR (DMSO-d$_6$) $\delta_{TMS}$: 12.23(bs,1H), 9.50–8.45(br, 4H), 7.89(s,1H), 7.84(d,J=8.5 Hz,1H), 7.41 (dd,J=8.4,1.5 Hz,1H), 7.28(s,1H), 4.01 (s,2H), 3.92–3.67(m,1H), 2.10–1.80(m,4H), 1.43(s,9H), 1.55–1.10(m,4H)

EXAMPLE 79 trans-[4-[(6-Amidino-2-indolyl)carbonylamino] cyclohexyloxy]acetic acid (compound (21 2))

In the same manner as in Example 2, hydriodide (824 mg, 1.52 mmol) of compound (210) was treated with trifluoroacetic acid (6 ml) to give 641 mg of hydriodide of compound (212) as a brown solid (87%).

IR (KBr): 3600–2800, 1720, 1670, 1630, 1520 cm$^{-1}$ $^1$H-NMR (DMSO-d$_6$) $\delta_{TMS}$: 12.24(s,1H), 9.25(bs,2H), 8.89(bs,2H), 8.45(d,J=7.6 Hz,1H), 7.90(s,1H), 7.84(d,J=8.5 Hz, 1H), 7.41(dd,J=8.4,1.3 Hz,1H), 7.29(s,1H), 4.04(s,2H), 3.90–3.65(m,1H), 2.20–1.78(m,4H), 1.55–1.10(m,4H)

EXAMPLE 80

Ethyl trans-[4-[(6-Amidino-2-indolyl)carbonylamino] cyclohexyloxy]acetate (compound (209))

In the same manner as in Example 42, hydriodide (641 mg, 1.32 mmol) of compound (212) was reacted with ethanol to give 495 mg of methanesulfonate of compound (209) as a pale-yellow solid (78%).

Melting point: 263°–266° C.

IR(KBr) :3600–2800, 1745, 1670, 1630, 1560, 1530 cm$^{-1}$ $^1$H-NMR (DMSO-d$_6$) $\delta_{TMS}$: 12.20(bs,1H), 9.24(bs,2H), 8.83(bs,2H), 8.42(d,J=7.8 Hz,1H), 7.90(s,1H), 7.84(d,J=8.4 Hz,1H), 7.41(dd,J=8.5,1.5 Hz,1H), 7.29(d,J=1.5 Hz,1H), 4.13(s,2H), 4.13(q,J=7.1 Hz,2H), 3.90–3.70(m,1H) 2.35(s, 3H), 2.15–1.82(m,4H), 1.21(t,J=7.1 Hz,3H), 1.55–1.15(m, 4H)

EXAMPLE 81 trans-[4-[(6-Amidinobenzo[b]thien-2-yl)carbonylamino] cyclohexyloxy]acetic acid (compound (232))

In the same manner as in Example 1 (2), 6-cyanobenzo [b]thiene-2-carboxylic acid (400 mg, 1.97 mmol) and t-butyl trans-3-(4-aminocyclohexyl)propionate (474 mg, 2.07 mmol) were condensed to give 471 mg of t-butyl trans-[4-[(6-cyanobenzo[b]thien-2-yl)carbonylamino] cyclohexyloxy]acetate as an orange solid (58%).

IR(KBr): 3700–3000, 2200, 1730, 1620 cm$^{-1}$ $^1$H-NMR. (DMSO-d$_6$) $\delta_{TMS}$: 8.64(d,J=1.5 Hz,1H), 8.20 (s,1H), 8.12(d,J=8.3 Hz,1H), 7.79(dd,J=8.3,1.5 Hz,1H), 3.80–3.70(m,1H), 2.08–1.98(m,3H), 1.95–1.85(m,2H), 1.43 (s,9H), 1.45–1.35(m,2H), 1.33–1.23(m,2H)

In the same manner as in Example 1 (3), the cyano group of t-butyl trans-[4-[(6-cyanobenzo[b]thien-2-yl) carbonylamino]cyclohexyloxy]acetate (450 mg, 1.09 mmol) was converted to an amidino group and the reaction mixture was purified by silica gel (Chromatorex, NH type, Fuji Silysia Chemical) column chromatography (chloroform/ methanol=6/1) to give about 147 mg of t-butyl trans-[4-[(6-amidinobenzo[b]thien-2-yl)carbonylamino]cyclohexyloxy] acetate as a yellow solid. In the same manner as in Example 2, this solid was treated with trifluoroacetic acid (2 ml) to give 104 mg of trifluoroacetate of compound (232) as a yellow solid (20%).

Melting point: >250° C.

IR(KBr): 3700–2700, 1740, 1670, 1600 cm$^{-1}$ $^1$H-NMR (DMSO-d$_6$, 500 MHz) $\delta_{TMS}$: 9.40(bs,2H), 9.18 (bs,2H), 8.69(d,J=7.8 Hz,1H), 8.53(s,1H), 8.23(s,1H), 8.15 (d,J=8.5 Hz,1H), 7.78(dd,J=8.5,1.5 Hz, 1H), 4.04(s,2H), 3.80–3.70(m,1H), 3.43(m1H), 2.13–2.00(m,2H), 1.97–1.85 (m,2H), 1.45–1.35(m,2H), 1.33–1.20(m,2H)

EXAMPLE 82

Ethyl trans-[4-[(6-Amidinobenzo[b]thien-2-yl) carbonylamino]cyclohexyloxy]acetate (compound (230))

In the same manner as in Example 42, ethanol was reacted with trifluoroacetate (85 mg, 0.174 mmol) of compound (232) to quantitatively give 89 mg of methanesulfonate of compound (230) as a colorless solid.

$^1$H-NMR (DMSO-d$_6$) $\delta_{TMS}$: 9.38(bs,2H), 9.01 (bs,2H), 8.70(d,J=8.0 Hz,1H), 8.52(s,1H), 8.23(s,1H), 8.16(d,J=8.5 Hz,1H), %78(d,J=8.5 Hz,1H), 4.13(s,2H), 4.12(q,J=7.1 Hz,2H), 3.85–3.65(m,1H), 2.35(s,3H), 2.15–1.85(m,4H), 1.21(t,J=7.1 Hz,3H), 1.50–1.15(m,4H)

EXAMPLE 83

(1) Ethyl (S)-3-(4-aminophenyl)-2-(trifluoromethylsulfonylamino)propionate

Acetonitrile (100 ml) was added to hydrochloride (4.00 g, 14.6 mmol) of ethyl (S)-2-amino-3-(4-nitrophenyl) propionate and trifluoromethylsulfonyl chloride (2.5 ml, 23.5 mmol) and then N-methylmorpholine (3.2 ml, 29.1 mmol) were added. The mixture was stirred at room temperature for 2 hours. Water (100 ml) was poured into the reaction mixture and the mixture was extracted with ethyl acetate. The extract was washed with water and dried over anhydrous magnesium sulfate. After filtration, low boiling matters were distilled away from the filtrate under reduced pressure and the residue was purified by silica gel column chromatography (chloroform/n-hexane=2/1) to give 2.25 g of ethyl (S)-2-(trifluoromethylsulfonylamino)-3-(4-nitrophenyl) propionate as a yellow solid (42%). This solid (1.97 g, 5.32 mmol) was dissolved in acetic acid (100 ml) and 10% palladium-carbon (750 mg) was added. The mixture was stirred at room temperature for 66 hours under a hydrogen atmosphere. The reaction mixture was filtered through Celite and acetic acid was distilled away from the filtrate under reduced pressure. The residue was washed with water to quantitatively give 1.81 g of ethyl (S)-3-(4-aminophenyl) -2-(trifluoromethylsulfonyl-amino)propionate as a yellow solid.

$^1$H-NMR (CDCl$_3$) $\delta_{TMS}$: 6.90(d,J=8.4 Hz,2H), 6.62(d,J= 8.4 Hz,2H), 4.72(bs,3H), 4.42(dd,J=5.9,5.3 Hz,1H), 4.21(q, J=7.2 Hz,2H), 3.10(dd,J=14.1.5.3 Hz,1H), 2.98(dd,J= 14.1.5.9 Hz,1H), 1.27(t,J=7.2 Hz,3H)

(2) Ethyl (S)-3-[4-[(5-amidino-2-benzofuranyl) carbonylamino]phenyl]-2-(trifluoromethylsulfonylamino) propionate (compound (54))

In the same manner as in Example 15 (3), 5-(benzyloxycarbonylamidino)-2-benzofurancarboxylic acid (1.02 g, 3.01mmol) and ethyl (S)-3-(4-aminophenyl)-2-(trifluoromethylsulfonylamino)propionate (1.03 g, 3.03 mmol) were condensed. The reaction mixture was purified by silica gel column chromatography (n-hexane/ethyl acetate=1/1-1/2) to give 1.31 g of ethyl (S)-3-[4-[[5-(benzyloxycarbonylamidino)-2-benzofuranyl] carbonylamino]phenyl]-2-(trifluoromethylsulfonylamino) propionate as a colorless solid (65%). Ethanol (200 ml), 10% palladium-carbon (450 mg) and 1N hydrochloric acid (2 ml) were added to this solid (1.30 g, 1.97 mmol) and the mixture was stirred at room temperature for 2 hours under a hydrogen atmosphere. The reaction mixture was filtrated and low boiling matters were distilled away from the filtrate under reduced pressure to quantitatively give 1.11 g of hydrochloride of compound (54) as a colorless solid.

$^1$H-NMR (DMSO-d$_6$) $\delta_{TMS}$: 10.71(s,1H), 10.26(bs,1H), 9.46(bs,2H), 9.18(bs,2H), 8.37(d,J=1.3 Hz,1H), 8.02(s,1H), 7.99(d,J=8.6 Hz,1H), 7.90(dd,J=8.6,1.3 Hz,1H), 7.78(d,J= 8.7 Hz,2H), 7.29(d,J=8.7 Hz,2H), 4.17(q,J=7.1 Hz,2H), 3.44 (dd,J=10.1.5.0 Hz,1H), 3.14(dd,J=13.8,5.0 Hz,1H), 2.8(dd, J=13.8,10.1 Hz,1H), 1.97(t,J=7.1 Hz,3H)

EXAMPLE 84

(S)-3-[4-[(5-Amidino-2-benzofuranyl)carbonylamino] phenyl]-2-(trifluoromethylsulfonylamino)propionic acid (compound (55))

2.5N Hydrochloric acid (50 ml) and acetic acid (10 ml) were added to compound (54) (180 mg, 0.320 mmol) and the mixture was refluxed under heating for 3 hours. The reaction mixture was concentrated under reduced pressure and the precipitated solid was washed with water and dilute hydrochloric acid to give 30 mg of hydrochloride of compound (55) as a colorless solid (18%).

$^1$H-NMR (DMSO-d$_6$+TFA) $\delta_{TMS}$: 10.74(s,1H), 10.07(d, J=8.9 Hz,1H), 9.50(bs,2H), 9.29(bs,2H), 8.39(d,J=1.6 Hz,1H), 8.05(s,1H), 7.99(d,J=8.9 Hz,1H), 7.93(dd,J=8.9,1.6 Hz,1H), 7.79(d,J=8.5 Hz,2H), 7.30(d,J=8.5 Hz,2H), 4.18–4.05(m,1H), 3.18(dd,J=1 4.0,4.3 Hz,1H), 2.84 (dd,J= 14.0,13.5 Hz,1 H)

EXAMPLE 85 t-Butyl trans-[4-[(5-amidino-2-benzofuranyl) carbonylamino]cyclohexyloxy]acetate (compound (176))

Compound (170) (925 mg, 1.68 mmol) was dissolved in t-butanol (120 ml) and 10% palladium-carbon (200 mg) was added. The mixture was refluxed under heating for 2 hours under a hydrogen atmosphere. The reaction mixture was cooled to room temperature and filtered through Celite. Low boiling matters were distilled away from the filtrate under reduced pressure and the residue was purified by silica gel (Chromatorex, NH type, Fuji Silysia Chemical) column chromatography (chloroform/methanol=20/1-3/1) to give 665 mg of compound (176) as a colorless solid (95%). This solid (400 mg, 0.963 mmol) was dissolved in tetrahydrofuran (24 ml) and a solution of methanesulfonic acid (93 mg, 0.963 mmol) dissolved in tetrahydrofuran (6 ml) was dropwise added under ice-cooling. The mixture was stirred for 10 minutes. Diethyl ether (30 ml) was added to the reaction mixture and the precipitated sediment was washed with diethyl ether and collected by filtration to give 425 mg of methanesulfonate of compound (176) as a colorless solid (86%).

IR(KBr): 3600–2700, 1720, 1670, 1632, 1594, 1525 cm$^{-1}$ $^1$H-NMR (DMSO-d$_6$) $\delta_{TMS}$: 9.35(bs,2H), 8.95(bs,2H), 8.62(d,J=7.9 Hz,1H), 8.28(s,1H), 7.92(d,J=8.6 Hz,1H), 7.84 (dd,J=8.8,1.7 Hz,1H), 7.71 (s,1H), 4.00(s,2H), 3.90–3.68(m, 1H), 3.40–3.20(m,1H), 2.32(s,3H), 2.12–1.80(m,4H), 1.43 (s,9H), 1.60–1.15(m,4H)

EXAMPLE 86

(1) t-Butyl trans-3-(4-aminocyclohexyl)propionate t-Butyl β-[4-(benzyloxycarbonylamino)cyclohexyl] acrylate (60.0 g) obtained in the same manner as in Example 13 (1) was recrystallized from a mixed solvent of n-hexane and ethyl acetate to give 23.5 g of a trans compound thereof (cyclohexyl ring) (39%). This compound was dissolved in methanol (150 ml) and 10% palladium-carbon (250 mg) was added. The mixture was stirred at room temperature for 20 hours under a hydrogen atmosphere. The reaction mixture was filtrated and low boiling matters were distilled away from the filtrate under reduced pressure to quantitatively give 14.9 g of t-butyl trans-3-(4-aminocyclohexyl) propionate as a colorless solid.

$^1$H-NMR (CDCl$_3$) $\delta_{TMS}$: 7.35(s,5H), 6.78(dd,J=15.7,6.8 Hz,1H), 5.70(d,J=15.7 Hz,1H), 5.09(bs,1H), 4.59(bs,1H), 3.56–3.30(m,1H), 2.12–1.95(m,3H), 2.87–2.70(m,2H), 1.45 (s,1H), 1.32–1.02(m,4H)

(2) t-Butyl trans-3-[4-[(5-amidino-2-benzofuranyl) carbonylamino]cyclohexyl]propionate (compound (161))

In the same manner as in Example 15 (3), 5-(benzyloxycarbonylamidino)-2-benzofurancarboxylic acid (3.98 g, 11.8 mmol) and t-butyl trans-3-(4-aminocyclohexyl)propionate (2.70 g, 1 1.8 mmol) were condensed to give 5.04 g of t-butyl trans-3-[4-[[5-(benzyloxycarbonylamidino)-2-benzofuranyl] carbonylamino]cyclohexyl]propionate as a colorless solid (78%). In the same manner as in Example 85, this solid (4.90 g, 8.95 mmol) was subjected to hydrogen reduction to give 3.52 g of compound (161) as a colorless solid (95%), which was treated with methanesulfonic acid (0.82 g, 8.52 mmol) in tetrahydrofuran solvent to give 3.82 g of methanesulfonate of compound (161) as a colorless solid (88%).

$^1$H-NMR (DMSO-d$_6$) $\delta_{TMS}$: 9.36(bs,2H), 9.00(bs,2H), 8.6(d,J=8.1 Hz,1H), 8.27(s,1H), 8.00–7.80(m,2H), 7.71(s, 1H), 3.90–3.60(m,1H), 2.32(s,3H), 2.25–2.10(m,2H), 1.95–1.68(m,4H), 1.43 (s,9H), 1.60–0.85(m,7H)

EXAMPLE 87

(1) t-Butyl trans-(4-aminocyclohexyl-N-n-butylamino) acetate

In the same manner as in Example 56 (1), trans-1,4-diaminocyclohexane (12.0 g, 105 mmol) was reacted with triphenylmethyl chloride (14.7 g, 52.5 mmol) to give 11.1 g of trans-1-amino-4-(triphenylmethylamino)cyclohexane as a colorless solid (30%). This solid (2.00 g, 5.61 mmol) and n-butylaldehyde (400 mg, 5.61 mmol) were dissolved in ethanol (70 ml) and a suspension of sodium cyanoborohydride (220 mg, 3.64 mmol) suspended in ethanol (30 ml) was dropwise added. Then, acetic acid (0.6 ml) was added to adjust its pH to 6–7 and the mixture was stirred at room temperature for 14 hours. Water (200 ml) was added to the reaction mixture and the mixture was concentrated to ⅓ under reduced pressure. The condensate was extracted with chloroform and the extract was dried over anhydrous magnesium sulfate. After filtration, low boiling matters were distilled away from the filtrate under reduced pressure and the residue was purified by silica gel (Chromatorex, NH type, Fuji Silysia Chemical) column chromatography (n-hexane/chloroform=5/1) to give 1.72 g trans-1-(n-butylamino)-4-(triphenylmethylamino)cyclohexane as a colorless oil (74%). This oil (1.72 g, 4.17 mmol) and potassium carbonate (1.21 g, 8.75 mmol) were added to N,N-dimethylformamide (80 ml) and t-butyl bromoacetate (850 mg, 4.38 mmol) was dropwise added at room temperature, followed by stirring for 4.5 hours. The reaction mixture was filtrated and water (100 ml) was added to the filtrate. The mixture was extracted with ethyl acetate. The extract was washed with water and saturated brine, and dried over anhydrous magnesium sulfate. After filtration, low boiling matters were distilled away from the filtrate under reduced pressure and the residue was purified by silica gel column chromatography (n-hexane/ethyl acetate=20/1-10/1) to give 1.88 g of t-butyl trans-[4-(triphenylmethylamino) cyclohexyl-N-n-butylamino]acetate as a colorless oil (86%). This oil (1.74 g, 3.31 mmol) was dissolved in ethanol (60 ml) and 10% palladium-carbon (520 mg) was added. The mixture was refluxed under heating for 4 hours under a hydrogen atmosphere. The reaction mixture was filtered through Celite and low boiling matters were distilled away from the filtrate under reduced pressure. Water (30 ml) and 1N hydrochloric acid (10 ml) were added to the residue and the mixture was extracted with diethyl ether. Sodium hydrogencarbonate was added to the aqueous layer to make same alkaline and the mixture was extracted with chloroform. The extract was dried over anhydrous sodium sulfate. After filtration, low boiling matters were distilled away from the filtrate under reduced pressure to give 680 mg of t-butyl trans-(4-aminocyclohexyl-N-n-butylamino)acetate as a yellow oil (72%).

IR(KBr): 3500–3000, 2900, 1730, 1590, 1450 cm$^{-1}$ $^1$H-NMR (CDCl$_3$) $\delta_{TMS}$: 3.20(s,2H), 2.75–2.45(m,4H), 2.05–1.70(m,4H), 1.45(s,9H), 1.60–1.00(m,8H), 0.90(t,J= 7.0 Hz,3H)

(2) t-Butyl trans-[4-[(5-amidino-2-benzofuranyl) carbonylamino]cyclohexyl-N-n-butylamino]acetate (compound (197))

In the same manner as in Example 15 (3), 5-(benzyloxycarbonylamidino)-2-benzofurancarboxylic acid (785 mg, 2.32 mmol) and t-butyl trans-(4-aminocyclohexyl-N-n-butylamino) acetate (680 mg, 2.32 mmol) were condensed and purified by silica gel column chromatography (n-hexane/ethyl acetate=1/1-1/4) to give 1.06 g of t-butyl trans-[4-[[5-(benzyloxycarbonylamidino)-2-benzofuranyl]carbonylamino]cyclohexyl-N-n-butylamino]acetate as a colorless solid (75%).

IR(KBr): 3600–3000, 2900, 1720, 1635, 1510, 1440 cm$^{-1}$ $^1$H-NMR (CDCl$_3$) $\delta_{TMS}$: 8.23(d,J=1.9 Hz,1H), 7.95(dd, J=8.7,1.9 Hz,1H), 7.60–7.20(m,7H), 6.43(d,J=8.3 Hz,1H), 5.23(s,2H), 4.05–3.80(m,1H), 3.23(s,2H), 2.80–2.45(m,3H), 2.30–1.80(m,4H), 1.46(s,9H), 1.60–1.15(m,8H), 1.05–0.75 (m,3H)

In the same manner as in Example 57, t-butyl trans-[4-[ [5-(benzyloxycarbonylamidino)-2-benzofuranyl] carbonylamino]cyclohexyl-N-n-butylamino]acetate (941 mg, 1.56 mmol) was subjected to hydrogen reduction and purified by silica gel (Chromatorex, NH type, Fuji Silysia Chemical) column chromatography (chloroform/methanol= 20/1-2/1) to give 625 mg of compound (197) as a pale-yellow solid (85%).

IR(KBr): 3600–3000, 2900, 1720, 1635, 1520, 1450 cm$^{-1}$ $^1$H-NMR (CDCl$_3$) $\delta_{TMS}$: 7.94(s,1H), 7.80–7.60 (m,1H), 7.60–7.35 (m,2H), 6.60–6.30 (m,1H), 4.10–3.80(m,1H), 3.23(s,2H), 2.80–2.40(m,3H), 2.30–1.80(m,4H), 1.46(s,9H), 1.65–1.10 (m,8H), 1.00–0.85(m,3H)

EXAMPLE 88 trans-[4-[(5-Amidino-2-benzofuranyl)carbonylamino]cyclohexyl-N-n-butylamino]acetic acid (compound (198))

In the same manner as in Example 2, compound (197) (100 mg, 0.212 mmol) was treated with trifluoroacetic acid (10 ml) to give 120 mg of ditrifluoroacetate of compound (198) as a colorless solid (88%).

IR(KBr): 3600–2800, 1665, 1530, 1450 cm$^{-1}$ $^1$H-NMR (DMSO-d$_6$, 500 MHz) $\delta_{TMS}$: 9.37 (bs,2H), 9.29(bs,2H), 8.74(d,J=8.1 Hz,1H), 8.29(d,J=1.9 Hz,1H), 7.91 (d,J=8.8 Hz,1H), 7.86(dd,J=8.8,1.9 Hz,1H), 7.72(s, 1H), 4.10(s,2H), 3.95–3.80 (m,1H), 3.40–3.05(m,3H), 2.10–1.90(m,4H), 1.78–1.55(m,4H), 1.55–1.40(m,2H), 1.40–1.25(m,2H), 0.92 (t,J=7.4 Hz,3H)

EXAMPLE 89

(1) t-Butyl 4-(5-cyanofuro[2,3-b]pyridine-2-carbonylamino)phenoxy-acetate

5-Cyanofuro[2,3-b]pyridine-2-carboxylic acid (108 mg, 0.574 mmol) and t-butyl 4-aminophenoxyacetate (141 mg, 0.632 mmol) were dissolved in N,N-dimethylformamide (10 ml) and 1-hydroxy-1H-benzotriazole (85.3 mg, 0.632 mmol) and 1-(3-dimethylaminopropyl)-3-ethylcarbodiimide hydrochloride (121 mg, 0.632 mmol) were added. The mixture was stirred at room temperature for 14 hours. Water (100 ml) was poured into the reaction mixture and the mixture was extracted with ethyl acetate. The extract was washed with water and brine, and dried over anhydrous magnesium sulfate. Low boiling matters were distilled away under reduced pressure. The residue was purified by silica gel column chromatography (ethyl acetate/hexane=1/1) to quantitatively give 232 mg of t-butyl 4-(5-cyanofuro[2,3-b]pyridine-2-carbonylamino)phenoxyacetate as a pale-yellow solid.

$^1$H-NMR (DMSO-d$_6$) $\delta_{TMS}$: 10.69(bs,1H), 8.96(d,J=2.0 Hz,1H), 8.90(d,J=2.0 Hz,1H), 7.84(s,1H), 7.74–7.65(m,2H), 6.95–6.85(m,2H), 4.65(s,2H), 1.44(s,9H)

(2) t-Butyl 4-(5-amidinofuro[2,3-b]pyridine-2-carbonylamino)phenoxy-acetate (compound (238))

t-Butyl 4-(5-cyanofuro[2,3-b]pyridine-2-carbonylamino)phenoxy-acetate (430 mg, 1.10 mmol) was dissolved in a mixed solvent of pyridine (16 ml) and triethylamine (4 ml), and a hydrogen sulfide gas was blown in for 10 minutes. The mixture was stirred at room temperature for 18 hours. The solvent was distilled away from the reaction mixture under reduced pressure to give t-butyl 4-(5-thiocarbamoylfuro[2,3-b]pyridine-2-carbonylamino)phenoxyacetate as a yellow solid. This solid was dissolved in acetone (15 ml) and methyl iodide (1.0 ml) was added, which was followed by refluxing under heating for 1.5 hours. Low boiling matters were distilled away from the reaction mixture under reduced pressure to give t-butyl 4-[5-[(1-methylthio)iminomethyl]furo[2,3-b]pyridine-2-carbonylamino]phenoxy-acetate as a yellow solid. Methanol (15 ml) and ammonium acetate (150 mg, 1.95 mmol) were added and the mixture was refluxed under heating for 2 hours. Low boiling matters were distilled away from the reaction mixture under reduced pressure and the residue was purified by silica gel (Chromatorex, NH type, Fuji Silysia Chemical) column chromatography (chloroform/methanol=5/1) to give 35 mg of compound (238) as a yellow solid (11% in 3 steps).

$^1$H-NMR (DMSO-d$_6$) $\delta_{TMS}$: 8.87(d,J=2.2 Hz,1H), 8.75(d, J=2.2 Hz,1H), 7.93(s,1H), 7.75–7.64(m,2H), 6.96–6.85(m, 2H), 4.66(s,2H), 1.44(s,9H)

EXAMPLE 90

4-(5-Amidinofuro[2,3-b]pyridine-2-carbonylamino)-phenoxyacetic acid (compound (239))

Methylene chloride (1.5 ml) was added to compound (238) (28 mg, 0.068 mmol) and trifluoroacetic acid (0.5 ml) was added. The mixture was stirred at room temperature for 2 hours. Diethyl ether (15 ml) was added to the reaction mixture and the mixture was stirred for 10 minutes. The resulting precipitate was collected by filtration to give 22 mg of ditrifluoroacetate of compound (239) as a yellow solid (56%).

IR(KBr): 3350, 1660, 1600, 1500 cm$^{-1}$ $^1$H-NMR (DMSO-d$_6$) $\delta_{TMS}$: 10.69(bs,1H), 9.53(bs,2H), 9.38(bs,2H), 8.87(d,J=2.1 Hz,1H), 8.75(d,J=2.1 Hz,1H), 7.92(s,1H), 7.75–7.67(m,2H), 6.97–6.90(m,2H) 4.67(s,2H)

Melting point: >250° C.

EXAMPLE 91

(1) Ethyl 5-amidinofuro[2,3-b]pyridine-2-carboxylate hydrochloride

Ethyl 5-cyanofuro[2,3-b]pyridine-2-carboxylate (773 mg, 4.14 mmol) was dissolved in a mixed solvent of pyridine (40 ml) and triethylamine (8 ml), and a hydrogen sulfide gas was blown in for 10 minutes. The mixture was stirred at room temperature for 14 hours. The solvent was distilled away from the reaction mixture under reduced pressure to give ethyl 5-thiocarbamoylfuro[2,3-b]pyridine-2-carboxylate as a yellow solid. Acetone (80 ml) and methyl iodide (8.0 ml) were added and the mixture was refluxed under heating for one hour. Low boiling matters were distilled away from the reaction mixture under reduced pressure to give ethyl 5-[(1-methylthio)-iminomethyl]furo[2,3-b]pyridine-2-carboxylate. Methanol (80 ml) and ammonium acetate (694 mg, 9.00 mmol) were added and the mixture was refluxed under heating for 3.5 hours. Low boiling matters were distilled away from the reaction mixture under reduced pressure and the residue was purified by silica gel column chromatography (chloroform/methanol=97/3-4/1) to give 2.05 g of ethyl 5-amidinofuro[2,3-b]pyridine-2-carboxylate hydrochloride as a yellow solid (69% in 3 steps).

$^1$H-NMR (DMSO-d$_6$, 500) $\delta_{TMS}$: 8.89(s,1H), 8.73(s,1H), 7.98(s,1H), 4.2(q,J=7.1 Hz,2H), 1.37(t,J=7.1 Hz,3H)

(2) 5-(Benzyloxycarbonylamidino)furo[2,3-b]pyridine-2-carboxylic acid

Tetrahydrofuran (32 ml) was added to ethyl 5-amidinofuro[2,3-b]pyridine-2-carboxylate hydrochloride (2.05 g, 5.10 mmol), and benzyl chloroformate (1.09 ml, 7.65 mmol) was dropwise added under ice-cooling while maintaining the mixture at pH 10–12 with a 1N aqueous sodium hydroxide solution. Thereafter, the mixture was stirred under ice-cooling for 30 minutes and at room temperature for 1.5 hours. Tetrahydrofuran (20 ml) and a 1N aqueous sodium hydroxide solution (20 ml) were added to this reaction mixture and the mixture was stirred at room temperature for 1.5 hours. The mixture was adjusted to pH 4–5 with 1N hydrochloric acid and low boiling matters were distilled away under reduced pressure. The residue was purified by reversed-phase column (Chromatorex-ODS DM1020T, Fuji Silysia Chemical) chromatography. (water-acetonitrile) to give 695 mg of 5-(benzyloxycarbonylamidino)furo[2,3-b]pyridine-2-carboxylic acid as a yellow solid (35%).

$^1$H-NMR (DMSO-d$_6$, 500 MHz) $\delta_{TMS}$: 9.01 (d,J=2.2 Hz,1H), 8.73(d,J=2.2 Hz,1H), 7.73(s,1H), 7.50–7.30(m,8H), 5.14(s,2H)

(3) Ethyl 5-[5-(benzyloxycarbonylamidino)furo[2,3-b]pyridine-2-carbonylamino]-2-pyridyloxyacetate (compound (243))

5-(Benzyloxycarbonylamidino)furo [2,3-b]pyridine-2-carboxylic acid (100 mg, 0.295 mmol) and ethyl 5-amino-2-pyridyloxyacetate (62.3 mg, 0.324 mmol) were dissolved in N,N-dimethylformamide (15 ml), and 1-hydroxy-1H-benzotriazole (43.7 mg, 0.324 mmol) and 1-(3-dimethylaminopropyl)-3-ethylcarbodiimide hydrochloride (62.2 mg, 0.324 mmol) were added. The mixture was stirred at room temperature for 16 hours. Water (100 ml) was poured into the reaction mixture and the mixture was extracted with ethyl acetate. The extract was washed with water and brine, and dried over anhydrous magnesium sulfate. Low boiling matters were distilled away under reduced pressure and the residue was purified by silica gel column chromatography (ethyl acetate/hexane=1/1) to give 68 mg of compound (243) as a pink solid (45%). $^1$H-NMR (CDCl$_3$) $\delta_{TMS}$: 8.92, 8.97(each s,1H), 8.53, 8.67(each s,1H), 8.41–8.32(m,1H), 8.10–8.03(m,1H), 7.62, 7.63(each s,1H), 7.45–7.30(m,5H), 6.94–6.90(m,1H), 5.25, 5.28(each s,2H), 4.89(s,2H), 4.24(q,J=7.1 Hz,2H), 1.28(t,J=7.1 Hz,3H)

EXAMPLE 92

Ethyl 5-(5-amidinofuro[2,3-b]pyridine-2-carbonylamino)2-pyridyloxyacetate (compound (245))

Chloroform (5 ml), ethanol (5 ml), 1N hydrochloric acid (0.6 ml, 0.6 mmol) and 10% palladium-carbon (20 mg) were added to compound (243) (68 mg, 0.13mmol), and the mixture was stirred at room temperature for 1.5 hours under a hydrogen atmosphere. The reaction mixture was filtrated and low boiling matters were distilled away from the filtrate under reduced pressure. The residue was purified by silica gel column chromatography (chloroform/methanol=4/1) to give 42 mg of trihydrochloride of compound (245) as a yellow solid (66%).

$^1$H-NMR (DMSO-d$_6$, 500 MHz) $\delta_{TMS}$: 8.89(d,J=2.2 Hz,1H), 8.76(d,J=2.2 Hz,1H), 8.53(d,J=2.6 Hz,1H), 8.15 (dd,J=2.6,9.0 Hz,1H), 7.99(s,1H), 6.99(d,J=9.0 Hz,1H), 4.90(s,2H), 4.14(q,J=7.1 Hz,2H), 1.20(t,J=7.1 Hz,3H)

EXAMPLE 93

5-(5-Amidinofuro[2,3-b]pyridine-2-carbonylamino)-2-pyridyloxyacetic acid (compound (246))

Tetrahydrofuran (0.5 ml ) and a 1N aqueous sodium hydroxide solution (0.43 ml, 0.43 mmol) were added to trihydrochloride (42 mg, 0.085 mmol) of compound (245), and the mixture was stirred at room temperature for 2 hours. The reaction mixture was adjusted to pH 2–3 with 1N hydrochloric acid and concentrated under reduced pressure. The resulting precipitate was filtrated to give 36 mg of trihydrochloride of compound (246) as a colorless solid (92%).

IR(KBr): 3600–2700, 1660, 1590, 1520 cm$^{-1}$ $^1$H-NMR (DMSO-d$_6$, 500 MHz) $\delta_{TMS}$: 9.60(bs,2H), 9.37 (bs,2H), 8.89(d,J=2.2 Hz,1H), 8.77(d,J=2.2 Hz,1H), 8.53(d, J=2.6 Hz,1H), 8.14(dd,J=2.6,8.9 Hz,1H), 7.99(s,1H), 6.96 (d,J=8.9 Hz,1H), 4.79(s,2H)

Melting point: >250° C.

EXAMPLE 94 t-Butyl trans-[4-(5-amidinofuro[2,3-b]pyridine-2-carbonylamino)cyclohexyloxy]acetate (compound (254))

In the same manner as in Example 89 (1), 5-cyanofuro [2,3-b]-pyridine-2-carboxylic acid (288 mg, 1.53 mmol) and ethyl trans-4-aminocyclohexyloxyacetate (433 mg, 1.89 mmol) were condensed to give 280 mg of t-butyl trans-4-(cyanofuro[2,3-b]pyridine-2-carbonylamino)-cyclohexyloxyacetate as a colorless solid (46%)

IR(KBr): 2200, 1740, 1650, 1460 cm$^{-1}$ $^1$H-NMR (CDCl$_3$) $\delta_{TMS}$: 8.72(d,J=2.0 Hz,1H), 8.36(d,J=2.0 Hz,1H), 7.53(s, 1H), 6.57(d,J=6.3 Hz,1H), 4.01(s,2H), 4.10–3.90(m,1H), 3.50–3.30(m,1H), 2.40–2.10(m,1H), 1.48(s,9H), 1.90–1.20 (m,4H)

In the same manner as in Example 89(2), the cyano group of t-butyl trans-4-(5-cyanofuro[2,3-b]pyridine-2-carbonylamino)cyclohexyloxyacetate (275 mg, 0.69 mmol) was converted to an amidino group to give 66 mg of compound (254) is a colorless solid (23% in 3 steps).

IR(KBr): 1750, 1650 cm$^{-1}$ $^1$H-NMR (CDCl$_3$) $\delta_{TMS}$: 8.75(bs,1H), 8.35(bs,1H), 7.47 (s,1H), 7.00–6.50(bs,1H), 5.50–4.00(bs,3H), 4.01 (s,2H), 4.10–3.90(m,1H), 3.55–3.30(m,1H), 2.40–2.00(m,4H), 1.49 (s,9H), 1.70–1.25(m,4H)

EXAMPLE 95 trans-[4-(5-Amidinofuro[2,3-b]pyridine-2-carbonylamino)-cyclohexyloxy]acetic acid (compound (255))

In the same manner as in Example 90, compound (254) (65 mg, 0.16 mmol) was treated with trifluoroacetic acid (1.5 ml) to give 60 mg of ditrifluoroacetate of compound (255) as a yellow solid (65%).

IR(KBr): 1660, 1530, 1380 cm$^{-1}$ $^1$H-NMR (DMSO-d$_6$) $\delta_{TMS}$: 9.54(bs,1H), 9.22(bs,1H), 8.83(d,J=2.0 Hz,1H), 8.69(d,J=2.0 Hz,1H), 7.74(s,1H), 4.03 (s,2H), 3.95–3.65(m,1H), 2.10–2.00(m,2H), 1.60–1.50(m, 2H), 1.70–1.05(m,4H)

Melting point: 135°–160° C. (dec.)

EXAMPLE 96

Ethyl trans-3-[4-[5-(benzyloxycarbonylamidino)furo[2,3-b] pyridine-2-carbonylamino]cyclohexyl]propionate (compound (257))

In the same manner as in Example 91 (3), 5-(benzyloxycarbonylamidino)furo[2,3-b]pyridine-2-carboxylic acid (2 15 mg, 0.634 mmol) and ethyl trans-3-(4-aminocyclohexyl)propionate (149 mg, 0.634 mmol) were condensed to give 193 mg of compound (257) as a colorless solid (59%).

IR(KBr): 1745, 1710, 1620, 1500 cm$^{-1}$ $^1$H-NMR (CDCl$_3$, 500 MHz) $\delta_{TMS}$: 8.94–8.89(m,1H), 8.58, 8.50(each s,1H), 7.50–7.25(m,6H), 6.70–6.62(m,1H), 5.23, 5.22(each s,2H), 4.13(q,J=7.1 Hz,2H), 3.95–3.85(m, 1H), 2.45–2.25(m,2H), 2.18–2.05(m,2H), 1.90–1.75(m,2H), 1.67–1.50(m,2H), 1.49–1.20(m,6H), 1.18–1.05(m,2H)

EXAMPLE 97

Ethyl trans-3-[4-(5-amidinofuro[2,3-b]pyridine-2-carbonylamino)cyclohexyl]propionate (compound (260))

In the same manner as in Example 92, compound (257) (183 mg, 0.352 mmol) was subjected to hydrogen reduction in the presence of 10% palladium-carbon (30 mg) to give 77 mg of dihydrochloride of compound (260) as a yellow solid (48%). In-so-doing, 70 mg of compound (257) was recovered.

IR(KBr): 3700–3000, 1710, 1620 cm$^{-1}$ $^1$H-NMR (DMSO-d$_6$, 500 MHz) δ$_{TMS}$: 9.60–9.20(bs,4H), 8.84(s,1H), 8.84–8.80(m1H), 8.71 (s,1H) 7.75(s,1H), 4.06 (q,J=7.2 Hz,2H), 3.90–3.70(m,1H), 2.34–2.27(m,2H), 1.90–1.70(m,4H), 1.58–1.35(m,4H), 1.30–1.15(m,4H), 1.13–0.95(m,2H)

EXAMPLE 98 trans-3-[4-(5-Amidinofuro[2,3-b]pyridine-2-carbonylamino)cyclohexyl]propionic acid (compound (261))

In the same manner as in Example 93, dihydrochloride (67 mg, 0.15 mmol) of compound (260) was hydrolyzed with a 1N aqueous sodium hydroxide solution (0.58 ml, 0.58 mmol) to give 28 mg of dihydrochloride of compound (261) as a colorless solid (43%).

IR(KBr): 3600–2600, 1680, 1610, 1570 cm$^{-1}$ $^1$H-NMR (DMSO-d$_6$, 500 MHz) δ$_{TMS}$: 9.64(bs,2H), 9.43(bs,2H), 8.85 (d,J=2.2 Hz,1H), 8.83(bs,1H), 8.73(d,J=2.2 Hz,1H), 7.77(s, 1H), 3.83–3.71 (m,1H), 2.35–2.20(m,2H), 1.95–1.70(m, 4H), 1.50–1.35(m,4H), 1.08–0.95(m,2H)

Melting point: >250° C.

EXAMPLE 99:

Preparation of inclusion compound of compound (167) by α-cyclodextrin

Sulfate (2.50 g, 5.49 mmol) of compound (167) and α-cyclodextrin (7.50 g, 7.71 mmol) were added to distilled water (300 ml) and the mixture was hated to 70° C. to completely dissolve the same. This solution was filtrated and the filtrate was lyophilized to give 10.00 g of a powder (inclusion compound). This powder (16 mg) was dissolved in distilled water (200 μl ) at room temperature and left standing at room temperature for one day. As a result, solid matter was not precipitated.

EXAMPLE 100:

Preparation of inclusion compound of compound (179) by 2-hydroxypropyl-β-cyclodextrin Sulfate (2.50 g, 5.46 mmol) of compound (179) and 2-hydroxypropyl-β-cyclodextrin (10.00 g, 7.49 mmol, Research Biochemicals International, H-J07) were added to distilled water (400 ml) and the mixture was heated to 70° C. to completely dissolve the same. This solution was filtrated and the filtrate was lyophilized to give 12.50 g of a powder (inclusion compound). This powder (50 mg) was dissolved in distilled water (1 ml) at room temperature and left standing at room temperature for one day. As a result, solid matter was not precipitated.

Experimental Example 1

Determination of suppressive activity on ADP aggregation of human platelets

Platelet rich plasma was prepared from the blood taken from healthy humans by centrifugation in the presence of 0.38% sodium citrate, and used for the determination.

Two minutes after the test compounds shown in Table 1 were added to the above-mentioned platelet rich plasma, ADP (adenosine-5'-diphosphate) (1–5 μM) having a concentration at which primary aggregation alone is observed was added, and the suppression of ADP aggregation by the compounds was evaluated. The percent suppression was determined by varying the concentration of the compounds and the concentration of the compound at which the aggregation was suppressed by 50% (IC$_{50}$) was calculated, which was taken as the activity of the compound.

The results are shown in Table 19.

TABLE 19

| | Suppression of platelet aggregation (IC$_{50}$ μM) |
|---|---|
| Compound 5 | 0.1 |
| Compound 10 | 0.03 |
| Compound 12 | 0.23 |
| Compound 16 | 0.04 |
| Compound 21 | 0.1 |
| Compound 29 | 0.03 |
| Compound 35 | 0.5 |
| Compound 37 | 0.04 |
| Compound 46 | 0.06 |
| Compound 48 | 0.01 |
| Compound 55 | 0.07 |
| Compound 56 | 0.03 |
| Compound 61 | 0.03 |
| Compound 70 | 0.15 |
| Compound 74 | 0.23 |
| Compound 95 | 0.06 |
| Compound 118 | 0.2 |
| Compound 134 | 0.7 |
| Compound 135 | 0.02 |
| Compound 152 | 0.08 |
| Compound 159 | 0.07 |
| Compound 163 | 0.45 |
| Compound 164 | 0.18 |
| Compound 165 | 0.01 |
| Compound 167 | 0.006 |
| Compound 179 | 0.01 |
| Compound 182 | 0.03 |
| Compound 184 | 0.15 |
| Compound 191 | 0.16 |
| Compound 192 | 0.02 |
| Compound 193 | 0.32 |
| Compound 195 | 0.02 |
| Compound 202 | 0.23 |
| Compound 203 | 1.75 |
| Compound 204 | 0.009 |
| Compound 209 | 0.1 |
| Compound 212 | 0.03 |
| Compound 232 | 0.02 |
| Compound 239 | 0.01 |
| Compound 246 | 0.03 |
| Compound 255 | 0.02 |
| Compound 261 | 0.01 |

Formulation Example 1

Tablet

| | |
|---|---|
| (1) Compound (I) of Invention | 10 mg |
| (2) Fine particles No. 209 for direct compression (Fuji Chemical) | 46.6 mg |
| Magnesium aluminosilicate | 20% |
| Corn starch | 30% |
| Lactose | 50% |
| (3) Crystalline cellulose | 24.0 mg |
| (4) Calcium carboxymethylcellulose | 4.0 mg |
| (5) Magnesium stearate | 0.4 mg |

(1), (3) and (4) are previously passed through a 100 mesh sieve. (1), (3), (4) and (2) were previously dried to predetermined water contents and mixed in a mixer in the above-mentioned weight proportions. (5) was added to the homogeneous powder mixture and mixed for a short time (30 seconds). The powder mixture was compressed (pounder: 6.3 mmφ, 6.0 mmR) to give tablets weighing 85 mg per tablet.

These tablets may be coated with conventionally-employed enteric film coating (e.g. polyvinylacetal diethylaminoacetate) or food dye as necessary.

Formulation Example 2:

Capsules

| (1) Compound (I) of Invention | 50 g |
|---|---|
| (2) Lactose | 935 g |
| (3) Magnesium stearate | 15 g |

The above ingredients were respectively weighed and uniformly mixed. The powder mixture was filled in hard gelatin capsules by 200 mg.

Formulation Example 3

Injections

| (1) Hydrochloride of Compound (I) of Invention | 5 mg |
|---|---|
| (2) Sucrose | 100 mg |
| (3) Physiological saline | 10 ml |

The mixed solution of the above ingredients was filtered through a membrane filter and again filtered for sterilization. The filtrate was aseptically dispensed to vials, filled with nitrogen gas and sealed to give intravenous injections.

The novel carboxylic acid compound having a condensed ring and pharmacologically acceptable salt thereof of the present invention have superior GPIIb/IIIa antagonism in mammals inclusive of human; can be administered orally; have long life in blood and low toxicity; and show less side-effects. Accordingly, they are extremely useful for the prophylaxis and treatment of thrombotic diseases and other diseases.

What is claimed is:

1. A carboxylic acid compound having a condensed ring, which is represented by the formula (I)

[Structural formula (I) showing fused ring with substituents A, $R_1$, $R_2$, U, L, and CO—M—B]

wherein

A is a group of the formula (1)

$$E-HN-C(=NH)-$$ (1)

wherein E is hydrogen, alkyl or a protecting group for amidino, guanidino or amino, or a group of the formula (2)

$$E-HN-C(=NH)-NH-$$ (2)

wherein E is as defined above; B is a group of the formula (3)

[Structural formula (3) showing ring with $R^3$, $R^4$, W, and (D)]

wherein D is a group of the formula (i)

$$-(Q)_p-(CH_2)_q-(CH)_r-COOR^5$$ (i)

with G substituent on the CH wherein $R^5$ is hydrogen, alkyl, cycloalkyl or aralkyl, Q is —O—, —S— —$NR^6$—wherein $R^6$ is hydrogen, alkyl, cycloalkyl, aralkyl, alkylsulfonyl, aralkylsulfonyl, arylsulfonyl, alkanoyl, aralkanoyl, aroyl, heteroarylcarbonyl or —$(CH_2)_d$—$COOR^7$ wherein $R^7$ is hydrogen, alkyl, cycloalkyl or aralkyl and d is 1, 2 or 3, G is hydrogen, hydroxy, alkyl, cycloalkyl, phenyl, biphenylyl, pyridyl, aralkyl or $E^1$-$NR^8$-wherein $E^1$ is hydrogen, alkyl or a protecting group for amino and $R^8$ is hydrogen, alkyl, cycloalkyl or aralkyl, p and r are each independently 0 or 1 and q is 0, 1, 2 or 3, provided that when p≠o, at least one of q and r is not 0, W is =CH— or =N—, $R^3$ and $R^4$ may be the same or different and each hydrogen, alkyl, halogen, alkanoyl, aralkanoyl, aroyl, heteroarylcarbonyl or an alkoxy and e is 1 or 2, or a group of the formula (4)

[Structural formula (4) showing ring with $R^3$, T—D, and $(CH_2)_f$]

wherein T is —CH< or —N<, D is a group of the aforementioned formula (i), provided that when T is —N<, p is 0, $R^3$ is as defined above and f is 1, 2 or 3;

L is —O—, —$NR^9$— wherein $R^9$ is hydrogen, alkyl, cycloalkyl, aralkyl, alkanoyl, aralkanoyl, aroyl, or heteroarylcarbonyl or —S—;

M is —$NR^{10}$—wherein $R^{10}$ is hydrogen, alkyl, cycloalkyl or aralkyl, —O— or —S—;

U is =CH—; and $R^1$ and $R^2$ may be the same or different and each is a hydrogen, a hydroxy, an alkyl, a halogen, an amino, alkanoyl, an aralkanoyl, an aroyl, an heteroarylcarbonyl or an alkoxy, or a pharmacologically acceptable salt thereof.

2. The carboxylic acid compound having a condensed ring of claim 1, wherein, in the formula (I), B is a group of the formula (3) or (4) and, in D of the formula (i), p+q+r≦3, or a pharmacologically acceptable salt thereof.

3. The carboxylic acid compound having a condensed ring of claim 1 or claim 2, wherein, in the formula (I), B is a group of the formula (3) and, in D of the formula (i), p+q+r=2, or a pharmacologically acceptable salt thereof.

4. The carboxylic acid compound having a condensed ring of claim 1 or claim 2, wherein, in the formula (I), B is a group of the formula (4), f=2, and, in D of the formula (i), p+q+r=2, or a pharmacologically acceptable salt thereof.

5. The carboxylic acid compound having a condensed ring of claim 1, wherein, in the formula (I), L is —O—, or a pharmacologically acceptable salt thereof.

6. The carboxylic acid compound having a condensed ring of claim 1, which is one member selected from the group consisting of 4-[(5-amidino-2-benzofuranyl)carbonylamino]phenoxyacetic acid, [[4-[(5-amidino-2-benzofuranyl)carbonylamino]-o-phenylene]dioxy]diacetic acid, 3-[4-[(5-amidino-2-benzofuranyl)carbonylamino]phenyl]-2-(n-butylsulfonylamino)propionic acid, ethyl trans-3-[4-[(5-amidino-2-benzofuranyl)carbonylamino]cyclohexyl]propionate, trans-3-[4-[(5-amidino-2-benzofuranyl)carbonylamino]cyclohexyl]propionic acid, ethyl trans-[4-

[(5-amidino-2-benzofuranyl)carbonylamino] cyclohexyloxy]acetate, trans-[4-[(5-amidino-2-benzofuranyl)carbonylamino]cyclohexyloxy]acetic acid, 3-[4-[(5-amidino-2-benzofuranyl)carbonylamino] piperidino]propionic acid, di-t-butyl trans-[4-[(5-amidino-2-benzofuranyl)carbonylamino]cyclohexylamino]diacetate, trans-[4-[(5-amidino-2-benzofuranyl)carbonylamino] cyclohexylamino]diacetic acid and trans-[4-[(6-amidinobenzo[b]thien-2-yl)carbonylamino]cyclohexyloxy] acetic acid, or a pharmacologically acceptable salt thereof.

7. An inclusion compound comprising a compound of the formula (I')

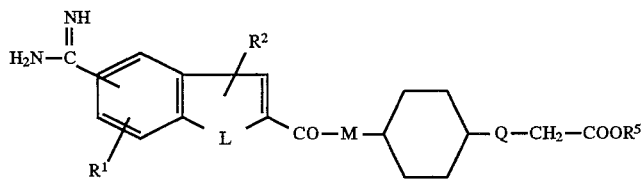

(I')

wherein $R^5$ is a hydrogen, an alkyl, a cycloalkyl or an aralkyl;

Q is —O—, —S— —NR$^6$— wherein R$^6$ is hydrogen, alkyl, cycloalkyl, aralkyl, alkylsulfonyl, aralkylsulfonyl, arylsulfonyl, alkanoyl, aralkanoyl, aroyl, heteroarylcarbonyl or —(CH$_2$)$_d$—COOR$^7$ wherein $R^7$ is hydrogen, alkyl, cycloalkyl or aralkyl, and d is 1, 2 or 3;

L is —O—, —NR$^9$— wherein R$^9$ is hydrogen, alkyl, cycloalkyl, aralkyl, alkanoyl, aralkanoyl, aroyl, or heteroarylcarbonyl or —S—;

M is —NR$^{10}$— wherein R$^m$ is hydrogen, alkyl, cycloalkyl or aralkyl, —O— or —S—; and $R^1$ and $R^2$ may be the same or different and each is a hydrogen, a hydroxy, an alkyl, a halogen, an amino, an alkanoyl, an aralkanoyl, an aroyl, an heteroarylcarbonyl or an alkoxy, or a salt thereof, and cyclodextrin or a derivative of cyclodextrin.

8. A pharmaceutical composition comprising a carboxylic acid compound having a condensed ring of any one of claim 1 or a pharmacologically acceptable salt thereof and a pharmaceutically acceptable carrier.

9. A pharmaceutical composition comprising the inclusion compound of claim 7 and a pharmaceutically acceptable carrier.

10. A method for antagonizing GPIIb/IIIa in a mammal which comprises administering to the mammal a GPIIb/IIIa antagonistic amount of a compound of claim 1.

11. A method for antagonizing GPIIb/IIIa in a mammal which comprises administering to the mammal a GPIIb/IIIa antagonistic amount of a compound of claim 7.

12. A method for preventing or treating in a mammal a disease caused by the formation of thrombus which comprises as administering a thrombus formation inhibition effective amount of a compound of claim 1.

13. A method for preventing or treating in a mammal a disease caused by the formation of thrombus which comprises as administering a thrombus formation inhibition effective amount of a compound of claim 7.

* * * * *